US010787482B2

(12) United States Patent
Yang et al.

(10) Patent No.: US 10,787,482 B2
(45) Date of Patent: Sep. 29, 2020

(54) EPOXYKETONE COMPOUNDS FOR ENZYME INHIBITION

(71) Applicant: CENTRAX INTERNATIONAL, INC., South San Francisco, CA (US)

(72) Inventors: Jinfu Yang, South San Francisco, CA (US); Jian James Cen, Cixi (CN); Xiaoqing Michelle Fan, South San Francisco, CA (US)

(73) Assignee: CENTRAX INTERNATIONAL INC., South San Francisco, CA (US)

( * ) Notice: Subject to any disclaimer, the term of this patent is extended or adjusted under 35 U.S.C. 154(b) by 0 days.

(21) Appl. No.: 16/665,010

(22) Filed: Oct. 28, 2019

(65) Prior Publication Data
US 2020/0087343 A1 Mar. 19, 2020

Related U.S. Application Data

(63) Continuation of application No. 15/325,998, filed as application No. PCT/US2015/040459 on Jul. 14, 2015, now Pat. No. 10,640,533.

(60) Provisional application No. 62/024,024, filed on Jul. 14, 2014.

(51) Int. Cl.
A61K 38/00 (2006.01)
C07K 5/065 (2006.01)
C07K 5/02 (2006.01)
C07K 5/097 (2006.01)
C07K 5/083 (2006.01)

(52) U.S. Cl.
CPC ........ C07K 5/06078 (2013.01); C07K 5/0202 (2013.01); C07K 5/0806 (2013.01); C07K 5/0821 (2013.01); A61K 38/00 (2013.01)

(58) Field of Classification Search
CPC .............. C07K 5/06078; C07K 5/0821; C07K 5/0202; C07K 5/0806; A61K 38/00
See application file for complete search history.

(56) References Cited

U.S. PATENT DOCUMENTS

| 7,737,112 B2 * | 6/2010 | Lewis ............... A61K 38/14 514/3.8 |
| 8,716,322 B2 | 5/2014 | Zhou et al. |
| 2005/0256324 A1 | 11/2005 | Laidig et al. |
| 2015/0203534 A1 | 7/2015 | Slassi |

FOREIGN PATENT DOCUMENTS

| CN | 105960399 B | 9/2018 |
| EP | 3166933 B1 | 8/2018 |
| JP | 5436860 B2 | 4/2009 |
| JP | 6608442 B2 | 11/2019 |
| WO | 2005105827 A2 | 11/2005 |
| WO | 2007056464 A1 | 5/2007 |
| WO | 2008140782 A2 | 11/2008 |
| WO | 2010048298 A1 | 4/2010 |
| WO | 2011136905 A2 | 11/2011 |
| WO | 2013033396 A2 | 3/2013 |
| WO | 2014/015157 A2 | 1/2014 |
| WO | 2014018807 A1 | 1/2014 |
| WO | 2014026282 A1 | 2/2014 |
| WO | 2014029022 A1 | 2/2014 |

OTHER PUBLICATIONS

Keiji Tanaka, "The proteasome: Overview of structure and functions," Exhibit C Proceedings of the Japan Acade, 2009 vol. 85 Issue 1 pp. 12-36 doi: 10.2183/pjab/85.12.
Britton et al. "Selective Inhibitor of Proteasome's Caspase-like Sites Sensitizes Cells to Specific Inhibition of Chymotrypsin-like Sites," Chemistry & Biology, vol. 16, Issue 12, Dec. 24, 2009, pp. 1278-1289 https://doi.org/10.1016/j.chembiol.2009.11.015.
Demo et al.,"Antitumor Activity of PR-171, a Novel Irreversible Inhibitor of the Proteasome," Cancer Res 2007; 67(13) Jul. 1, 2007, p. 6383-6391 doi:10.1158/0008-5472.CAN-06-4086, https://cancerres.aacrjournals.org/content/67/13/6383.
Lv et al., "Structure-activity relationships and molecular design of epoxyketone peptide proteasome inhibitors," Chemical Research and Application, vol. 24 (9), Sep. 30, 2012, p. 1376-1388, including English translation http://en.cnki.com.cn/Article_en/CJFDTotal-HXYJ201209011.htm.
Zhang et al., "Design, Synthesis and Biological Evaluation of Peptidyl Epoxyketone Proteasome Inhibitors Composed of β-amino Acids," Chem Biol Drug Des. Nov. 2014;84(5):497-504 https://www.ncbi.nlm.nih.gov/pubmed/24751157, doi: 10.1111/cbdd.12342. Epub Jun. 3, 2014.
Zhang et al., "Design, synthesis and biological evaluation of novel tripeptidyl epoxyketone derivatives constructed from [beta]-amino Acids as Proteasome Inhibitors," Bioorg Med Chem. Jun. 1, 2014;22(11):2955-2965 https://www.ncbi.nlm.nih.gov/pubmed/24767818, doi:10.1016/J.BMC.2014.04.011, Epub Apr. 13, 2014.
CN, Search Report for Chinese patent application 201580002532.1, dated Jan. 25, 2018, 1 page (Chinese and English).
CN, 1st Office Action for Chinese patent application 20158002532.1, dated Feb. 2, 2018, 4 pages and extra 6 pages of English translation.
CN, Patent Grant Notice for Chinese patent application 20158002532.1, dated Jul. 25, 2018, 1 page and extra 2 pages of English translation.
Supplementary European Search Report for EP15821964, dated Jun. 14, 2017, 4 pages.
International Search Report for international patent application PCT/US2015/040459, dated Jun. 13, 2016, 7 pages.
Written Opinion for International Search Report for international patent application PCT/US2015/040459, dated Jun. 13, 2016, 8 pages.
International Preliminary Report on Patentability for international patent application PCT/US2015/040459, dated Jan. 17, 2017, 9 pages.

(Continued)

Primary Examiner — Sudhakar Katakam
(74) Attorney, Agent, or Firm — Rimon, P.C.

(57) ABSTRACT

The present disclosure relates to novel compounds and pharmaceutical compositions thereof which are useful as inhibitors of proteasomes. The compounds provided herein have improved proteasome potency and selectivity, and increased aqueous solubility, and are useful in treating various conditions or diseases associated with proteasomes.

20 Claims, 2 Drawing Sheets

(56) References Cited

OTHER PUBLICATIONS

Office Action for Japanese patent application JP2017-523185 (based on PCT/US2015/040459, dated May 7, 2019, 2 pages with extra 1 page of English language equivalent or summary.
Response to 1st Office Action for Chinese patent application CN2013103177668, dated Jan. 8, 2018, 15 pages (including a cited article, plase see item 5 in the section of Non-Patent Literature Documents of this IDS).
Response to 1st Office Action for Chinese patent application CN201580002532.1, dated Mar. 30, 2018, 6 pages.
Response to Communication pursuant to Article 94(3) EPC for European patent application EP15821964.2 (PCT/US2015/040459), dated Jan. 29, 2018, 3 pages.
Response to Notice of Reasons for Refusal for Japanese patent application JP2017-523185, dated Aug. 7, 2019, 1 page with extra 1 page of English language equivalent or summary.
International Search Report for international patent application PCT/US2010/040450, dated Aug. 17, 2010, 2 pages.
Request for Continued Examination Transmittal for U.S. Appl. No. 15/325,998, dated Nov. 26, 2019, 3 pages.
Notice of Allowance for U.S. Appl. No. 15/325,998, dated Aug. 27, 2019, 8 pages.
Applicant summary of interview with examiner for U.S. Appl. No. 15/325,998, dated Jul. 24, 2019, 3 pages.
Applicant Initiated Interview Summary (PTOL-413) for U.S. Appl. No. 15/325,998, dated Jul. 1, 2019, 3 pages.
Electronic Request for Interview with Examiner for U.S. Appl. No. 15/325,998, dated Jun. 20, 2019, 1 page.
Amendment/Req. Reconsideration-After Non-Final Reject for U.S. Appl. No. 15/325,998, dated Jun. 12, 2019, 1 pages.
Applicant Arguments/Remarks Made in an Amendment and Claims for U.S. Appl. No. 15/325,998, dated Jun. 12, 2019, 18 pages.
Non-Final Rejection for U.S. Appl. No. 15/325,998, dated Mar. 27, 2019, 9 pages.
Response to Election/Restriction for U.S. Appl. No. 15/325,998, dated Jan. 23, 2019, 1 pages.
Applicant Arguments/Remarks Made in an Amendment and claims for U.S. Appl. No. 15/325,998, dated Jan. 23, 2019, 9 pages.
Requirement for Restriction/Election for U.S. Appl. No. 15/325,998, dated Nov. 26 2018, 7 pages.

\* cited by examiner

EPOXYKETONE COMPOUNDS FOR ENZYME INHIBITION

CROSS-REFERENCE TO RELATED APPLICATIONS

This present application is a continuation application of U.S. Non-provisional application Ser. No. 15/325,998, filed Jan. 12, 2017 which, is a U.S. National phase filing of international patent application serial number PCT/IB2017/056511, entitled "EPDXYKETONE COMPOUNDS FOR ENZYME INHIBITION" having an international filing date of Jul. 14, 2015. The application claims priority to U.S. Provisional Patent Application Number 62/024,024 filed on Jul. 14. 2014, which are incorporated herein by reference in their entireties for all purposes.

FIELD OF THE INVENTION

The present disclosure relates to compounds that have a backbone of peptide epoxyketone structure. These compounds are useful in, for example, inhibiting proteasomes.

BACKGROUND

Proteasome is a multicatalytic protease complex that plays a critical role in mediating the regulated degradation of intracellular proteins. In vivo, the proteasome complex is believed to exist as 26S proteasome, which is about 2000 kDa in molecular weight and consists of one 20S core particle (20S proteasome) and two 19S regulatory particles. The core is hollow and provides an enclosed cavity in which proteins are degraded. Each end of the core particle associates with a 19S regulatory subunit that contains multiple ATPase active sites and ubiquitin binding sites, which recognizes polyubiquitinated proteins and transfers them to the catalytic core. An alternative form of regulatory subunit called the 11S particle associates with the core in essentially the same manner as the 19S particle; the 11S may play a role in degradation of foreign peptides. The core particle 20S proteasome is about 700 kDa in molecular weight and is comprised of 28 subunits organized into four rings. In yeast and other eukaryotes, 7 α subunits form each of the two outer rings and 7 β subunits form each of the two inner rings. The a rings serve as binding sites for the 19S or 11S regulatory complex, as well as a physical barrier for the two inner β rings. The two inner β rings contain active proteolytic sites. Degradation of proteins occurs within the central chamber formed by the association of the two β rings. In vivo, inhibition of the 20S proteasome can be directly correlated to inhibition of the 26S proteasome. There are two forms of proteasomes: the constitutive proteasome ubiquitously expressed by the majority of cells in the body, and the immunoproteasome, predominantly expressed in hematopoietic cells and cells that have been exposed to inflammatory cytokines. Proteasome-mediated protein degradation is a highly regulated process that is necessary for a variety of intracellular processes. Through the use of different peptide substrates, three major proteolytic activities have been defined for the eukaryote proteasome: chymotrypsin-like activity (CT-L), which cleaves after large hydrophobic residues; trypsin-like activity (T-L), which cleaves after basic residues; and peptidylglutamyl peptide hydrolyzing activity (PGPH), which cleaves after acidic residues. Proteasome has long been recognized as an attractive target for drug development, and was first clinically validated as a therapeutic target in oncology (Orlowski and Kuhn, *Clin. Cancer Res.* (2008), 14, 1649-1657).

Several small molecules have been used to inhibit proteasome activity, including peptide boronic acids, β-lactones and peptide epoxyketones (Bennett and Kirk, Current Opinion in Drug Discovery & Development (2008), 11, 616-625; Borissenko and Groll, *Chem. Rev.* (2007) 107, 687-717). However, these compounds generally lack appropriate specificity and/or potency necessary to fully explore and exploit the roles of proteasome at molecular, cellular and in vivo level. For example, peptide boronic acids and β-lactones are non-specific for proteasome, as they have been found to inhibit other proteases (Borissenko and Groll, *Chem. Rev.* (2007) 107, 687-717; Myung et al., *Medicinal Research Reviews* (2001), 21, 245-273). This raises the possibility that these inhibitors could exhibit off-target activities in vivo that are associated with inhibition of non-proteasome targets. On the other hand, the peptide epoxyketones as disclosed in U.S. Pat. No. 8,088,741B2, U.S. Pat. No. 6,831,099B1, WO2005/105827, CN101044157A, U.S. Pat. No. 7,687,452B2 and US2007/0105786A1 are highly selective as inhibitors of proteasomes. However, these peptide epoxyketones have poor aqueous solubility and/or less optimal proteasome inhibitory potency. Therefore, there are needs in the art to develop novel proteasome inhibitors that have improved pharmaceutical and/or biological properties.

SUMMARY

Provided herein are compounds that have a tri-peptide ketone epoxy backbone. Also disclosed herein are compounds of increased aqueous solubility and improved proteasome inhibitory property.

In certain embodiments, the present disclosure provides compounds having a structure shown in Formula (I), and an enantiomer, diastereomer, tautomer, pharmaceutically acceptable salt or solvate or prodrug thereof Formula (I)

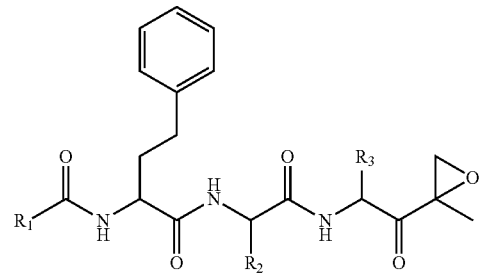

wherein $R_1$ is —$(CH_2)$m-$R_4$, wherein m=0 or 1, $R_4$ is selected from the group consisting of $C_{1-10}$alkyl,

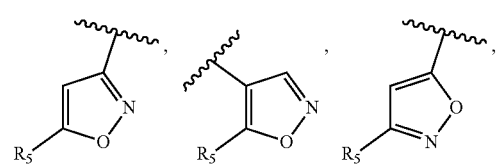

-continued

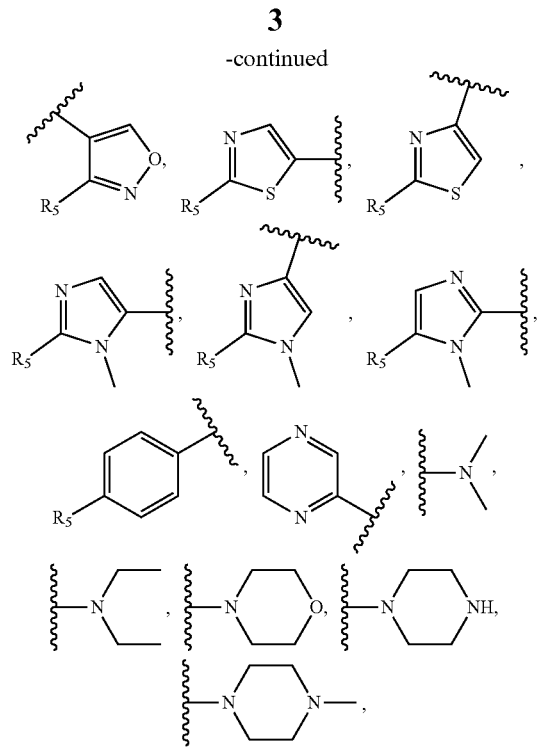

wherein
each of $R_5$ is independently H, hydroxyl, $C_{1-10}$alkyl, $C_{1-10}$alkoxyl, $C_{1-10}$hydroxyalkyl, $C_{1-10}$alkyloxyalkyl, $NH_2$, $NHR_6$, $-R_7-O(C=O)-R_8$, $-R_7-(C=O)$ $X-R_8$, $-R_7-OPO_3M_1M_2$,

wherein
$R_6$ is $C_{1-10}$alkyl, phenyl, $-(C=O)-C_{1-6}$alkyl or $-(C=O)$-phenyl,
each of $R_7$, and $R_9$ is independently absent or $C_{1-10}$alkylene,
each of $R_8$ is independently H, hydroxyl, metal or $C_{1-10}$alkyl, $-C_{1-10}$alkylene, $-NR_{10}R_{11}$, or $-OPO_3M_1M_2$,
each of $R_{10}$ and $R_{11}$ is independently H, $C_{1-10}$alkyl (e.g. $C_{1-6}$alkyl) or substituted $C_{1-10}$alkyl (e.g. $C_{1-6}$alkyl),
each of $M_1$, and $M_2$ is independently H or metal,
X is absent or O,
Y is absent or $-(C=O)-$,
Z is absent or O; and
each of $R_2$ and $R_3$ is independently selected from $C_{1-10}$alkyl, $C_{1-10}$alkenyl, $C_{1-10}$hydroxyalkyl, $C_{1-10}$alkoxyalkyl, aryl, $C_{1-10}$aralkyl, heteroaryl, $C_{1-10}$heteroaralkyl, heterocyclyl, $C_{1-10}$heterocycloalkyl, carbocyclyl, and $C_{1-10}$carbocycloalkyl, wherein $R_3$ is not 4-pyridylmethyl when $R_1$ is

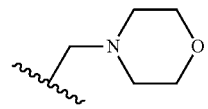

and $R_2$ is isobutyl.

In certain embodiments, the compound of Formula (I) as provided herein has a configuration shown in Formula (II):

Formula (II)

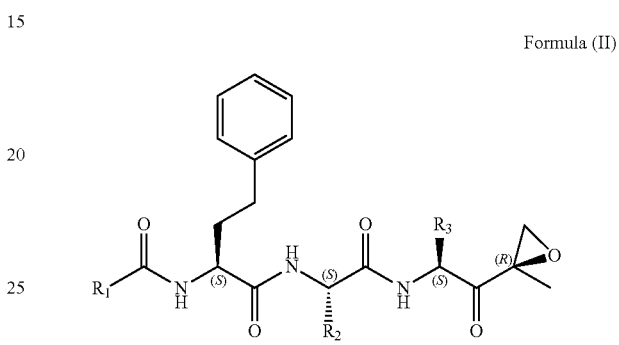

wherein each of $R_1$, $R_2$ and $R_3$ is as defined supra.
In certain embodiments, $R_4$ is selected from the group consisting of

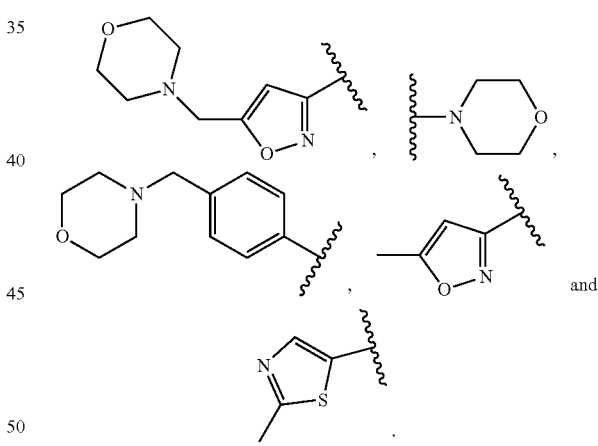

and

In certain embodiments, $R_1$ is selected from the group consisting of

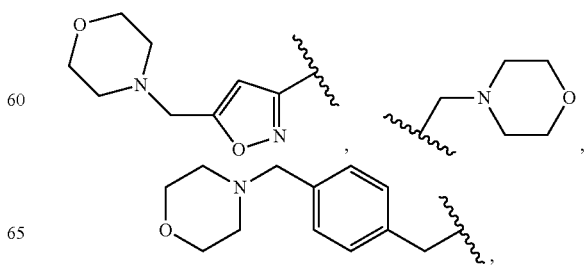

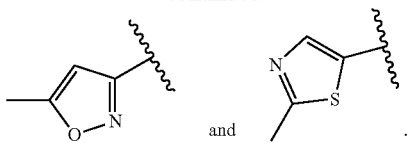

In certain embodiments, $R_2$ is $C_{1-10}$alkyl, $C_{1-10}$alkoxyalkyl, aryl, heteroaryl, $C_{1-10}$aralkyl or $C_{1-10}$heteroaralkyl.

In certain embodiments, $R_2$ is methyl-oxy-methyl, 4-pyridylmethyl, isobutyl, benzyl or 4-thiazolyl-methyl.

In certain embodiments, $R_3$ is $C_{1-10}$alkyl, aryl, heteroaryl, $C_{1-10}$aralkyl or $C_{1-10}$heteroaralkyl.

In certain embodiments, $R_3$ is isobutyl, 4-pyridylmethyl or benzyl.

In one aspect, the present disclosure provides tri-peptide epoxyketones that can inhibit catalytic activity of the 20S proteasome. In certain embodiments, the tri-peptide epoxyketones provided herein have an inhibition $IC_{50}$ of CT-L catalytic activity of the 20S proteasome at concentration below about 500 nM, 250 nM, 100 nM, 50 nM, 10 nM, or 5 nM.

In another aspect, the compounds disclosed herein have improved aqueous solubility. In certain embodiments, the tri-peptide epoxyketones provided herein have aqueous solubility of at least about 0.02, 0.05, 0.1, 0.5 or 1 mg/mL.

In further aspect, the present disclosure provides pharmaceutical compositions comprising a pharmaceutically acceptable carrier and a therapeutically effective amount of a 20S proteasome inhibitor disclosed herein, which are useful, for example, in treatment of human conditions, including but not limited to, cancer, inflammation, neurodegenerative disease (such as Alzheimer's disease), muscle-wasting disease, chronic infectious diseases, fever, muscle disuse, denervation, nerve injury, and immune-related conditions, among others.

In certain embodiments, the pharmaceutical compositions comprise about $10^{-9}$ g to about 10 g of a compound provided herein. Suitable dosages per subject per day can be from about 0.01 mg to about 5 g.

In certain embodiments, the compounds or pharmaceutical compositions disclosed herein are formulated into a dosage form which is suitable for delivery to a subject in need thereof through a parenteral route (e.g. subcutaneous, intravenous, intramuscular, intraarterial, intrathecal, intracapsular, intraorbital, intra cardiac, intradermal, intraperitoneal, transtracheal, subcuticular, intraarticular, subcapsular, subarachnoid, intraspinal, intrasternal, and/or infusion) and a non-parenteral route (e.g. oral, enteral, buccal, nasal, intranasal, transmucosal, epidermal, transdermal, dermal, ophthalmic, pulmonary, sublingual, rectal, vaginal or topical).

Another aspect of the present disclosure relates to methods of treating a condition associated with 20S proteasome, comprising administering a therapeutically effective amount of a compound provided herein.

In a further aspect, the present disclosure provides a method of making a peptide epoxyketone.

Other features and advantages of the present disclosure will be apparent from the following detailed description, and from the claims.

DETAILED DESCRIPTION

Compounds and Pharmaceutical Salts Thereof

Figure 1:
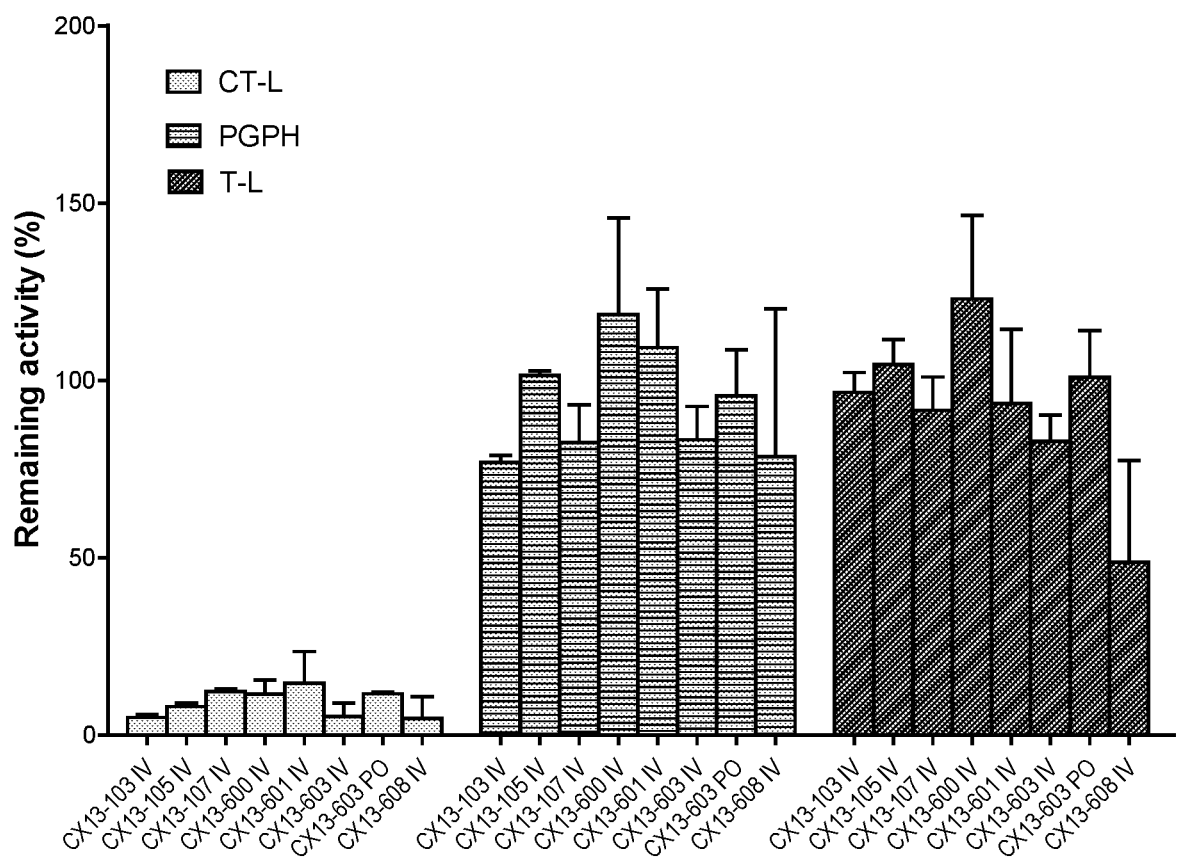
FIG. 1 shows the remaining percentage of the proteasome activity in the blood samples collected from Balb/c mice administrated of a compound described herein. The proteasome activity in the blood samples collected from mice administrated of the vehicle was considered as 100% (control group). The remaining activity was calculated by comparing the proteasome activity in the blood samples collected from mice administrated of a compound described herein via intravenous injection (IV) at 10 mg/kg or via oral gavage (PO) at 30 mg/kg to the control group.

In one aspect, the present disclosure provides compounds that have a structure of Formula (I), and an enantiomer, diastereomer, tautomer, pharmaceutically acceptable salt or solvate or prodrug thereof:

Formula (I)

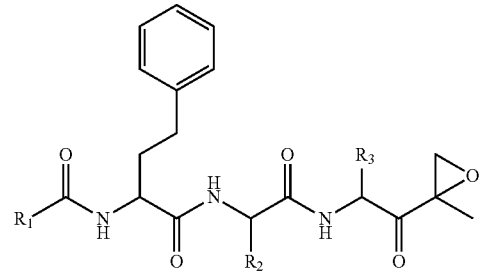

wherein $R_1$ is —$(CH_2)$m-$R_4$, wherein m=0 or 1, $R_4$ is selected from the group consisting of $C_{1-10}$alkyl,

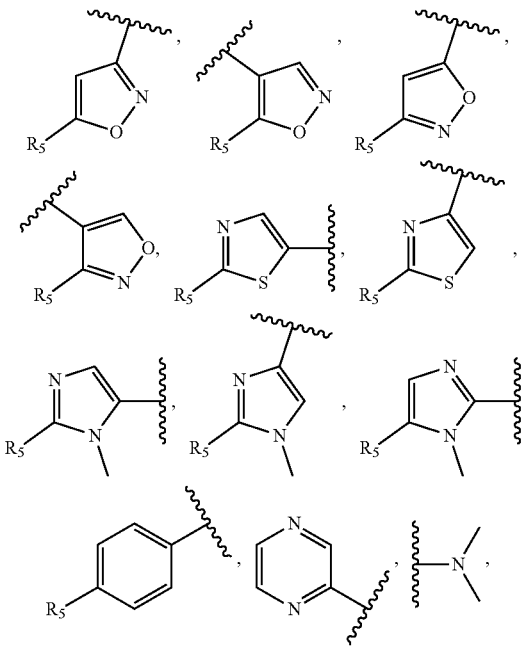

-continued

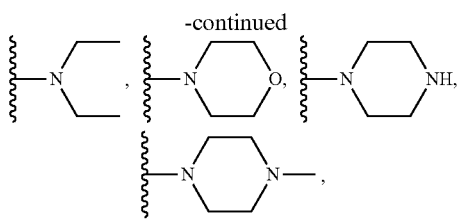

wherein
each of $R_5$ is independently H, hydroxyl, $C_{1-10}$alkyl, $C_{1-10}$alkoxyl, $C_{1-10}$hydroxyalkyl, $C_{1-10}$alkyloxyalkyl, $NH_2$, $NHR_6$, $-R_7-O(C=O)-R_8$, $-R_7-(C=O)X-R_8$, $-R_7-OPO_3M_1M_2$,

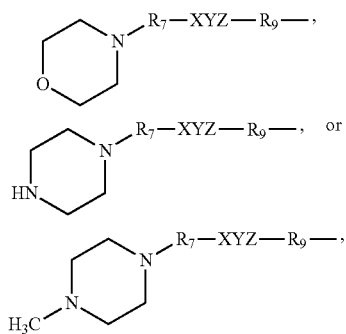

wherein
$R_6$ is $C_{1-10}$alkyl, phenyl, $-(C=O)-C_{1-6}$alkyl or $-(C=O)$-phenyl,
each of $R_7$, and $R_9$ is independently absent or $C_{1-10}$alkylene,
each of $R_8$ is independently H, hydroxyl, metal or $C_{1-10}$alkyl, $-C_{1-10}$alkylene, $-NR_{10}R_{11}$, or $-OPO_3M_1M_2$,
each of $R_{10}$ and $R_{11}$ is independently H, $C_{1-10}$alkyl (e.g. $C_{1-6}$alkyl) or substituted $C_{1-10}$alkyl (e.g. $C_{1-6}$alkyl),
each of $M_1$, and $M_2$ is independently H or metal,
X is absent or O,
Y is absent or $-(C=O)-$,
Z is absent or O; and
each of $R_2$ and $R_3$ is independently selected from $C_{1-10}$alkyl, $C_{1-10}$alkenyl, $C_{1-10}$hydroxyalkyl, $C_{1-10}$alkoxyalkyl, aryl, $C_{1-10}$aralkyl, heteroaryl, $C_{1-10}$heteroaralkyl, heterocyclyl, $C_{1-10}$heterocycloalkyl, carbocyclyl, and $C_{1-10}$carbocycloalkyl,
wherein $R_3$ is not 4-pyridylmethyl when $R_1$ is

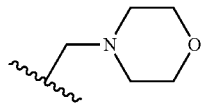

and $R_2$ is isobutyl.

In certain embodiments, $R_5$ is $-R_7-O(C=O)-R_8$, and $R_7$ and $R_8$ are defined as supra. In certain embodiments, $R_7$ is absent, and $R_8$ is selected from H, $C_{1-10}$alkyl (e.g. $C_{1-4}$alkyl, $C_{1-6}$alkyl), $-C_{1-10}$alkylene, $-NR_{10}R_{11}$, wherein $R_{10}$ and $R_{11}$ are defined supra. In certain embodiments, $R_7$ is $C_{1-10}$alkylene (e.g. $-CH_2-$, $-C_2H_4-$, $-C_3H_7-$, etc.), and $R_8$ is selected from H, $C_{1-10}$alkyl (e.g. $C_{1-6}$alkyl), $-C_{1-10}$alkylene, $-NR_{10}R_{11}$, wherein $R_{10}$ and $R_{11}$ are defined supra.

In certain embodiments, $R_5$ is $-R_7-(C=O)X-R_8$, and $R_7$ and $R_8$ are defined as supra. In certain embodiments, $R_7$ is absent, X is O, and $R_8$ is selected from H, metal (e.g. Na, and K), $NH_4$, $C_{1-10}$alkyl (e.g. $C_{1-6}$alkyl), $-C_{1-10}$alkylene, and $-NR_{10}R_{11}$, wherein $R_{10}$ and $R_{11}$ are defined supra. In certain embodiments, $R_7$ is absent, X is absent, and $R_8$ is selected from $-NR_{10}R_{11}$, wherein $R_{12}$ and $R_{13}$ are defined supra.

In certain embodiments, $R_5$ is $NH_2$, NHCOMe, NHCOEt, $NHCOC_3H_7$, or NHBoc.

In certain embodiments, $R_5$ is

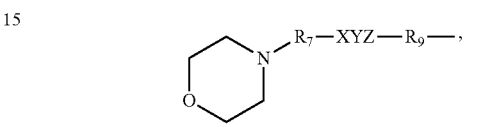

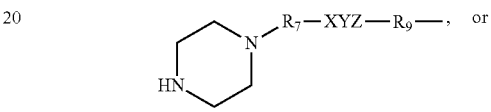

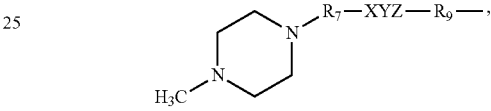

and $R_7$, $R_9$, X, Y, and Z are defined as supra. In certain embodiments, at least one of $R_7$, $R_9$, X, Y, and Z is not absent. In certain embodiments, all of X, Y, Z and $R_7$ are absent, and $R_9$ is $C_{1-10}$alkylene (e.g. $-CH_2-$, $-C_2H_4-$, $-C_3H_7-$, etc.). In certain embodiments, all of $R_7$, $R_9$ and X are absent, Y is $-(C=O)-$ and Z is O. In certain embodiments, both of $R_7$ and X are absent, $R_9$ is $C_{1-10}$alkylene (e.g. $-CH_2-$, $-C_2H_4-$, $-C_3H_7-$, etc.), Y is $-(C=O)-$ and Z is O. In certain embodiments, both of $R_9$ and X are absent, $R_7$ is $C_{1-10}$alkylene (e.g. $-CH_2-$, $-C_2H_4-$, $-C_3H_7-$, etc.), Y is $-(C=O)-$ and Z is O.

In certain embodiments, X is absent, both of $R_7$ and $R_9$ are independently $C_{1-10}$alkylene (e.g. $-CH_2-$, $-C_2H_4-$, $-C_3H_7-$, etc.), Y is $-(C=O)-$ and Z is O. In certain embodiments, all of $R_7$, $R_9$, X and Z are absent, and Y is $-(C=O)-$.

In certain embodiments, each of $R_5$ is independently H, $-CH_3$, $-C_2H_5$, $-C_3H_7$,

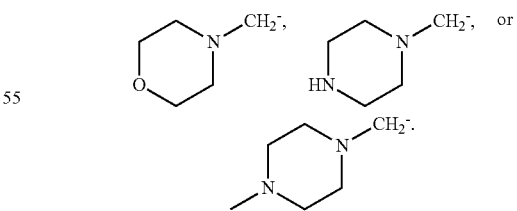

In certain embodiments, each of $R_5$ is independently $-OH$, $-OCH_3$, $-OC_2H_5$, $-OC_3H_7$, $-OPO_3Na_2$, $-OC(=O)CH_3$, $-OC(=O)C_2H_5$, $-OC(=O)C_3H_7$, $-OC(=O)C_4H_9$, $-OC(=O)CH_2NH_2$, $-OC(=O)CH_2N(CH_3)_2$, $-OC(=O)CH_2N(C_2H_5)_2$, $-OC(=O)NH_2$, $-OC(=O)N(CH_3)_2$, $-OC(=O)N(C_2H_5)_2$,

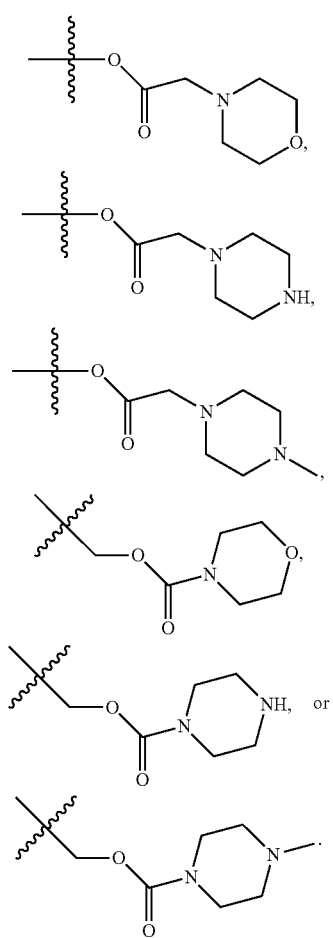

In certain embodiments, each of $R_5$ is independently —$CH_2OH$, —$C_2H_5OH$, —$C_3H_7OH$, —$CH_2OC(=O)CH_3$, —$CH_2OC(=O)C_2H_5$, —$CH_2OC(=O)C_3H_7$, —$CH_2OC(=O)C_4H_9$, —$CH_2OPO_3Na_2$, —$CH_2OC(=O)CH_2NH_2$, —$CH_2OC(=O)CH_2N(CH_3)_2$, —$CH_2OC(=O)CH_2N(C_2H_5)_2$,

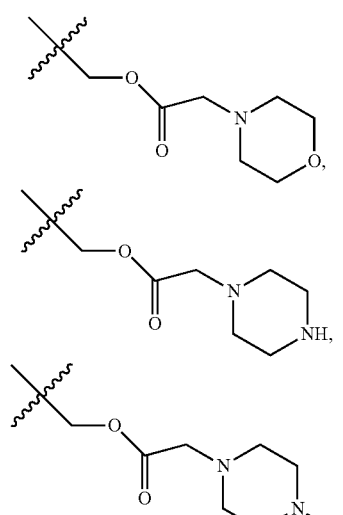

—$CH_2OC(=O)NH_2$, —$CH_2OC(=O)N(CH_3)_2$, —$CH_2OC(=O)N(C_2H_5)_2$,

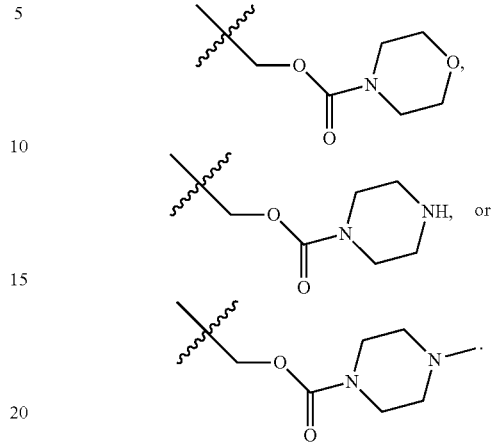

In certain embodiments, each of $R_5$ is independently —$(C=O)OH$, —$(C=O)ONa$, —$(C=O)ONH_4$, —$(C=O)OCH_3$, —$(C=O)OC_2H_5$, —$(C=O)OC_3H_7$, or —$(C=O)OC_4H_9$.

In certain embodiments, each of $R_5$ is independently —$CONH_2$, —$CON(CH_3)_2$, —$CON(C_2H_5)_2$,

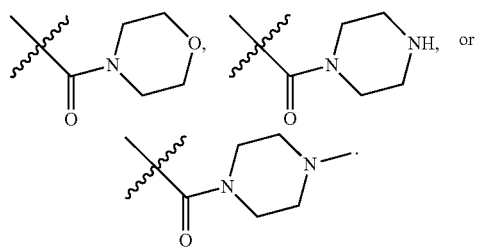

In certain embodiments, $R_1$ is selected from the group consisting of methyl,

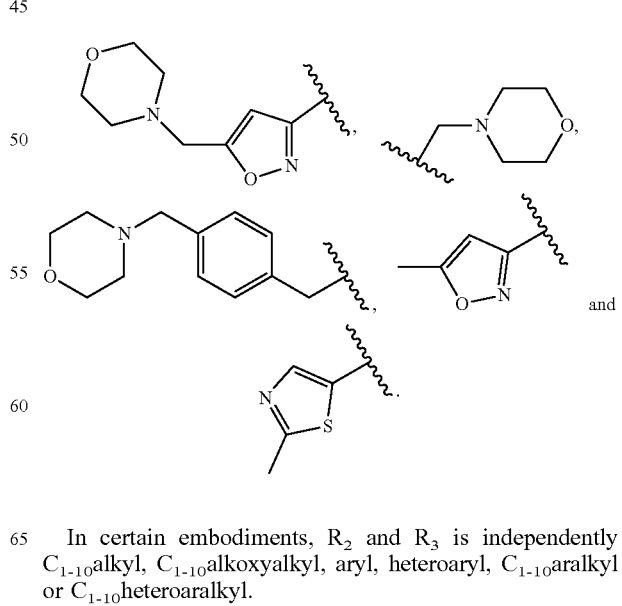

In certain embodiments, $R_2$ and $R_3$ is independently $C_{1-10}$alkyl, $C_{1-10}$alkoxyalkyl, aryl, heteroaryl, $C_{1-10}$aralkyl or $C_{1-10}$heteroaralkyl.

In certain embodiments, $R_2$ and $R_3$ is independently —$(CH_2)nR_{12}$, $R_{12}$ is $C_{1-6}$alkyl, phenyl, pyridyl, —O—$C_{1-6}$ alkyl, thiazolyl, wherein n=0, 1, 2, 3, 4, 5.

In certain embodiments, $R_2$ is methyl-oxy-methyl, 4-pyridylmethyl, isobutyl, benzyl or 4-thiazolyl-methyl.

In certain embodiments, $R_3$ is isobutyl, 4-pyridylmethyl or benzyl.

Examples of compounds having a structure of Formula (I) include, without limitation, compounds listed below:

I-103

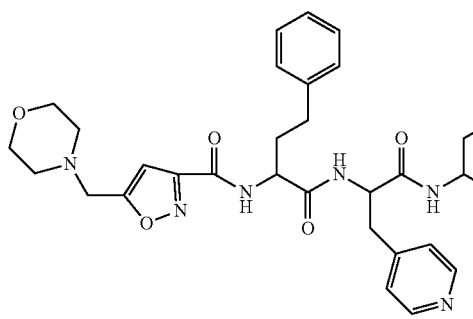

I-104

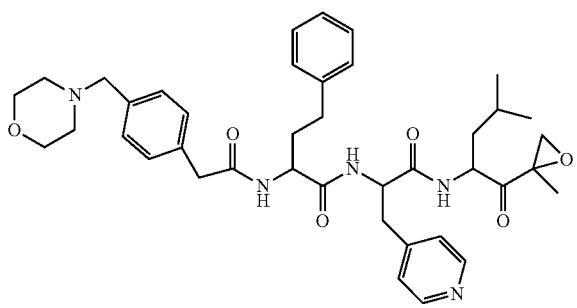

I-105

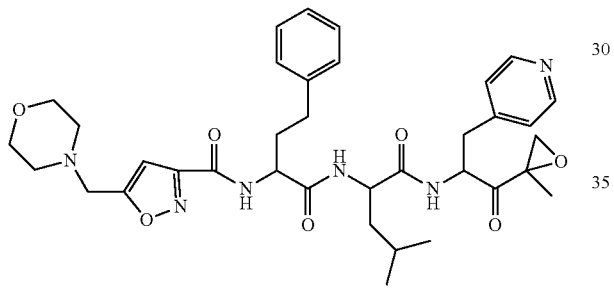

I-107

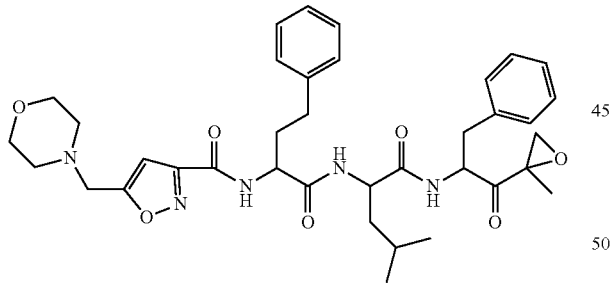

I-130

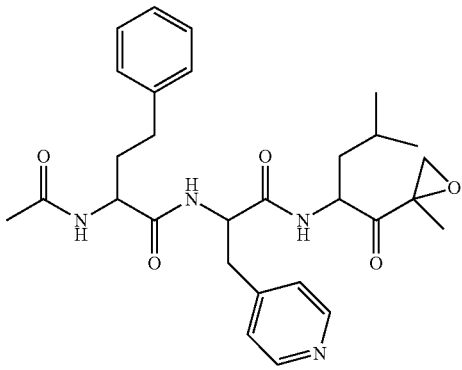

I-133

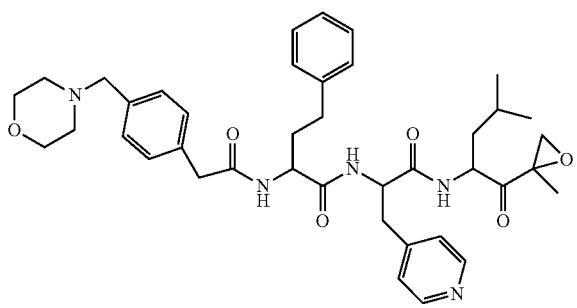

I-135

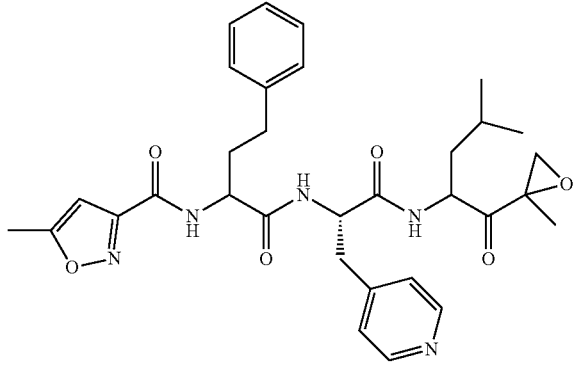

I-137

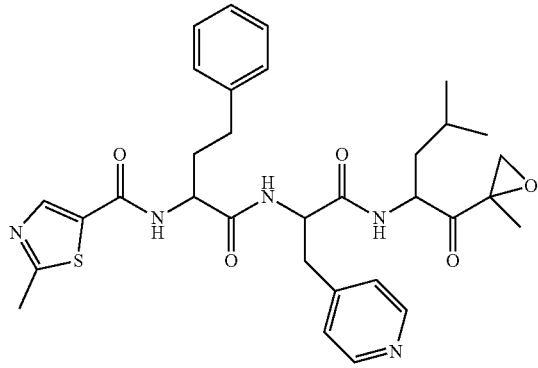

-continued

I-600

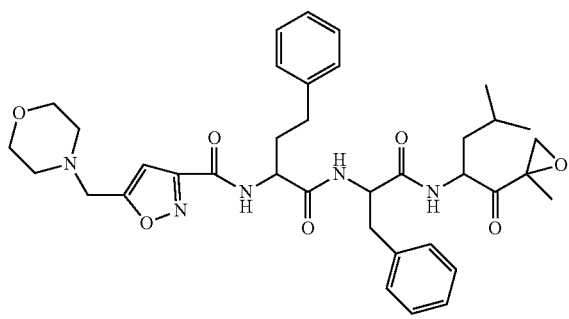

I-601

I-603

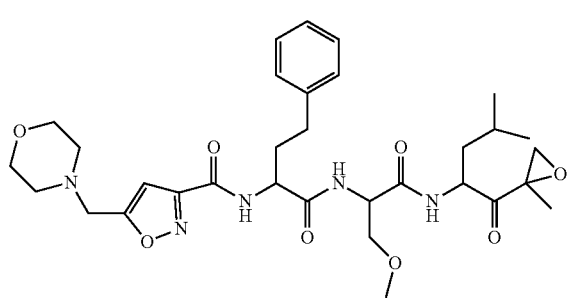

I-605

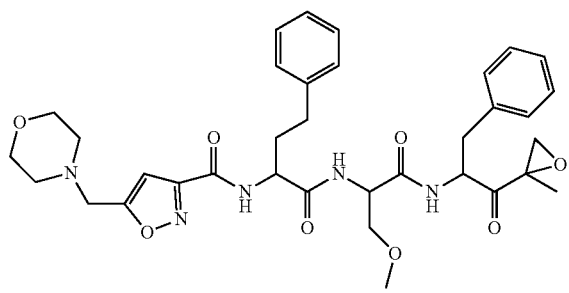

I-606

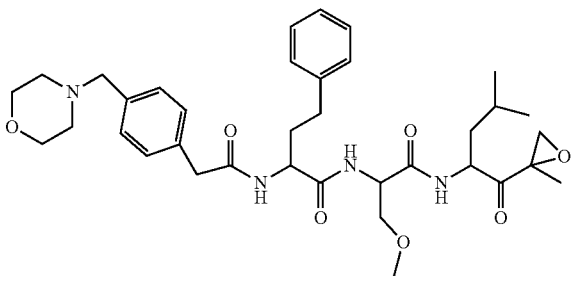

-continued

I-608

I-705

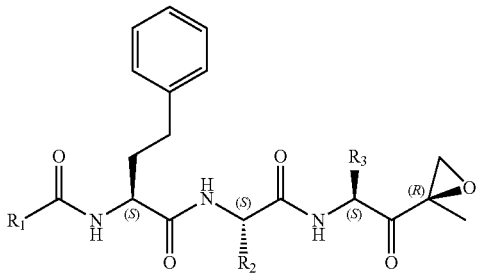

wherein each of the chiral carbons in Formula (I) can be independently in R configuration or S configuration.

In certain embodiments, a compound of Formula (I) has a configuration shown in Formula (II), wherein $R_1$, $R_2$ and $R_3$ have definitions as provided supra:

Formula (II)

In certain embodiments, the compounds provided herein comprise a structure selected from the compounds listed below, and enantiomers, diastereomers, tautomers, pharmaceutically acceptable salts or solvates or prodrugs thereof:

CX13-103

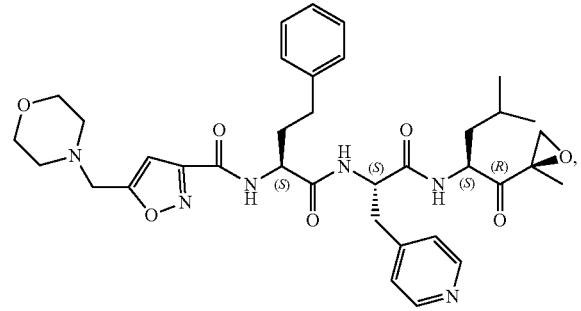

CX13-104
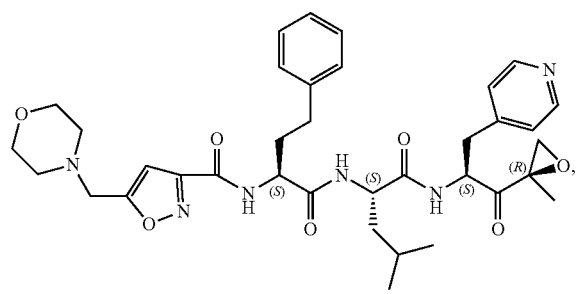
CX13-105
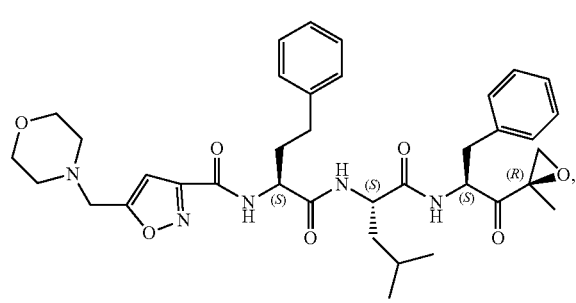
CX13-107
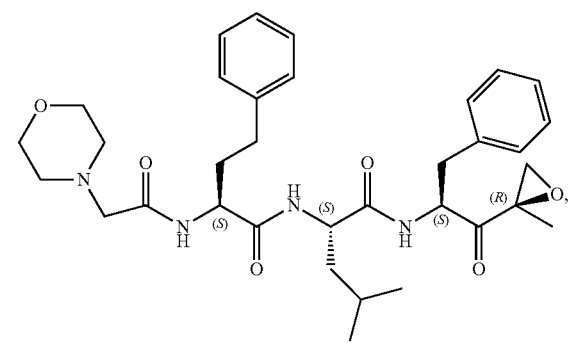
CX13-130
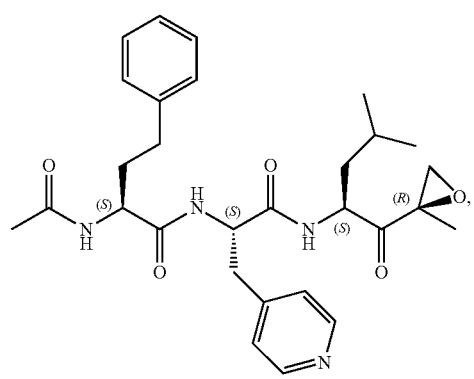
CX13-133
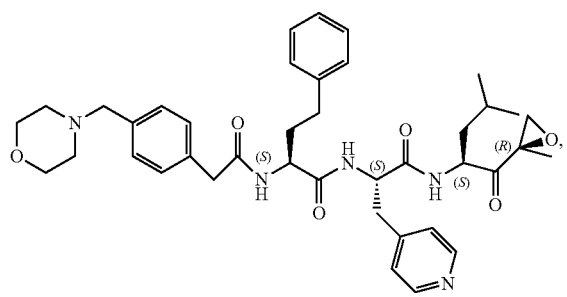
CX13-135
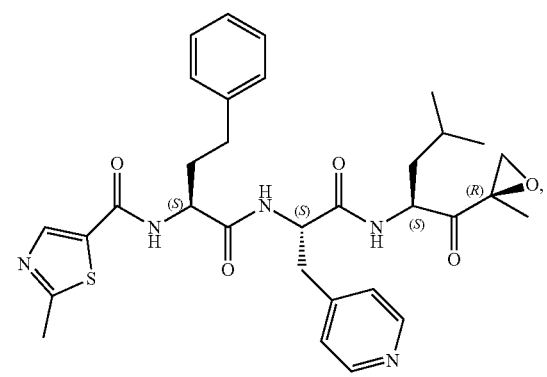
CX13-137
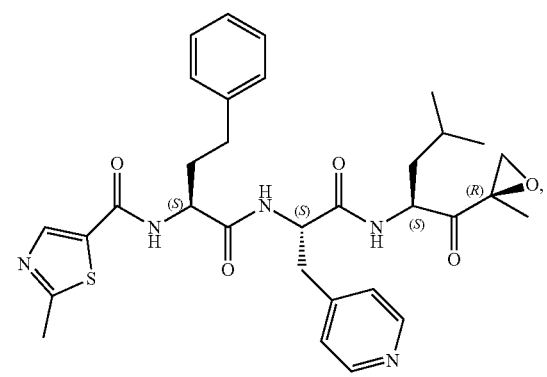
CX13-600
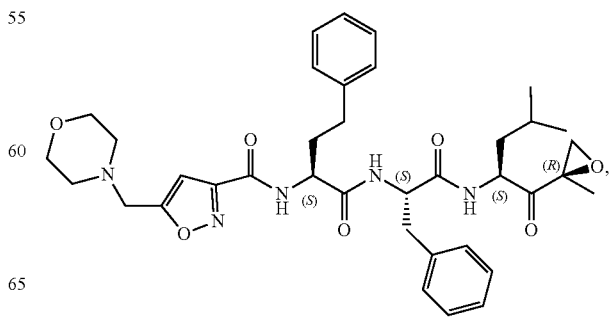

CX13-601
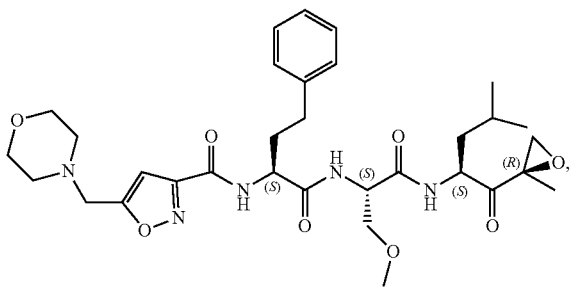

CX13-603
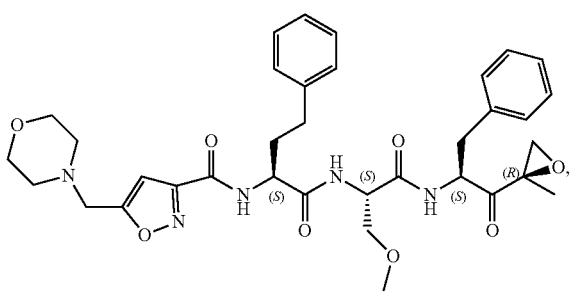

CX13-605
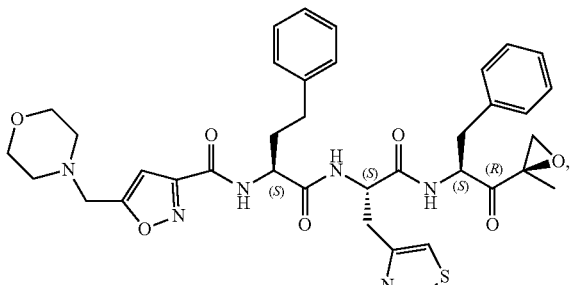

CX13-606
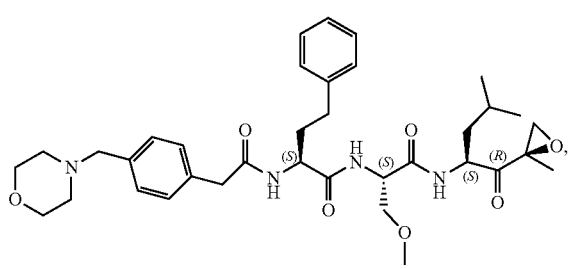

CX13-608
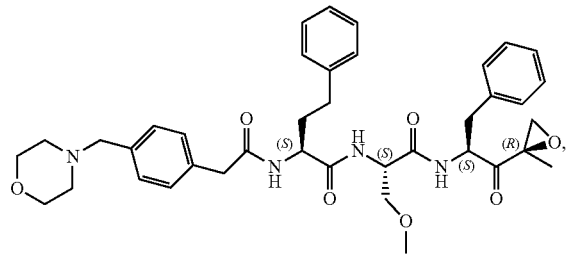

CX13-705
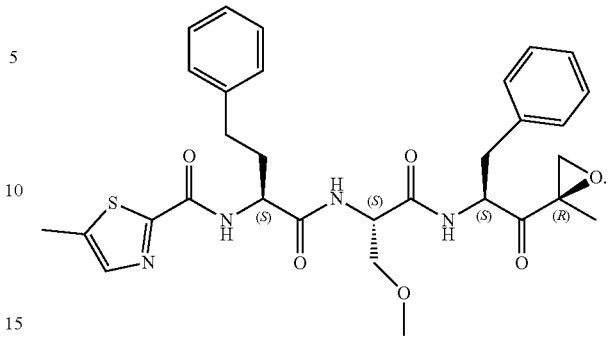

Pharmaceutically acceptable salts can be any salt or ester that are physiologically acceptable and are suitable for administration to an intended recipient. Examples of pharmaceutically acceptable salts include, acid addition salts (e.g. hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate salts), and base salts (e.g. aluminum, calcium, lithium, magnesium, potassium, sodium, zinc, and diethanolamine salts).

Definition

The term "$C_{x-y}$ alkyl" refers to substituted or unsubstituted saturated hydrocarbon groups, including straight-chain alkyl and branched-chain alkyl groups that contain from x to y carbons in the chain.

The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-10}$alkoxyalkyl" refers to a $C_{1-10}$alkyl group substituted with an alkoxy group, thereby forming an ether.

The term "$C_{1-10}$aralkyl", as used herein, refers to a $C_{1-10}$alkyl group substituted with an aryl group.

The term "$C_{1-10}$heteroaralkyl", as used herein, refers to $C_{1-10}$alkyl group substituted with an heteroaryl group.

The term "aryl" as used herein includes 5-, 6-, and 7-membered substituted or unsubstituted single-ring aromatic groups in which each atom of the ring is carbon.

The terms "heteroaryl" includes substituted or unsubstituted aromatic 5- to 7-membered ring structures, more preferably 5- to 6-membered rings, whose ring structures include one to four heteroatoms.

The terms "carbocycle" and "carbocyclyl", as used herein, refer to a non-aromatic substituted or unsubstituted ring in which each atom of the ring is carbon.

The terms "heterocyclyl" or "heterocyclic group" refer to substituted or unsubstituted non-aromatic 3- to 10-membered ring structures, more preferably 3- to 7-membered rings, whose ring structures include one to four heteroatoms.

The term "$C_{1-10}$hydroxyalkyl" refers to a $C_{1-10}$alkyl group substituted with a hydroxy group.

The term "prodrug" encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

Biological Activity, Selectivity and Solubility

The compounds provided herein have biological activity in inhibiting proteasome. Inhibition of the 20S proteasome can be determined by methods and assays known in the art, for example, as disclosed by Stein et al., *Biochemistry* (1996), 35, 3899-3908; by Lightcap et al., *Clinical Chemistry*, 2000, 46, 673-683; by Kisselev et al., *Journal of Biological Chemistry*. (2006), 281, 8582-8590 and in U.S. application Ser. No. 09/569,748. The chymotrypsin-like (CT-L), peptidylglutamyl peptide hydrolyzing (PGPH) and trypsin-like (T-L) activities of the 20S proteasome are measured with a fluorogenic substrate assay method using succinyl-Leu-Leu-Val-Tyr-AMC, Z-Leu-Leu-Glu-AMC and Boc-Leu-Arg-Arg-AMC, respectively, as the substrates in an assay buffer. The free fluorophore 7-Amino-4-methylcoumarin (AMC) after cleavage from the substrates is quantified using a fluorometer and activity of CT-L, PGPH and T-L of 20S proteasome is determined.

The compounds provided herein are useful in part because they inhibit the catalytic activities of proteasome.

In certain embodiments, the compounds provided herein show inhibition (e.g. at least 50% inhibition) of CT-L activity of the 20S proteasome when present at concentrations below about 500 nM, 250 nM, 100 nM (e.g., CX13-130), 50 nM (e.g., CX13-104, CX13-137, CX13-601, CX13-603), 10 nM (e.g., CX13-135, CX13-605, CX13-606, CX13-705) or 5 nM (e.g., CX13-103, CX13-105, CX13-107, CX13-133, CX13-600, CX13-608). In certain embodiments, the compounds provided herein also show inhibition of T-L activity of the 20S proteasome at below about 500 nM (e.g., CX13-133, CX13-606, CX13-608).

In another aspect, the compounds disclosed herein have improved aqueous solubility. In certain embodiments, the tri-peptide epoxyketones provided herein have aqueous solubility of at least about 0.02, 0.05, 0.1, 0.5 or 1 mg/mL.

In another aspect, the tri-peptide epoxyketones provided herein have both improved aqueous solubility and proteasome inhibition. In certain embodiments, the compounds disclosed herein have aqueous solubility of at least about 0.1, 0.5 or 1 mg/mL and show inhibition of CT-L activity of the 20S proteasome when present at concentration below about 100 nM, 50 nM, 10 nM or 5 nM.

Uses of the Compounds

Another aspect of the present disclosure relates to methods of inhibiting the activities of the proteasome, comprising administering a therapeutically effective amount of a compound provided herein. "Therapeutically effective amount" as used herein means the amount of a compound that is sufficient to provide intended therapeutic efficacy or activity in the subject receiving the compound. The effective amount may vary depending on various factors such as age, gender, health condition of the subject, dosage form of the compound, severity of the disease in the subject, and etc. A therapeutically effective amount can be determined by a physician or a doctor prescribing the compound, taking account to the aforementioned factors among others.

Another aspect of the present disclosure relates to methods of treating a condition associated with the proteasome. The method comprises administering an effective amount of a compound provided herein. The compounds provided herein can be used to treat any of the conditions or diseases that are associated with the proteasome, including but not limited to those listed below.

A variety of conditions or diseases have been known or believed to be mediated by the catalytic functions of the proteasome. Proteasome inhibition has been suggested as a prevention and/or treatment of a multitude of diseases including, but not limited to, cancers, neurotoxic/degenerative diseases, Alzheimer's disease, ischemic conditions, inflammation, immune-related diseases, HIV infection, organ graft rejection, septic shock, inhibition of antigen presentation, parasitic infections, conditions associated with acidosis, macular degeneration, pulmonary conditions, muscle wasting diseases, fibrotic diseases, bone and hair growth diseases. Therefore, proteasome inhibitor compositions such as the peptide epoxyketones disclosed herein provide a means of treating patients with these conditions.

Proteasome inhibition has been clinically demonstrated as an antitumor therapeutic strategy. Accordingly, the compounds disclosed herein are useful for treating cancers. Exemplary cancers that may be treated include leukemia, lymphoma, myeloma, and carcinomas, such as hepatocellular carcinoma etc. Other cancers that may be treated with the compounds disclosed herein include adrenocortical carcinoma, AIDS-related carcinomas, astrocytoma, bone carcinoma, osteosarcoma, GBM, malignant fibrous histiocytoma, melanoma, malignant mesothelioma, Pheochromocytoma, pineoblastoma and supratentorial primitive neuroectodermal tumors, neuroblastoma, uterine sarcoma, bile duct cancer, bladder cancer, breast cancers, gastrointestinal cancers, cervical cancers, colon cancers, rectal cancers, esophageal cancers, eye cancers, ovarian cancer, head and neck cancers, kidney cancers, lip and oral cavity cancers, lung cancers, nasal cavity and paranasal sinus cancers, penile cancers, prostate cancers, transitional cell cancers, salivary gland cancers, soft tissue cancers, skin cancers, thyroid, parathyroid cancer, and vaginal cancers.

Proteasome inhibitors have been associated with NF-κB inhibition. NF—κB is a potent transcription factor which mediates transcription of genes including inflammatory molecules such as TNF, IL-1, cyclooxygenase, ICAM, and etc. Accordingly, the compounds provided herein can be used as an immunosuppressant which may be useful in inflammatory disorders or conditions, such as, without limitation, allergy, asthma, rejection of a transplanted organ/tissue, auto-immune diseases lupus, rheumatoid arthritis, psoriasis, multiple sclerosis, and inflammatory bowel diseases. The compounds provided herein may be administered in an effective amount, optionally in a pharmaceutical composition, to a subject in need thereof, to treat these conditions.

Proteasome inhibitors have been found to reduce degradation of muscle proteins, therefore useful in inhibiting muscle loss and fiber atrophy. Accordingly, the compounds provided herein can be used to treat cachexia and muscle-wasting diseases, such as chronic infectious diseases, fever, muscle disuse and denervation, nerve injury, renal failure associated with acidosis, and hepatic failure. In certain embodiments, the compounds provided herein can be administered in an effective amount, optionally in a pharmaceutical composition, to a subject in need thereof, to slow down or reduce muscle protein degradation, intracellular protein degradation or p53 protein degradation in a cell.

The compounds provided herein can also be used to treat neurodegenerative diseases and conditions, including, but not limited to, stroke, ischemic damage to the nervous system, neural trauma (e.g. percussive brain damage, spinal cord injury, and traumatic damage to the nervous system), multiple sclerosis and other immune-mediated neuropathies (e.g. Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinsons's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias, and dementias caused by infections (such as syphilis or chronic meningitis).

The compounds provided herein can further be useful in regulating protein processing that is associated with extracellular deposition of β-amyloid protein (β-AP), the major cause of Alzheimer's disease. Accordingly, the compounds provided herein are useful in treating Alzheimer's disease, for example by reducing the rate of β-AP processing, reducing the rate β-AP plaque formation, reducing the rate of β-AP generation, and reducing the clinical symptoms of Alzheimer's disease.

Proteasome inhibition has also been further associated with reducing fibrosis. Accordingly, the compounds provided herein can be used for treatment of fibrosis related conditions such as, diabetic nephropathy, glomerulosclerosis, IgA nephropathy, cirrhosis, biliary atresia, congestive heart failure, scleroderma, radiation-induced fibrosis, lung fibrosis, and cardiac fibrosis.

Pharmaceutical Compositions and Administration

In another aspect, the present disclosure provides pharmaceutical compositions comprising a compound provided herein and a pharmaceutically acceptable carrier.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a compound provided herein from one location, body fluid, tissue, organ (interior or exterior), or portion of the body, to another location, body fluid, tissue, organ, or portion of the body. Pharmaceutically acceptable carriers can be vehicles, diluents, excipients, or other materials that can be used to contact the tissues of an animal without excessive toxicity or adverse effects. Exemplary pharmaceutically acceptable carriers include, sugars, starch, celluloses, malt, tragacanth, gelatin, Ringer's solution, alginic acid, isotonic saline, buffering agents, and etc.

Each carrier is "pharmaceutically acceptable" in the sense of being compatible with the other ingredients, e.g., a compound provided herein of the formulation and suitable for use in contact with the tissue or organ of a biological subject without excessive toxicity, irritation, allergic response, immunogenicity, or other problems or complications, commensurate with a reasonable benefit/risk ratio.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The pharmaceutical composition can be made into any suitable dosage form, such as solid dosage form (e.g. tablets, capsules, powders, granules and etc.) and liquid dosage form (e.g. aqueous solution, emulsion, elixir, syrup, and etc.). Methods of preparing pharmaceutical compositions are well-known in the art, and can be practiced according to routine procedures as described, for example, by *Remington: The Science and Practice of Pharmacy* (Gennaro ed. 20th edition, Williams & Wilkins PA, USA) (2000).

In certain embodiments, the pharmaceutical compositions comprise about $10^{-9}$ g to about 10 g of a compound provided herein (e.g. about 0.01 mg to about 10 g, about 0.1 mg to about 10 g, about 1 mg to about 10 g, about 5 mg to about 10 g, about 10 mg to about 10 g, about 20 mg to about 10 g, about 30 mg to about 10 g, about 40 mg to about 10 g, about 50 mg to about 10 g, about 80 mg to about 10 g, about 100 mg to about 10 g, about 150 mg to about 10 g, about 200 mg to about 10 g, about 300 mg to about 10 g, about 400 mg to about 10 g, about 500 mg to about 10 g, about 600 mg to about 10 g, about 700 mg to about 10 g, about 800 mg to about 10 g, about 900 mg to about 10 g, about 1 g to about 10 g, about 10 mg to about 5 g, about 10 mg to about 3 g, about 10 mg to about 1 g, about 10 mg to about 900 mg, about 10 mg to about 700 mg, about 10 mg to about 500 mg, or about 10 mg to about 300 mg). Suitable dosages per subject per day can be from about 0.01 mg to about 5 g.

In certain embodiments, the compounds or pharmaceutical compositions disclosed herein are formulated into a dosage form which is suitable for delivery to a subject in need thereof through a parenteral route (e.g. subcutaneous, intravenous, intramuscular, intraarterial, intrathecal, intracapsular, intraorbital, intra cardiac, intradermal, intraperitoneal, transtracheal, subcuticular, intraarticular, subcapsular, subarachnoid, intraspinal, intrasternal, and/or infusion) and a non-parenteral route (e.g. oral, enteral, buccal, nasal, intranasal, transmucosal, epidermal, transdermal, dermal, ophthalmic, pulmonary, sublingual, rectal, vaginal or topical). In certain examples, the compounds or pharmaceutical compositions disclosed herein are formulated into a dosage form which is suitable for delivery to a subject in need orally or enterally.

The suitable dosage forms include, without limitation, formulations for parenteral use such as injectable emulsions, solutions, and suspensions, formulations for oral use such as tablets, capsules, pills, dragees, powders, and granules, formulations for topical or transdermal use such as sprays, omintments, pastes, creams, lotions, gels, solutions, patches and inhalants, and formulations for intravaginal or intrarectal use such as suppositories. These formulations can be prepared by associating the compound with the suitable excipients at suitable conditions, in accordance with methods known in the art such as described by Remington: The Science and Practice of Pharmacy (Gennaro ed. 20th edition, Williams & Wilkins PA, USA) (2000).

The pharmaceutical compositions can be administered to a subject in any suitable route of administration, such as via oral, intravenous, intranasal, topical, intramuscular, intradermal, transdermal, or subcutaneous routes.

In certain embodiments, the compounds or pharmaceutical compositions provided herein can be administered concomitantly with the second active agent, such that combinatorial or even synergetic pharmaceutical effects can be achieved in the subject in need. For example, the compounds provided herein and the second active agent may be administered in a single pharmaceutical composition, or simultaneously in separate compositions, or sequentially in separate compositions. The second active agent that may be administered concomitantly with compounds of the present disclosure for cancer treatment include but not limited to: 5-fluorouracil, doxorubicin, daunorubicin, tamoxifen, leuprolide, goserelin, flutamide, nilutimide, finasteride, dexamethasone, lenalidomide aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, temozolomide, cyproterone, cytarabine, dacarbazine, dactinomycin, daunorubicin, dienestrol, diethylstilbestrol, docetaxel, doxorubicin adriamycine, epirubicin, estradiol, estramustine, etoposide, exemestane, filgrastim, fludarabine, fludrocortisone, fluorouracil, fluoxymesterone, flutamide, gemcitabine, genistein, goserelin, tamoxifen, teniposide, testosterone, titanocene dichloride, topotecan, trastuzumab, tretinoin, vinblastine, hydroxyurea, idarubicin, ifosfamide, imatinib, interferon, irinotecan, ironotecan, letrozole, leucovorin, pentostatin, plicamycin, porfimer, procarbazine, raltitrexed, rituximab, streptozocin, suramin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, thioguanine, thiotepa, titanocene dichloride, topotecan, trastuzumab, tretinoin, vinblastine, vincristine, vindesine, and vinorelbine.

In certain embodiments, a compound of the present disclosure may be administered concomitantly with non-chemical methods of cancer treatment. In certain embodiments, a compound of the present disclosure may be administered concomitantly with radiation therapy. In certain embodiments, a compound of the present disclosure may be conjointly administered with surgery, with thermoablation, with focused ultrasound therapy, with cryotherapy, or with any combination of these.

In certain embodiments, a compound of the present disclosure is administered concomitantly with a steroid, including but are not limited to, amcinonide, beclomethasone, betamethasone, budesonide, chloroprednisone, clobetasol, clocortolone, cloprednol, corticosterone, cortisone, sortiazol, desonide, desoximetasone, dexamethasone, diflorasone, diflucortolone, difuprednate, enoxolone, fluazacort, flumethasone, flunisolide, flucloronide, fluocinolone acetonide, fluocinonide, fluocorinbutyl, fluocortolone, fluorometholone, fluperolone acetate, fluprednidene acetate, fluprednisolone, flurandrenolide, fluticasone propionate, formocortal, halobetasol propionate, halcinonide, halometasone, hydrocortisone, loteprednol etabonate, maziprednone, medrysone, meprednisone, methylprednisolone, mometasone furoate, paramethasone, prednisolone, dexamethasone, and 25-diethylaminoacetate.

In certain embodiments, a compound of the present disclosure is administered concomitantly with an immunotherapeutic agent, including MDR modulators such as verapamil, rapamycin, mycophenylate mofetil, thalidomide, cyclophosomide, cyclosporine, and monoclonal antibodies.

EXAMPLES

The following are examples of tri-peptide epoxy ketones as disclosed herein, the synthesis thereof, the proteasome activity inhibitory property, anti-tumor activity property and aqueous solubility thereof.

Synthesis of the compounds provided herein is illustrated in the synthetic schemes in the examples below. These schemes are illustrative only and are not meant to limit other possible methods that can be used to prepare the compounds provided herein. Additionally, the steps in the schemes are for better illustration and can be changed as appropriate. The embodiments of the compounds in examples were synthesized overseas for the purposes of research and potentially submission to regulatory agencies.

For general experimental methods, $^1$H-NMR spectra were used to get information of structures of compounds. Liquid chromatography mass spectrometry (LC-MS) was taken using a quadrupole mass spectrometer system operating in positive electrospray ionization mode (ESI). Purity was checked by high performance liquid chromatography (HPLC) with UV detection. Preparative high performance liquid chromatography (Prep-HPLC) separation was used in purification when needed.

Example 1

Synthesis of Compound CX13-103

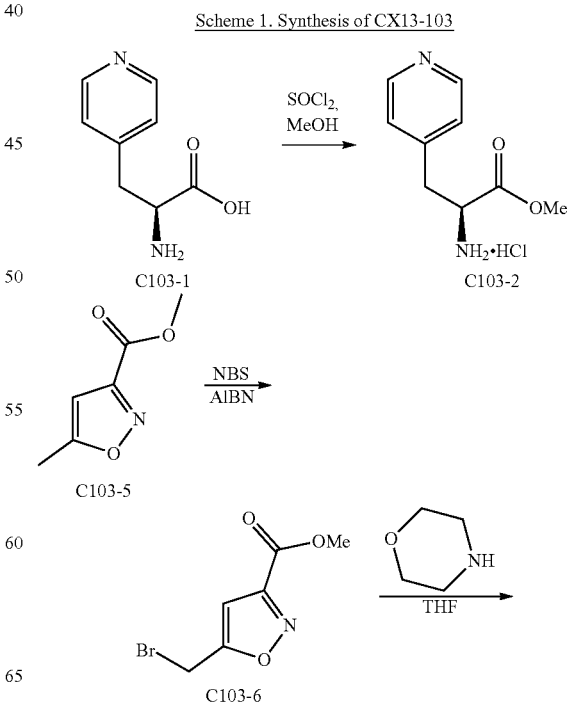

Scheme 1. Synthesis of CX13-103

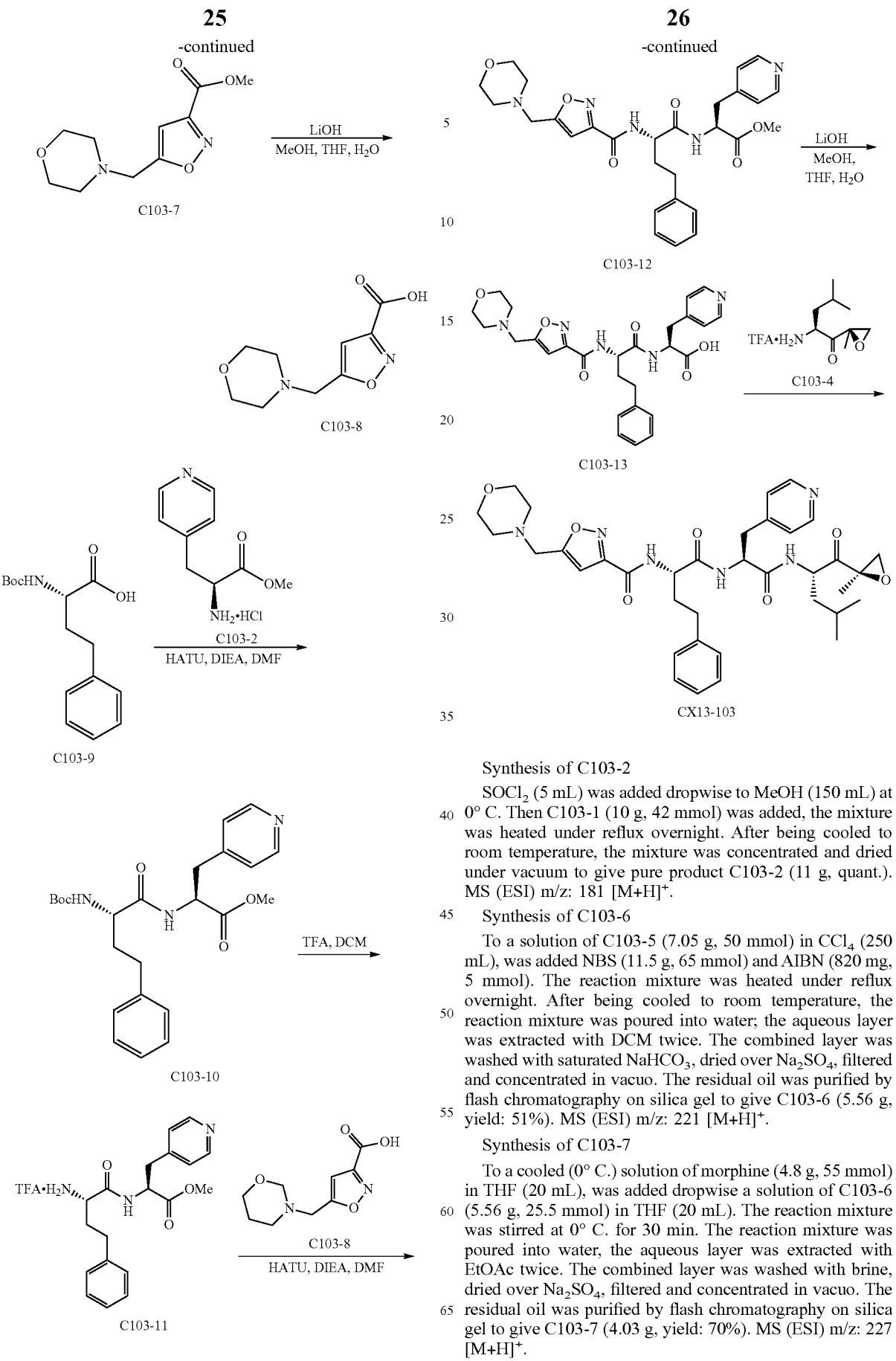

Synthesis of C103-2

SOCl$_2$ (5 mL) was added dropwise to MeOH (150 mL) at 0° C. Then C103-1 (10 g, 42 mmol) was added, the mixture was heated under reflux overnight. After being cooled to room temperature, the mixture was concentrated and dried under vacuum to give pure product C103-2 (11 g, quant.). MS (ESI) m/z: 181 [M+H]$^+$.

Synthesis of C103-6

To a solution of C103-5 (7.05 g, 50 mmol) in CCl$_4$ (250 mL), was added NBS (11.5 g, 65 mmol) and AIBN (820 mg, 5 mmol). The reaction mixture was heated under reflux overnight. After being cooled to room temperature, the reaction mixture was poured into water; the aqueous layer was extracted with DCM twice. The combined layer was washed with saturated NaHCO$_3$, dried over Na$_2$SO$_4$, filtered and concentrated in vacuo. The residual oil was purified by flash chromatography on silica gel to give C103-6 (5.56 g, yield: 51%). MS (ESI) m/z: 221 [M+H]$^+$.

Synthesis of C103-7

To a cooled (0° C.) solution of morphine (4.8 g, 55 mmol) in THF (20 mL), was added dropwise a solution of C103-6 (5.56 g, 25.5 mmol) in THF (20 mL). The reaction mixture was stirred at 0° C. for 30 min. The reaction mixture was poured into water, the aqueous layer was extracted with EtOAc twice. The combined layer was washed with brine, dried over Na$_2$SO$_4$, filtered and concentrated in vacuo. The residual oil was purified by flash chromatography on silica gel to give C103-7 (4.03 g, yield: 70%). MS (ESI) m/z: 227 [M+H]$^+$.

Synthesis of C103-8

To a cooled (0° C.) solution of C103-7 (4 g, 17.7 mmol) in THF (30 mL) and MeOH (30 mL) was added 2 N LiOH (13 mL, 26 mmol). The resulting mixture was stirred at room temperature for 1 hour. The pH was adjusted to 5 by addition of aqueous hydrochloride and the mixture was concentrated in vacuo. The residue was purified by chromatography to give C103-8 (2.65 g, yield: 71%). MS (ESI) m/z: 213 [M+H]$^+$.

Synthesis of C103-10

To a cooled (0° C.) solution of C103-9 (5.81 g, 20.8 mmol) in DMF (80 mL), was added HATU (8.3 g, 21.8 mmol) and DIEA (14.3 mL, 85 mmol). The mixture was stirred at 0° C. for 30 min. C103-2 (5.22 g, 20.8 mmol) was then added. The resulting solution was stirred at room temperature for 1 hour under nitrogen. The reaction mixture was poured into water and extracted with EtOAc twice. The combined organic layers were dried over Na$_2$SO$_4$, filtered and concentrated in vacuo. The residual oil was purified by prep-HPLC to give C103-10 (7.9 g, yield: 86%). MS (ESI) m/z: 442 [M+H]$^+$.

Synthesis of C103-11

To a solution of C103-10 (7.9 g, 17.9 mmol) in DCM (40 mL), was added TFA (10 mL) was added slowly at 0° C. Then the reaction mixture was allowed to stir at room temperature for 1 hour. Concentration under vacuum gave crude product, which was used for the next step without further purification. MS (ESI) m/z: 342 [M+H]$^+$.

Synthesis of C103-12

To a cooled (0° C.) solution of C103-8 (2.65 g, 12.5 mmol) in DMF (50 mL), was added HATU (6.18 g, 16.25 mmol) and DIEA (10 mL, 60 mmol). The mixture was stirred at 0° C. for 30 min. C103-11 was added. The resulting solution was stirred at room temperature for 1 hour under nitrogen. The reaction mixture was poured into water and extracted with EtOAc twice. The combined organic layers were dried over Na$_2$SO$_4$, filtered and concentrated in vacuo. The residual oil was purified by chromatography to give C103-12 (5.3 g, yield: 79%). MS (ESI) m/z: 536 [M+H]$^+$.

Synthesis of C103-13

To a cooled (0° C.) solution of C103-12 (5.3 g, 9.88 mmol) in THF (30 mL) and MeOH (30 mL) was added 2 N LiOH (7.5 mL, 16 mmol). The resulting mixture was stirred at room temperature for 1 hour. The pH was adjusted to 5 by addition of aqueous hydrochloride and concentrated in vacuo. The residue was purified by chromatography to give C103-13 (3.4 g, yield: 66%). MS (ESI) m/z: 522 [M+H]$^+$.

Synthesis of CX13-103

To a cooled (0° C.) solution of C103-13 (3.4 g, 6.53 mmol) in DMF (20 mL), was added HATU (3.23 g, 8.5 mmol) and DIEA (5 mL, 30 mmol). The mixture was stirred at 0° C. for 30 min. Then C103-4 (for synthesis of C103-4 see PCT patent application PCT/US2013/052143) was added. The resulting solution was stirred at room temperature for 1 hour under nitrogen. The reaction mixture was poured into water and extracted with EtOAc twice. The combined organic layers were dried over Na$_2$SO$_4$, filtered and concentrated in vacuo. The residual oil was purified by prep-HPLC to give CX13-103 (1.12 g, yield: 25%).

$^1$H-NMR (400 MHz, Methanol-d$_4$) δ 8.37 (d, 2H), 7.32 (d, 2H), 7.29-7.25 (m, 2H), 7.20-7.18 (m, 3H), 6.71 (s, 1H), 4.77 (dd, 1H), 4.56-4.51 (m, 2H), 3.82 (s, 2H), 3.74-3.72 (m, 4H), 3.25 (d, 1H), 3.23 (dd, 1H), 3.01 (dd, 1H), 2.95 (d, 1H), 2.70-2.50 (m, 6H), 2.20-1.95 (m, 2H), 1.80-1.60 (m, 1H), 1.52-1.20 (m, 5H), 0.91 (d, 3H), 0.89 (d, 3H); MS (ESI) m/z: 675 [M+H]$^+$; purity>95%.

Example 2

Synthesis of Compound CX13-104
Synthesis of Intermediate C104-7

Scheme 2: preparation of intermediate C104-7

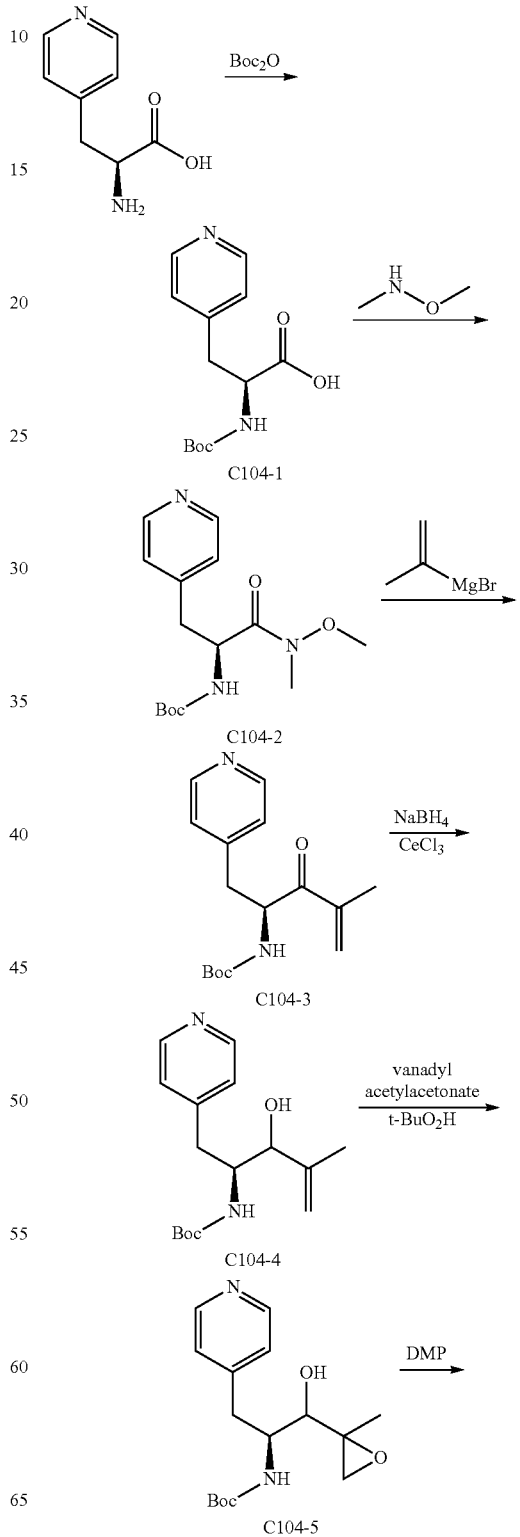

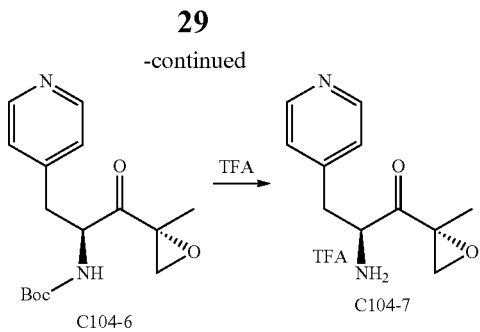

C104-6 → C104-7

Synthesis of C104-1

To 9.6 g (40 mmol) of L-3-(4-pyridyl)alanine. 2HCl were added 200 ml of a 1N aqueous sodium hydroxide solution and 200 ml of THF. While stirring, 20 ml of di-t-butyl dicarbonate was added dropwise and the mixture was stirred for 2 hours. To the resulting reaction mixture was added 300 ml of water and the resulting mixture was washed with ethyl acetate (2×200 ml). To the aqueous layer was added a 5% aqueous potassium hydrogen sulfate solution to adjust the pH of the mixture to about 4, and then, the mixture was extracted with n-butanol (4×200 ml). The organic layer was concentrated under reduced pressure. The solid was collected by filtration and dried to obtain 8.0 g of C104-1 as white solid. MS (ESI) m/z: 267.2 [M+H]$^+$.

Synthesis of C104-02

8.0 g (30 mmol) of C104-1 was dissolved in DMF (100 ml) at room temperature and cooled to 4° C. N, O-dimethylhydroxylamine hydrochloride (4.4 g, 45 mmol) was added, followed by HBTU (17 g, 45 mmol), HOBt (6.1 g, 45 mmol) and DIEA (12 ml, 90 mmol). The reaction was allowed to slowly warm to room temperature and stirred for overnight, after which it was diluted with EtOAc (300 ml) and washed successively with saturated sodium chloride (2×100 ml). The organic layer was dried with Na$_2$SO$_4$, filtered and concentrated under reduced pressure. Purification by column chromatography (DCM (1% TEA)) yielded the compound C104-2 as yellow oil (6.2 g, 66%). MS ESI) m/z: 310.3 [M+H]$^+$.

Synthesis of C104-3

The compound C104-2 (6.2 g, 20 mmol) was dissolved in THF (200 ml) and cooled to 0° C. (ice plus brine). Isopropenyl magnesium bromide (0.5 M in THF; 200 ml; 100 mmol) was added slowly over the course of 20 minutes. The reaction was stirred at 0° C. for 4 hours, after which it was poured slowly into a saturated aqueous ammonium chloride solution at 0° C. THF was removed under reduced pressure and the mixture was extracted with EtOAc (3×100 ml). The combined organic layers were then washed with saturated sodium bicarbonate, water and saturated aqueous sodium chloride. The organic layer was dried with Na$_2$SO$_4$, filtered and concentrated under reduced pressure. Purification by column chromatography (DCM (1% TEA)) gave the compound 3 as yellow oil (5.0 g, 86%). MS (ESI) m/z: 291.4 [M+H]$^+$.

Synthesis of C104-4

The compound C104-3 (5.0 g, 17 mmol) was dissolved in methanol (100 ml) and cooled to 0° C. Cerium (III) chloride heptahydrate (8.2 g, 22 mmol) was added, followed by addition of sodium borohydride (0.85 g, 22 mmol). The reaction mixture was stirred at 0° C. for 3 hours. The mixture was poured slowly into a saturated aqueous ammonium chloride solution (200 ml) at 0° C. and extracted with EtOAc (4×100 ml). The combined organic layers were then washed with saturated sodium bicarbonate, water and marine. The organic layer was dried with Na$_2$SO$_4$, filtered and concentrated under reduced pressure. Purification by column chromatography (DCM (1% TEA)) gave C104-4 as yellow solid (4.5 g, 90%). MS (ESI) m/z: 293.4 [M+H]$^+$.

Synthesis of C104-5

The compound C104-4 (4.5 g, 15 mmol) was dissolved in DCM (100 ml) and cooled to 0° C. Vanadyl acetylacetonate (0.12 g, 0.45 mmol) and then tert-Butyl hydroperoxide (5.0-6.0 M in decane; 12 ml, 60 mmol) were added. The reaction was allowed to warm slowly to room temperature for overnight. The mixtures were then washed with saturated sodium bicarbonate, water and marine. The organic layer was dried with Na$_2$SO$_4$, filtered and concentrated under reduced pressure to give C104-5 which was used next step without any purification. MS (ESI) m/z: 309.4 [M+H]$^+$.

Synthesis of C104-6

The compound C104-5 (4.5 g, 15 mmol) was dissolved in DCM (100 ml) and cooled to 0° C. Dess-Martin periodinane (13 g, 30 mmol) was added. The reaction was allowed to warm slowly to room temperature and after 24 hours. The mixture was then cooled to 4° C. and more Dess-Martin periodinane (6.4 g, 15 mmol) was added. The solution was allowed to warm slowly to room temperature. After 3 hours, the mixture was then filtered through Celite, the filtrate were then washed with saturated sodium hyposulfite, saturated sodium bicarbonate, water and marine. The organic layer was dried with Na$_2$SO$_4$, filtered and concentrated under reduced pressure. Purification by column chromatography (DCM (2% MeOH)) gave the compound C104-6 (0.35 g, 7.5%) as brown oil: $^1$H-NMR (CHLOROFORM-d) δ (ppm): 8.37-8.61 (m, 2H), 7.13 (d, J=5.2 Hz, 2H), 5.13 (br. s., 1H), 4.61 (d, 1H), 3.19 (d, 1H), 2.68-2.90 (m, 3H), 1.54 (s, 3H), 1.39 (s, 9H). MS (ESI) m/z: 307.4 [M+H]$^+$.

Synthesis of C104-7

The compound C104-6 (1.3 g, 4.2 mmol) was dissolved in DCM (50 ml) and cooled to 0° C. TFA (50 ml) was added. The reaction was allowed to warm slowly to room temperature. The mixture was concentrated under reduced pressure to give C104-7 as TFA salt. MS (ESI) m/z: 207.4 [M+H]$^+$.

Scheme 3: Preparation of CX13-104

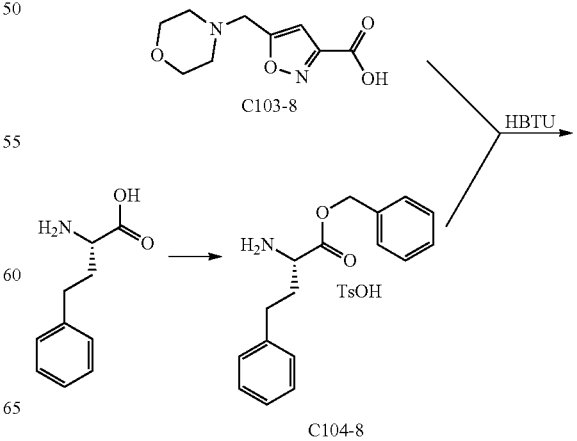

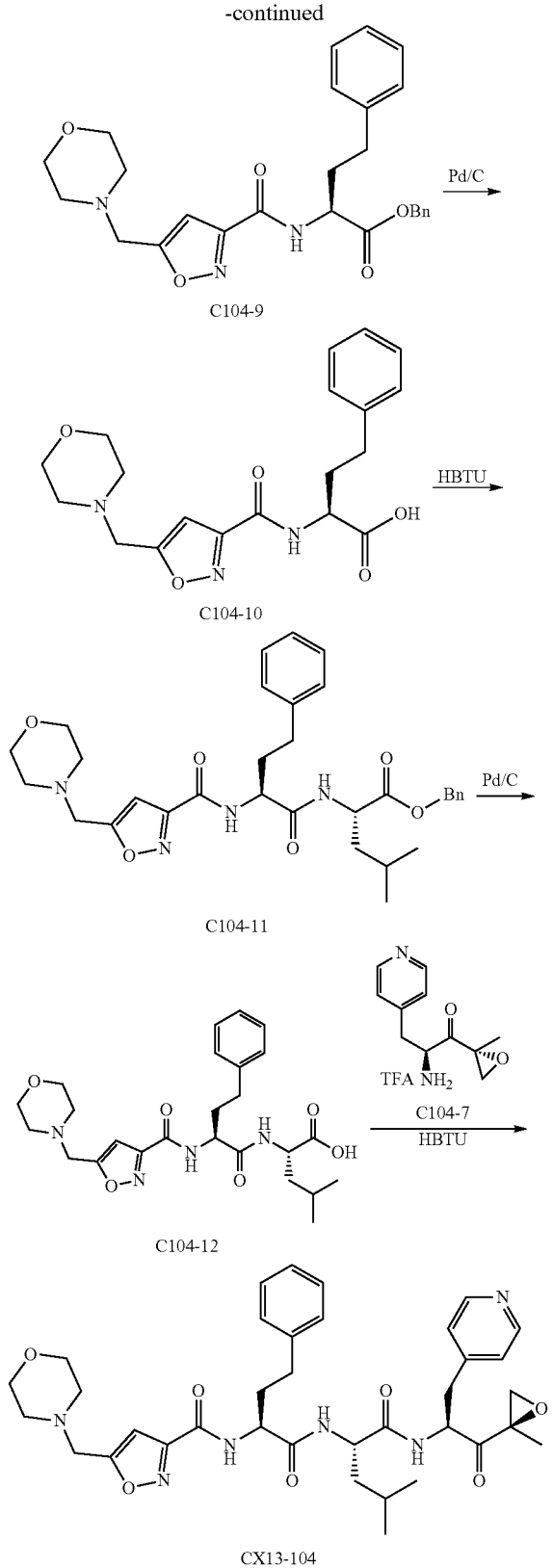

mL) was heated under reflux for 16 hours with a Dean-Stark trap. The benzene solution was washed with 5% aqueous NaHCO₃, brine, dried over MgSO₄, filtered, and evaporated to dryness under reduced pressure. The residue was crystallized in hexane to give C104-8 (9.0 g, 80%) as colorless needles. MS (ESI) m/z: 270.5 (M+H)⁺.

Synthesis of C104-9

To mixture of C103-8 (1.8 g, 8.5 mmol), C104-8 (3.7 g, 8.5 mmol) HBTU (4.8 g, 13 mmol) in DMF (20 mL) was added DIEA (3 mL) slowly via an addition funnel. The reaction was kept at the same temperature for 16 hours and then diluted with EtOAc (20 mL) and brine (20 mL). The layers were separated, and the aqueous layer was extracted with EtOAc (2×30 mL). The organic layers were combined and dried over Na₂SO₄. The solid was removed by filtration, and the volatiles were removed under reduced pressure and purified by silica gel chromatography (PE:EA=5:1) to give C104-9 (2.4 g, 61% yield) as white solid. MS (ESI) m/z: 463.5 (M+H)⁺.

Synthesis of C104-10

To C104-9 (2.4 g) in THF was added Pd/C (0.24 g) was stirred at H₂ atmosphere for 2 hours. The mixture was filtered and concentrated to give the product 104-5 which was used to the next step without purification. MS (ESI) m/z: 374.5 (M+H)⁺.

Synthesis of C104-11

To mixture of C104-10 (1.8 g, 8.5 mmol), (S)-benzyl 2-amino-4-methylpentanoate (1.9 g, 8.5 mmol) HBTU (4.8 g, 13 mmol) in DMF (20 mL) was added DIEA (3 mL) slowly via an addition funnel. The reaction was kept at room temperature for 16 hours and then diluted with EtOAc (20 mL) and brine (20 mL). The aqueous layer was extracted with EtOAc (2×30 mL). The organic layers were combined and dried over Na₂SO₄. The solid was removed by filtration, and the volatiles were removed under reduced pressure and purified by silica gel chromatography (PE:EA=5:1) to give 104-11 (2.4 g, 61% yield) as white solid. MS (ESI) m/z: 577.5 (M+H)⁺.

Synthesis of C104-12

To the C104-11 (2.4 g) in THF was added Pd/C (0.24 g). The mixture was stirred at H₂ atmosphere for 2 hours, filtered and concentrated to give the product C104-12 which was used to the next step without purification. MS (ESI) m/z: 487.5 (M+H)+

Synthesis of CX13-104

The mixture of C104-12 (0.40 g, 0.82 mmol), C104-7 (0.17 g, 0.82 mmol) HOBt (0.20 g 1.5 mmol), and HBTU (0.56 g, 1.5 mmol) in THF (5 mL) was kept at −5° C. and DIEA was added (1 mL). The reaction was kept at −5° C. for 0.5 hours and then diluted with EtOAc (10 mL) and brine (10 mL). The layers were separated, and the aqueous layer was extracted with EtOAc (2×5 mL). The organic layers were combined and dried over Na₂SO₄. The solid was removed by filtration, and the volatiles were removed under reduced pressure. The crude was purified by silica gel chromatography (DCM:MeOH=50:1) and Prep-HPLC to get the compound CX13-104 (50 mg 6.2%).

¹H-NMR (400 MHz, METHANOL-d₄) δ (ppm): 0.88-0.99 (m, 7H) 1.26-1.35 (m, 2H) 1.40-1.47 (m, 1H) 1.49-1.55 (m, 4H) 1.64 (d, J=6.45 Hz, 1H) 1.98-2.18 (m, 2H) 2.53-2.67 (m, 6H) 2.79 (dd, J=13.97, 9.94 Hz, 1H) 2.99 (d, J=4.84 Hz, 1H) 3.18 (dd, J=14.10, 3.63 Hz, 1H) 3.30 (s, 1H) 3.67-3.77 (m, 4H) 3.79-3.87 (m, 4H) 4.42 (dd, J=8.73, 6.31 Hz, 1H) 4.53 (dd, J=8.33, 5.64 Hz, 1H) 4.79 (dd, J=9.81, 3.63 Hz, 1H) 6.73 (s, 1H) 7.16-7.22 (m, 3H) 7.22-7.32 (m, 3H) 7.37 (d, J=5.91 Hz, 2H) 8.40 (d, J=5.37 Hz, 2H). MS (ESI) m/z: 675.5 (M+H)⁺.

Synthesis of C104-8

A mixture of (S)-2-amino-4-phenylbutanoic acid (5.0 g, 28 mmol), benzyl alcohol (6.0 g, 55 mmol), p-toluenesulfonic acid monohydrate (9.5 g, 55 mmol), and toluene (200

Example 3

Synthesis of Compound CX13-105

Scheme 4: Preparation of CX13-105

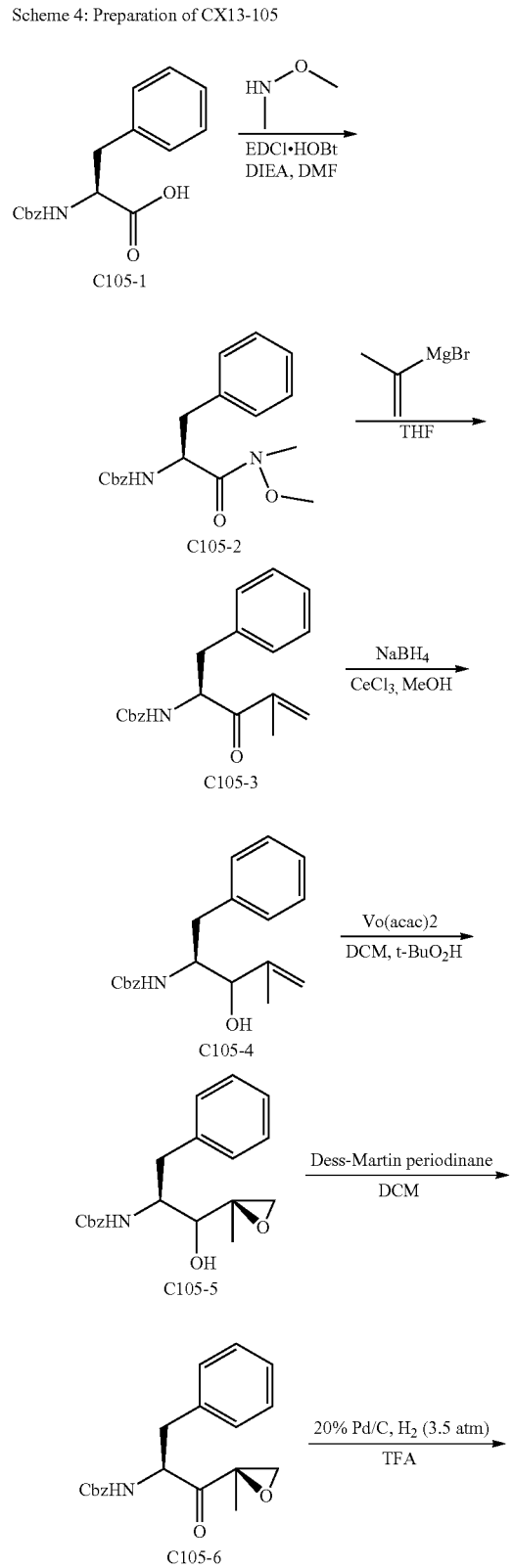

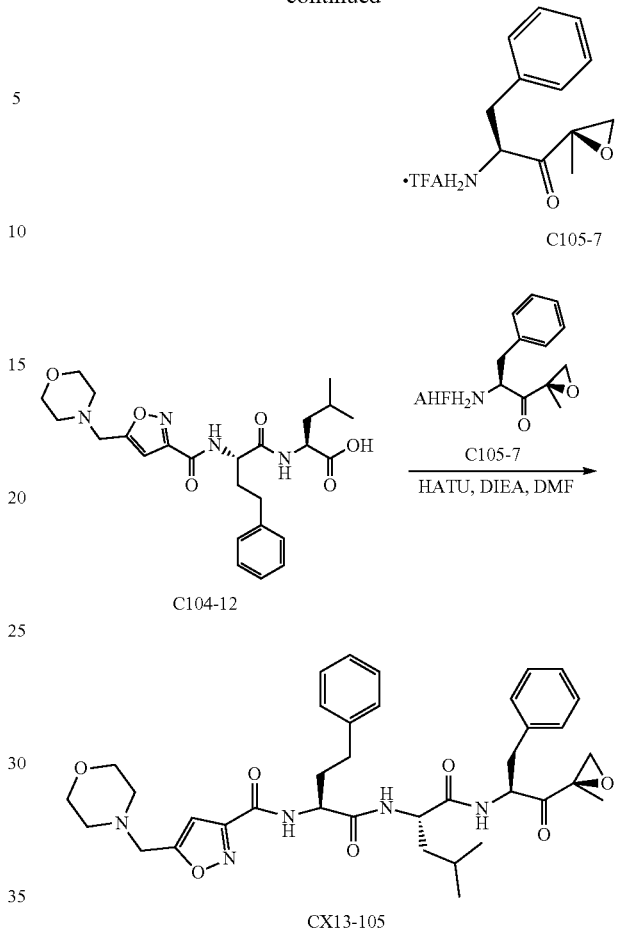

Synthesis of C105-2

To a cooled (0° C.) solution of C105-1 (10 g, 33.2 mmol), EDCI (8.3 g, 43.2 mmol), HOBt (7 g, 51.1 mmol) in DMF (40 mL) was added DIEA (14.3 mL, 85.2 mmol). The mixture was stirred at 0° C. for 30 min, then N, O-dimethyl-hydroxylamine hydrochloride (3.2 g, 33.2 mmol) was added. The resulting solution was stirred at room temperature for 1 hour under nitrogen. The reaction mixture was poured into water and extracted with EtOAc twice. The combined organic layers were dried over $Na_2SO_4$, filtered and concentrated in vacuo. The residual oil was purified by silica gel column to obtain the title compound C105-2 (8.0 g, yield: 72.7%). MS (ESI) m/z: 343 $[M+H]^+$.

Synthesis of C105-3

To a cooled (0° C.) solution of C105-2 (8 g, 23.2 mmol) in THF (50 mL) was added isopropenyl magnesium bromide (0.5 M in THF, 200 mL, 100 mmol) at 0° C. The resulting mixture was stirred at 0° C. for 3 hour. The reaction mixture was slowly poured into saturated $NH_4Cl$ solution. The pH of the solution was adjusted to 1.5 using concentrated HCl. The mixture was extracted with EtOAc. The combined organic layers were dried over $Na_2SO_4$, filtered and concentrated in vacuo. The residual oil was purified by silica gel column to obtain the title compound C105-3 (5.8 g, yield: 77%).

Synthesis of C105-4

To a cooled (0° C.) solution of C105-3 (5.8 g, 18 mmol) in MeOH (mL) and THF (20 mL) was added $NaBH_4$ (1.21 g, 31.8 mmol) and $CeCl_3 \cdot 7H_2O$ (11.8 g, 31.8 mmol) at 0° C. The resulting solution was stirred at 0° C. for 3 hours under nitrogen. Water (5 mL) was added to quench the reaction. After removal of all volatiles in vacuo, the residue was extracted with EtOAc. The combined organic layers were dried over Na$_2$SO$_4$, filtered and concentrated in vacuo. The residual oil was purified by silica gel column to obtain the title compound C105-4 (4.37 g, yield 72%). MS (ESI) m/z: 326 [M+H]$^+$.

Synthesis of C105-5.

To a cooled (0° C.) solution of C105-4 (4.37 g, 13.4 mmol) in DCM (20 mL) was added Vo(acac)$_2$ (344 mg, 1.3 mmol) and t-BuO$_2$H (5.5 M solution in decane, 2.6 mL, 14.3 mmol). The resulting mixture was stirred at room temperature for 2 hours. Water (5 mL) was added to quench the reaction. The resulting mixture was filtered through celite. The aqueous layer was extracted with DCM. The combined organic layers were washed with aqueous sodium bisulfite solution and brine, dried over Na$_2$SO$_4$. and concentrated in vacuo. The residual oil was used for the next step without further purification. MS (ESI) m/z: 342 [M+H]$^+$.

Synthesis of C105-6

To a cooled (0° C.) solution of C105-5 in DCM (20 mL) was added Dess-Martin periodinane (13 g, 32.5 mmol). The resulting mixture was stirred at room temperature for 1 hour. The resulting mixture was filtered through celite, the filtered cake was washed with DCM twice. The combined organic layers were washed with aqueous sodium bisulfite solution, saturated sodium bicarbonate brine, dried over Na$_2$SO$_4$. and concentrated in vacuo. The residual oil was purified by silica gel column to obtain the title compound C105-6 (2 g, yield 29%). MS (ESI) m/z: 340 [M+H]$^+$.

Synthesis of C105-7

To a cooled (0° C.) solution of C105-6 (2 g, 5.88 mmol) in MeOH (10 mL) and TFA (1 mL) was added palladium on charcoal (400 mg, 40% wt). The suspension was stirred at 0° C. for 6 hours under hydrogen atmosphere (3.5 atm) and then the reaction mixture was filtered through celite. The filtrate was concentrated in vacuo to afford the desired crude product, which was used for next step without further purification. MS (ESI) m/z: 206 [M+H]$^+$.

Synthesis of CX13-105

To a cooled (0° C.) solution of C104-7 (311 mg, 0.74 mmol), HATU (422 mg, 1.11 mmol) in DMF (5 mL), was added DIEA (0.62 mL, 3.7 mmol). The mixture was stirred at 0° C. for 30 min. A solution of C105-7 in DCM (2 mL) was added. The resulting solution was stirred at room temperature for 1 hour under nitrogen. The reaction mixture was poured into water and extracted with EtOAc twice. The combined organic layers were dried over Na$_2$SO$_4$, filtered and concentrated in vacuo. The residual oil was purified by prep-HPLC to give CX13-105 (70 mg, yield: 16%).

$^1$H-NMR (400 MHz, Methanol-d4) δ 7.32-7.09 (m, 10H), 6.72 (s, 1H), 4.76 (dd, 1H), 4.55 (dd, 1H), 4.46 (dd, 1H), 3.83 (s, 2H), 3.73-3.71 (m, 4H), 3.28 (d, 1H), 3.11 (dd, 1H), 2.94 (d, 1H), 2.76-2.60 (m, 3H), 2.59-2.55 (m, 4H), 2.11-2.02 (m, 2H), 1.65-1.61 (m, 1H), 1.54-1.51 (m, 2H), 1.45 (s, 3H), 0.94 (d, 3H), 0.90 (d, 3H); MS (ESI) m/z: 674 [M+H]$^+$. purity is >95%.

Example 4

Synthesis of Compound CX13-107

Scheme 5: Preparation of CX13-107

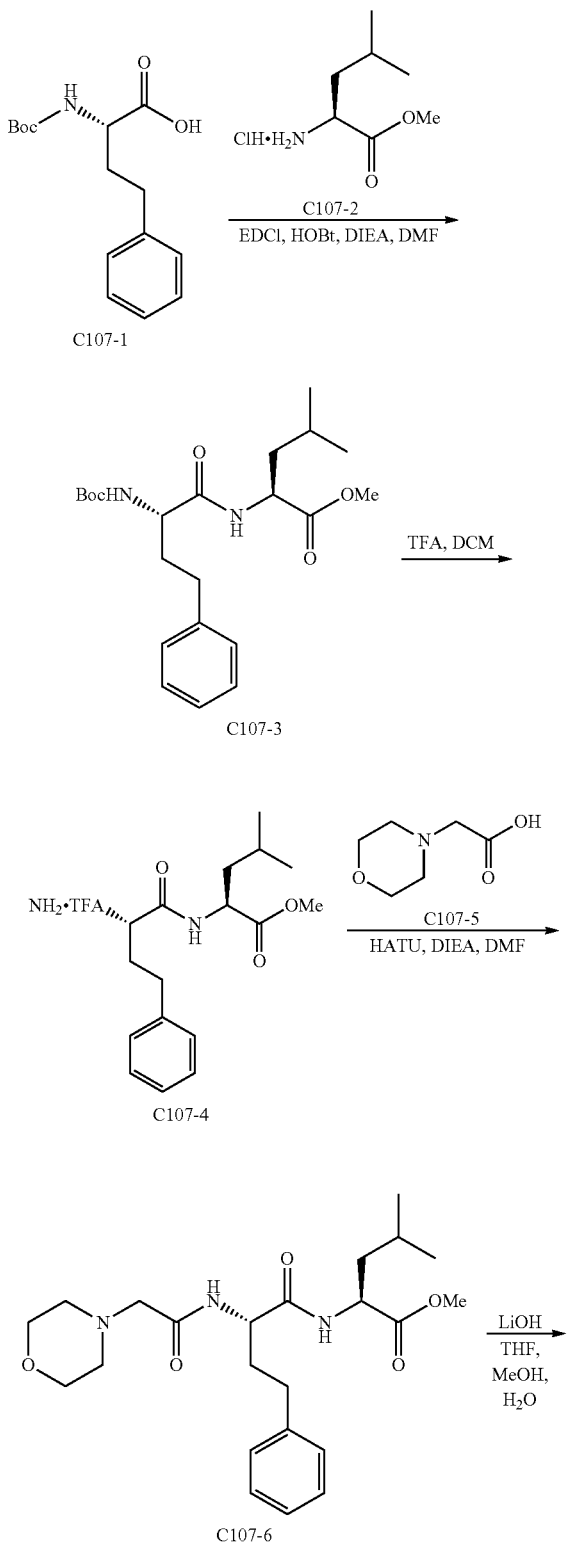

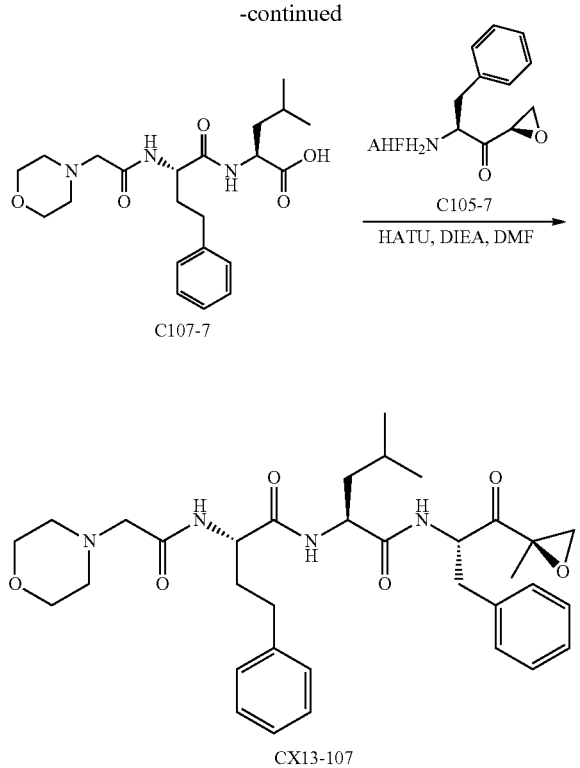

Synthesis of C107-7

To a cooled (0° C.) solution of C107-6 (4.5 g, 10.1 mmol) in THF (10 mL) and MeOH (10 mL) was added 2 N LiOH (10 mL, 20 mmol). The resulting mixture was stirred at room temperature for 1 hour. The pH was adjusted to 5 by addition of aqueous hydrochloride. The resulting solid was collected, washed with water and dried under vacuum to afford title compound (3.8 g, yield: 90%).

Synthesis of CX13-107.

To a solution of C107-7 (311 mg, 0.74 mmol), HATU (445 mg, 1.17 mmol), DIEA (0.5 mL, 2.2 mmol) in DMF (5 mL) stirred at 0° C. for 30 min was added C105-7. The resulting solution was stirred at room temperature for 1 hour under nitrogen. The reaction mixture was poured into water and extracted with EtOAc twice. The combined organic layers were dried over $Na_2SO_4$, filtered and concentrated in vacuo. The residual oil was purified by prep-HPLC to give (70 mg, yield: 16%).

$^1$H-NMR (400 MHz, Methanol-d4), δ 7.20-6.98 (m, 10H), 4.67 (dd, 1H), 4.36-4.31 (m, 2H), 3.68-3.62 (m, 4H), 3.21 (d, 1H), 3.02 (dd, 1H), 2.96 (dd, 2H), 2.85 (d, 1H), 2.63 (dd, 1H), 2.50-2.40 (m, 6H), 1.96-1.78 (m, 2H), 1.55-1.43 (m, 1H), 1.43-1.36 (m, 2H), 1.22 (s, 3H), 0.85 (d, 3H), 0.81 (d, 3H); MS (ESI) m/z: 607 [M+H]$^+$. purity is >95%.

Example 5

Synthesis of Compound CX13-130

Scheme 6: Preparation of CX13-130

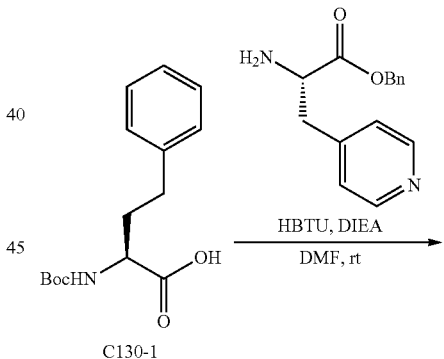

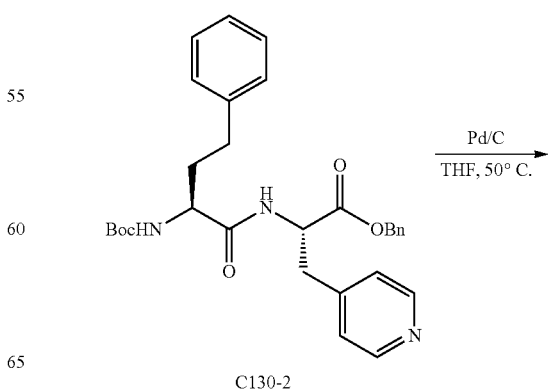

Synthesis of C107-3

To a cooled (0° C.) solution of C107-1 (10 g, 35.8 mmol) in DMF (40 mL), was added EDCI (8.5 g, 44.3 mmol), HOBt (7 g, 51.1 mmol), DIEA (14.3 mL, 85.2 mmol). The mixture was stirred at 0° C. for 30 min, then C107-2 was added (6.2 g, 34.1 mmol). The resulting solution was stirred at room temperature for 1 hour under nitrogen. The reaction mixture was poured into water and extracted with EtOAc twice. The combined organic layers were dried over $Na_2SO_4$, filtered and concentrated in vacuo. The residual oil was purified by flash chromatography on silica gel to give C107-3 (13.5 g, yield 97.8%). MS (ESI) m/z: 351 [M+H−55]$^+$.

Synthesis of C107-4.

To a cooled (0° C.) solution of C107-3 (13.5 g, 33.3 mmol) in DCM (50 mL), was added TFA (20 mL) was added. The reaction mixture was stirred at room temperature for 1 h. Concentration under vacuum gave crude product, which was used for the next step without further purification. MS (ESI) m/z: 307 [M+H]$^+$.

Synthesis of C107-6

To a cooled (0° C.) solution of C107-5 (1.8 g, 12.4 mmol) in DMF (20 mL), was added HATU (5.8 g, 15.3 mmol), DIEA (10 mL, 60 mmol). The mixture was stirred at 0° C. for 30 min. Then C107-4 was added. The resulting solution was stirred at room temperature for 1 hour under nitrogen. The reaction mixture was poured into water and extracted with EtOAc twice. The combined organic layers were dried over $Na_2SO_4$, filtered and concentrated in vacuo. The residual oil was purified by flash chromatography on silica gel to give C107-6 (4.5 g, yield: 88%). MS (ESI) m/z: 434 [M+H]$^+$.

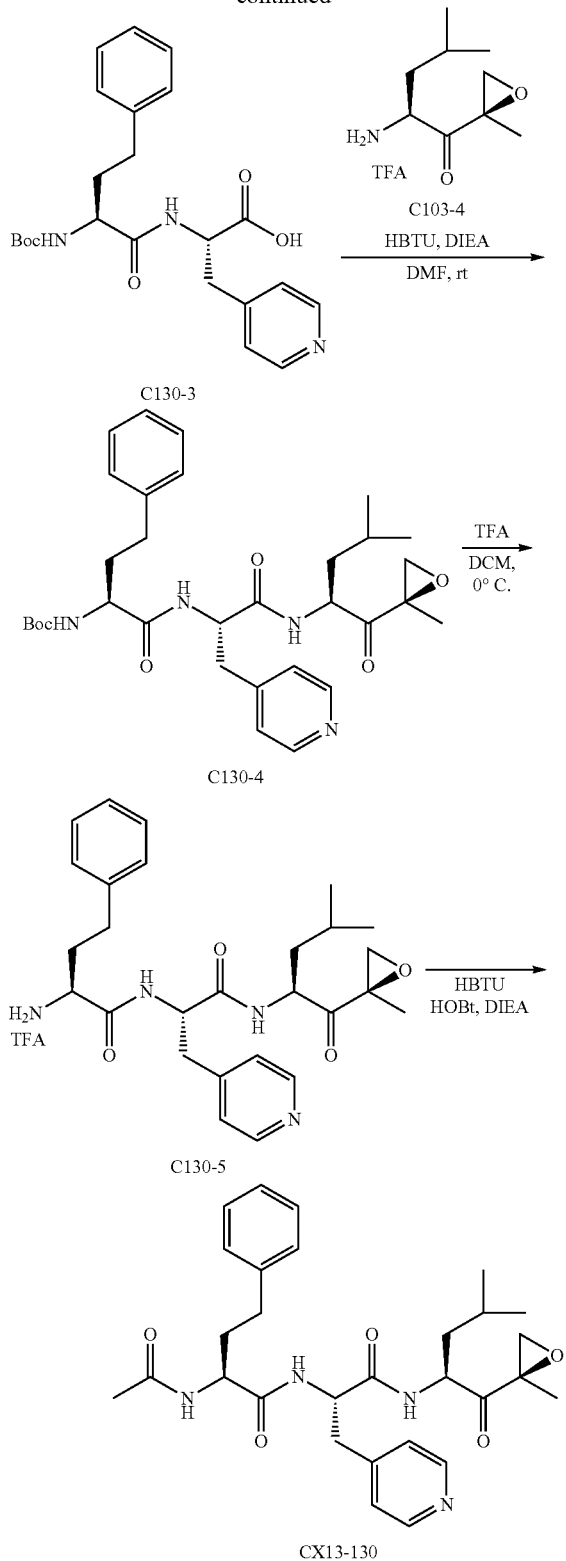

kept at the same temperature for 16 hours and then diluted with EtOAc (80 mL) and brine (40 mL). The layers were separated, and the aqueous layer was extracted with EtOAc (2×40 mL). The organic layers were combined and dried over $Na_2SO_4$. The solid was removed by filtration, and the volatiles were removed under reduced pressure and purified by silica gel chromatography (PE:EA=10:1) to give the compound 130-2 (2.0 g, 72% yield) as a white solid. MS (ESI) m/z: 518.3 $(M+H)^+$.

Synthesis of C130-3

To the compound C130-2 (1.5 g, 2.9 mmol) in THF (25 mL) was added Pd/C (0.15 g, 10% in carbon) and the mixture was stirred under $H_2$ atmosphere for 16 h at 50° C. The mixture was filtered and concentrated to give the compound C130-3 (1100 mg, 90% yield) which was used to the next step without purification. MS (ESI) m/z: 428.3 $(M+H)^+$.

Synthesis of C130-4

To mixture of compound C130-3 (1.1 g, 2.6 mmol) in DMF (15 mL) was added (S)-2-amino-4-methyl-1-((R)-2-methyloxiran-2-yl)pentan-1-one (0.69 g, 2.6 mmol), HBTU (1.5 g, 3.9 mmol), HOBt (0.53 g, 3.9 mmol) and DIEA (2 mL). The reaction was stirred at room temperature for 16 hours and then diluted with EtOAc (60 mL) and brine (20 mL). The layers were separated, and the aqueous layer was extracted with EtOAc (2×30 mL). The organic layers were combined and dried over $Na_2SO_4$. The solid was removed by filtration, and the volatiles were removed under reduced pressure and purified by silica gel chromatography (PE:EA=1:1) to give the compound C130-4 (510 mg, 34% yield) as white solid. MS (ESI) m/z: 581.4 $(M+H)^+$.

Synthesis of C130-5

To mixture of compound C130-4 (510 mg, 0.88 mmol) in DCM (10 mL) was added TFA (4 mL) at 0° C. The reaction was kept at 0° C. for 2 hours and the volatiles were removed under reduced pressure to give the compound 130-5 (500 mg, 100% yield) as a white solid. MS (ESI) m/z: 481.4 $(M+H)^+$.

Synthesis of CX13-130

To mixture of compound C130-5 (110 mg, 0.19 mmol) in DMF (2 mL) was added acetic acid (14 mg, 0.23 mmol), HBTU (108 mg, 0.29 mmol), HOBt (39 mg, 0.29 mmol) and DIEA (0.2 mL) at room temperature. The reaction was kept at room temperature for 16 hours and then diluted with EtOAc (40 mL) and brine (10 mL). The layers were separated, and the aqueous layer was extracted with EtOAc (2×20 mL). The organic layers were combined and dried over $Na_2SO_4$. The solid was removed by filtration, and the volatiles were removed under reduced pressure and purified by silica gel chromatography (DCM:MeOH=40:1) and Prep-HPLC to get CX13-130 (25 mg, 21%) as a white solid. $^1$H-NMR (400 MHz, CDCl3) δ 8.50 (s, 2H), 7.38-7.25 (m, 4H), 7.21 (t, J=7.3 Hz, 1H), 7.17 (t, J=10.3 Hz, 3H), 6.83 (d, J=7.6 Hz, 1H), 6.19 (d, J=7.3 Hz, 1H), 4.81 (dd, J=13.9, 7.7 Hz, 1H), 4.57 (t, J=7.6 Hz, 1H), 4.38 (dd, J=14.0, 7.3 Hz, 1H), 3.25 (dd, J=16.9, 5.1 Hz, 2H), 3.05 (dd, J=14.2, 8.2 Hz, 1H), 2.92 (d, J=4.9 Hz, 1H), 2.65 (dd, J=14.7, 6.3 Hz, 2H), 2.13 (dd, J=14.1, 7.5 Hz, 2H), 1.93 (s, 4H), 1.67-1.47 (m, 5H), 1.30 (dd, J=16.6, 6.8 Hz, 2H), 0.92 (dd, J=8.9, 6.5 Hz, 6H). MS (ESI) m/z: 523.7 $(M+H)^+$.

Synthesis of C130-2

To mixture of compound C130-1 (1.5 g, 5.4 mmol) in DMF (30 mL) was added (S)-benzyl 2-amino-3-(pyridin-4-yl)propanoate (1.38 g, 5.4 mmol), HBTU (3.1 g, 8.1 mmol) and DIEA (4 mL) at room temperature. The reaction was

Example 6

Synthesis of Compound CX13-133

Scheme 7: Preparation of CX13-133

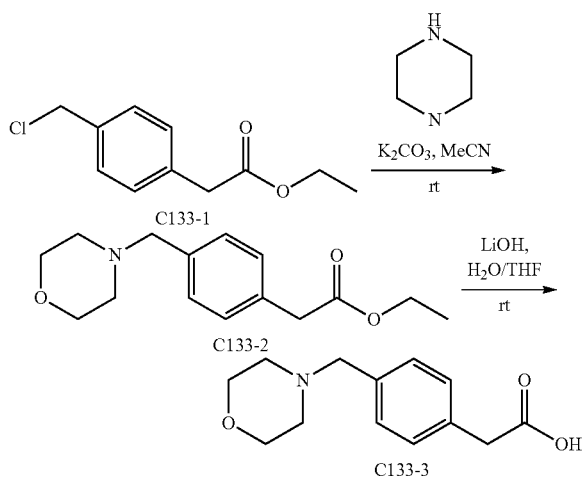

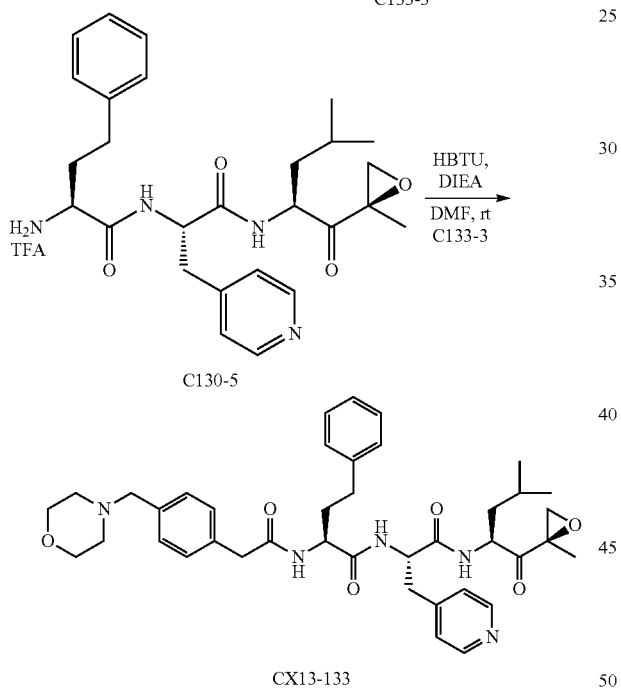

Synthesis of C133-2

To a solution of morpholine (456 mg, 5.6 mmol) in MeCN (20 mL) was added K$_2$CO$_3$ (841 mg, 6.1 mmol) and C133-1 (1 g, 4.7 mmol) at room temperature. The mixture was stirred at 50° C. for 4 hours. The solid was removed by filtration, and the volatiles were removed under reduced pressure and purified by silica gel chromatography (PE:EA=4:1) to give the compound C133-2 (1.0 g, 81% yield) as a colorless oil. MS (ESI) m/z: 264.2 (M+H)$^+$.

Synthesis of C133-3

To a solution of compound C133-2 (1000 mg, 3.8 mmol) in THF (16 mL) and water (8 mL) was added LiOH.H$_2$O (477 mg, 11.4 mmol) at room temperature. The mixture was stirred at room temperature for 16 hours. Then the mixture was acidified to PH=5, concentrated, and purified by chromatography to give C133-3 (750 mg, 84% yield) as a white solid. MS (ESI) m/z: 236.2 (M+H)$^+$.

Synthesis of CX13-133

To mixture of C130-5 (110 mg, 0.19 mmol) in DMF (2 mL) was added 133-3 (54 mg, 0.23 mmol), HBTU (108 mg, 0.29 mmol), HOBt (39 mg, 0.29 mmol) and DIEA (0.2 mL) at room temperature. The reaction was kept at room temperature for 16 hours and then diluted with EtOAc (40 mL) and brine (10 mL). The layers were separated, and the aqueous layer was extracted with EtOAc (2×20 mL). The organic layers were combined and dried over Na$_2$SO$_4$. The solid was removed by filtration, and the volatiles were removed under reduced pressure and purified by silica gel chromatography (DCM:MeOH=40:1) and Prep-HPLC to get CX13-133 (55 mg, 41%) as a white solid.

$^1$H NMR (400 MHz, METHANOL-d4) δ ppm 0.86-1.01 (dd, 6H) 1.43 (t, J=6.98 Hz, 4H) 1.47-1.64 (m, 1H) 1.88-1.96 (m, 2H) 2.56 (m, 6H) 2.96 (m, 9.94 Hz, 2H) 3.18 (dd, J=9.94 Hz, 1H) 3.22 (d, J=5.2 Hz, 1H) 3.4-3.6 (m, 4H) 3.6-3.66 (m, 4H) 4.26-4.28 (m, 1H) 4.46 (d, J=4.84 1 H) 4.71-4.75 (m, 1H) 7.06 (d, J=5.2 Hz 1H) 7.16-7.20 (m, 1H) 7.20-7.24 (m, 2H) 7.26-7.32 (m, 2H) 7.34 (s, 4H) 8.36-8.38 (m, 2H). MS (ESI) m/z: 698.4 (M+H)$^+$.

Example 7

Synthesis of Compound CX13-135

Scheme 8: Preparation of CX13-135

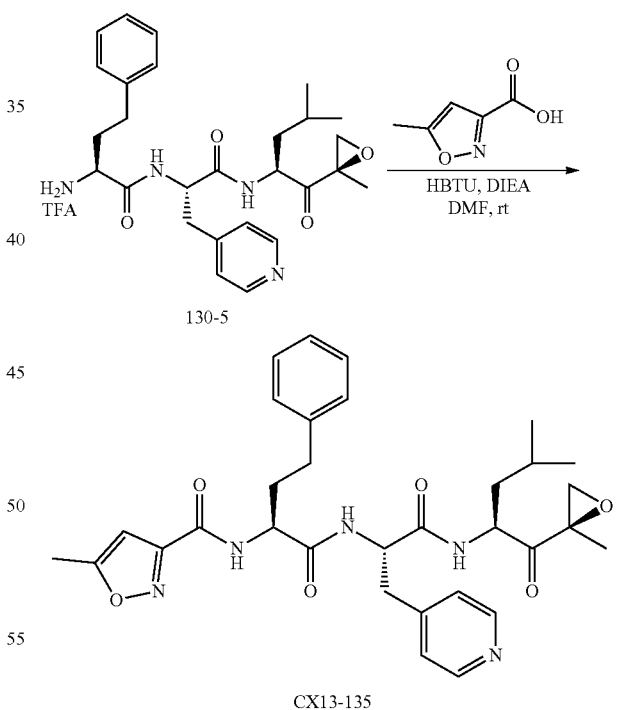

To mixture of compound C130-5 (110 mg, 0.19 mmol) in DMF (2 mL) was added 5-methylisoxazole-3-carboxylic acid (40 mg, 0.23 mmol), HBTU (108 mg, 0.29 mmol), HOBt (39 mg, 0.29 mmol) and DIEA (0.2 mL) at room temperature. The reaction was kept at room temperature for 16 hours, then diluted with EtOAc (40 mL) and brine (10 mL). The layers were separated, and the aqueous layer was extracted with EtOAc (2×20 mL). The organic layers were combined and dried over Na$_2$SO$_4$. The solid was removed by filtration, and the volatiles were removed under reduced pressure and purified by silica gel chromatography (DCM:MeOH=40:1) and Prep-HPLC to get CX13-135 (18 mg, 16%) as a white solid.

$^1$H NMR (400 MHz, CDCl$_3$) δ 8.38 (s, 2H), 7.35 (d, J=7.9 Hz, 1H), 7.33-7.23 (m, 3H), 7.20 (t, J=7.3 Hz, 1H), 7.16-7.08 (m, 4H), 6.96 (d, J=8.0 Hz, 1H), 6.68 (d, J=7.7 Hz, 1H), 6.43 (d, J=0.7 Hz, 1H), 4.75 (dd, J=14.2, 7.5 Hz, 1H), 4.62-4.43 (m, 2H), 3.26 (d, J=4.9 Hz, 1H), 3.12 (dd, J=14.1, 6.2 Hz, 1H), 2.98 (dd, J=14.1, 7.5 Hz, 1H), 2.91 (d, J=5.0 Hz, 1H), 2.67 (t, J=7.8 Hz, 2H), 2.58-2.45 (m, 3H), 2.21 (dt, J=14.0, 7.7 Hz, 2H), 2.04 (td, J=15.6, 7.9 Hz, 1H), 1.64-1.42 (m, 5H), 1.37-1.16 (m, 2H), 0.89 (dd, J=13.1, 6.3 Hz, 6H). MS (ESI) m/z: 590.4 (M+H)$^+$.

Example 8

Synthesis of Compound CX13-137

Scheme 9: Preparation of CX13-137

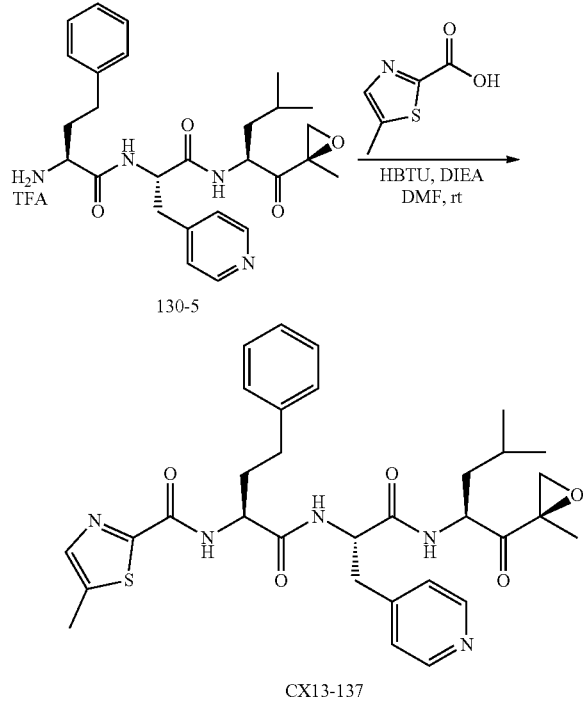

To mixture of C130-5 (110 mg, 0.19 mmol) in DMF (2 mL) was added 5-methylthiazole-2-carboxylic acid (41 mg, 0.23 mmol), HBTU (108 mg, 0.29 mmol), HOBt (39 mg, 0.29 mmol) and DIEA (0.2 mL) at room temperature. The reaction was kept at room temperature for 16 hours and then diluted with EtOAc (40 mL) and brine (10 mL). The layers were separated, and the aqueous layer was extracted with EtOAc (2×20 mL). The organic layers were combined and dried over Na$_2$SO$_4$. The solid was removed by filtration, and the volatiles were removed under reduced pressure and purified by chromatography to get CX13-137 (36 mg, 31%) as a white solid.

$^1$H NMR (400 MHz, CDCl$_3$) δ 8.32 (d, J=5.6 Hz, 2H), 8.05 (s, 1H), 7.41 (dd, J=29.1, 17.6 Hz, 3H), 7.20 (dt, J=24.4, 7.1 Hz, 3H), 7.13-7.02 (m, 3H), 4.79 (dd, J=13.9, 8.0 Hz, 1H), 4.71-4.49 (m, 2H), 3.25 (d, J=4.9 Hz, 1H), 3.11 (dd, J=13.7, 5.3 Hz, 1H), 2.98-2.81 (m, 2H), 2.76 (s, 3H), 2.63 (t, J=7.7 Hz, 2H), 2.23-1.93 (m, 2H), 1.76-1.41 (m, 5H), 1.30 (ddd, J=14.3, 8.6, 4.5 Hz, 2H), 0.87 (dd, J=17.5, 6.4 Hz, 6H). MS (ESI) m/z: 606.3 (M+H)$^+$.

Example 9

Synthesis of Compound CX13-600

Scheme 10: Preparation of CX13-600

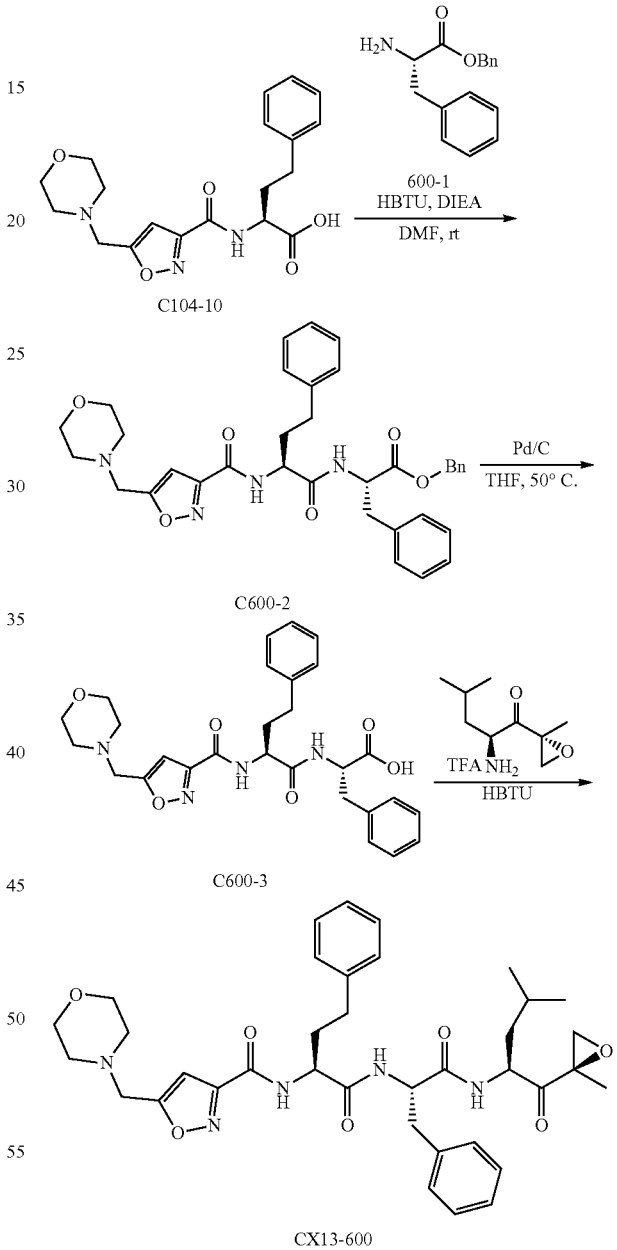

Synthesis of C600-2

To mixture of C104-10 (2.0 g, 5.4 mmol) in DMF (30 mL) was added C600-1 (1.38 g, 5.4 mmol), HBTU (3.1 g, 8.1 mmol) and DIEA (4 mL) at room temperature. The reaction was kept at room temperature for 16 hours and then diluted with EtOAc (80 mL) and brine (40 mL). The layers were separated, and the aqueous layer was extracted with EtOAc (2×40 mL). The organic layers were combined and dried over Na$_2$SO$_4$. The solid was removed by filtration, and the volatiles were removed under reduced pressure and purified by silica gel chromatography (PE:EA=10:1) to give the compound C600-2 (1.8 g, 69% yield) as a white solid. MS (ESI) m/z: 611.7 (M+H)$^+$.

Synthesis of C600-3

To the compound C600-2 (1.77 g, 2.9 mmol) in THF (20 mL) was added Pd/C (0.15 g, 10% in carbon) and the mixture was stirred under H$_2$ atmosphere for 16 hours at 50° C. The mixture was filtered and concentrated to give the compound C600-3 (1.35 g, 90% yield) which was used to the next step without purification. MS (ESI) m/z: 521.3 (M+H)$^+$.

Synthesis of CX13-600

To a cold (−5° C.) mixture of C600-3 (150 mg, 0.29 mmol), C103-4 (78 mg, 0.29 mmol), HOBt (60 g, 0.51 mmol) and HBTU (165 g, 0.51 mmol) in DMF (4 mL) was added DIEA (0.2 mL). The reaction was kept at −5° C. for 1 hour and then diluted with EtOAc (10 mL) and brine (10 mL). The layers were separated, and the aqueous layer was extracted with EtOAc (2×10 mL). The organic layers were combined and dried over Na$_2$SO$_4$. The solid was removed by filtration, and the volatiles were removed under reduced pressure. The crude was purified by chromatography to get the compound CX13-600 (98 mg, 51.0%).

$^1$H-NMR (400 MHz, CDCl$_3$) δ 7.30 (br. s, 1H), 7.13-7.28 (m, 10H), 6.57-6.73 (m, 2H), 6.16 (br. s., 1H), 4.66 (d, J=7.25 Hz, 1H), 4.47-4.59 (m, 2H), 3.59-3.89 (br, 6H), 3.25 (d, J=5.10 Hz, 1H), 3.05 (dd, J=6.72, 3.49 Hz, 2H), 2.90 (d, J=4.84 Hz, 1H), 2.48-2.74 (m, 6H), 2.18-2.29 (m, 1H), 1.96-2.11 (m, 1H), 1.55 (s, 3H), 1.41-1.54 (m, 2H), 1.20 (t, J=9.94 Hz, 1H), 0.88 (dd, J=13.30, 5.78 Hz, 6H). MS (ESI) m/z: 674.3 (M+H)$^+$.

Example 10

Synthesis of CX13-601

Scheme 11: Preparation of CX13-601

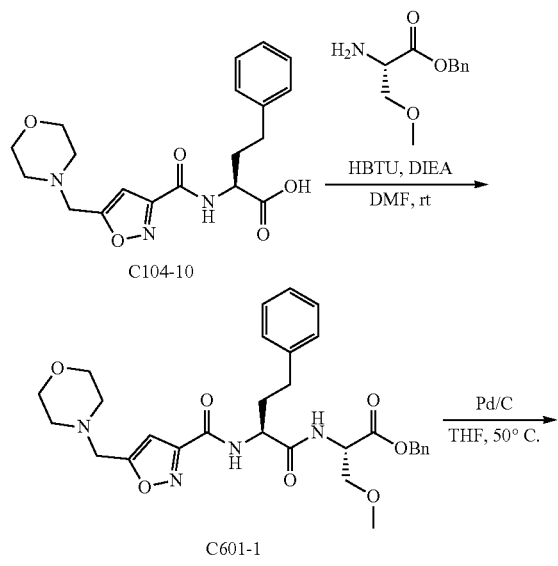

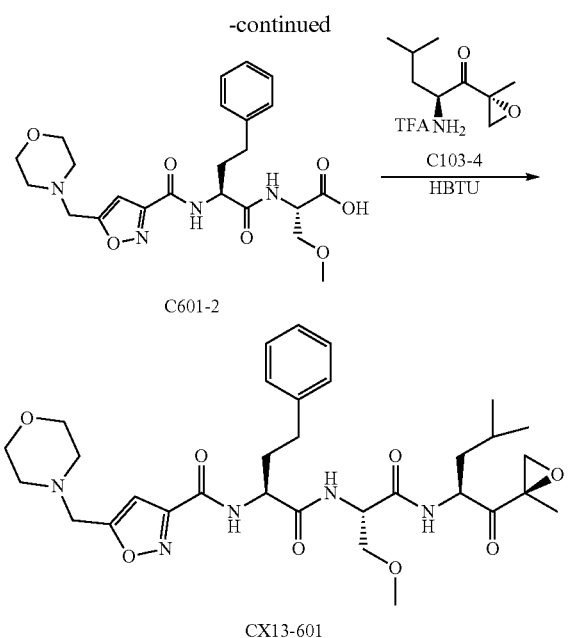

Synthesis of C601-1

To mixture of C104-10 (500 mg, 1.3 mmol), (S)-benzyl 2-amino-4-methylpentanoate (335 mg, 1.6 mmol) TBTU (516 mg, 13 mmol) in DMF (50 mL) was added DIEA (0.3 mL) slowly via an addition funnel at room temperature. The reaction was kept at room temperature for 16 hours and then diluted with EtOAc (10 mL) and brine (10 mL). The layers were separated, and the aqueous layer was extracted with EtOAc (2×10 mL). The organic layers were combined and dried over Na$_2$SO$_4$. The solid was removed by filtration, and the volatiles were removed under reduced pressure and purified by silica gel chromatography (PE:EA=5:1) to give 601-1 (660 g, 87% yield) as white solid. MS (ESI) m/z: 565.2 (M+H)$^+$.

Synthesis of C601-2

To C601-1 (660 mg) in THF was added Pd/C (66 mg) and the mixture was stirred at H$_2$ atmosphere for 12 hours. The mixture was filtered and concentrated to give the product C601-2 which was used to the next step without purification. MS (ESI) m/z: 475.2 (M+H)$^+$.

Synthesis of CX13-601

To a cold (−5° C.) mixture of C601-2 (150 mg, 0.32 mmol), C103-4 (102 mg, 0.38 mmol), HOBt (51 g, 0.51 mmol), and HBTU (144 g, 0.51 mmol) in DMF (5 mL) was added DIEA (0.2 mL). The reaction was kept at −5° C. for 1 hour and then diluted with EtOAc (15 mL) and brine (15 mL). The layers were separated, and the aqueous layer was extracted with EtOAc (2×10 mL). The organic layers were combined and dried over Na$_2$SO$_4$. The solid was removed by filtration, and the volatiles were removed under reduced pressure. The crude was purified by chromatography to get the compound CX13-601 (70 mg, 35.3%).

$^1$H-NMR (400 MHz, CDCl$_3$) δ 7.33 (d, J=9.94 Hz, 2H), 7.17-7.26 (m, 3H), 6.89 (d, J=8.33 Hz, 1H), 6.74 (d, J=6.72 Hz, 1H), 6.66 (s, 1H), 4.58-4.67 (m, 2H), 4.50 (m, 1H), 3.69-3.83 (m, 7H), 3.35-3.47 (m, 4H), 3.30 (d, J=4.84 Hz, 1H), 2.92 (d, J=4.84 Hz, 1H), 2.76 (t, J=7.92 Hz, 2H), 2.49-2.60 (m, 4H), 2.24-2.37 (m, 1H), 2.12 (m, 1H), 1.53-1.67 (m, 2H), 1.49-1.58 (m, 4H) 0.89-0.98 (m, 6H) MS (ESI) m/z: 628.3 (M+H)$^+$.

Example 11

Synthesis of Compound CX13-603

Scheme 12: Preparation of CX13-603

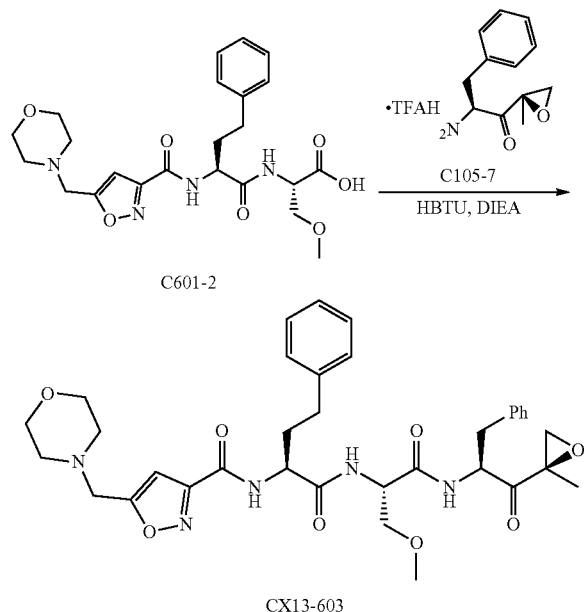

To a cold (−5° C.) mixture of C601-2 (200 mg, 0.42 mmol), C105-7 0.17 g, 0.82 mmol), HOBt (69 mg, 0.51 mmol), and HBTU (191 mg, 0.51 mmol) in DMF (5 mL) was added DIEA (0.5 mL). The reaction was kept at −5° C. for 1 hour and then diluted with EtOAc (10 mL) and brine (10 mL). The layers were separated, and the aqueous layer was extracted with EtOAc (2×10 mL). The organic layers were combined and dried over $Na_2SO_4$. The solid was removed by filtration, and the volatiles were removed under reduced pressure. The crude was purified by chromatography to get the compound CX13-603 (60 mg, 21.6%).

$^1$H-NMR (400 MHz, $CDCl_3$) δ 7.35-7.23 (m, 7H), 7.22-7.13 (m, 4H), 7.02 (d, J=7.6 Hz, 1H), 6.81 (b, 1H), 6.64 (d, J=6.5 Hz, 1H), 4.81 (td, J=7.6, 4.9 Hz, 1H), 4.58 (dd, J=13.6, 7.9 Hz, 1H), 4.42 (td, J=7.3, 3.9 Hz, 1H), 3.85 (b, 5H), 3.74 (dd, J=9.1, 3.8 Hz, 1H), 3.35 (s, 3H), 3.32 (d, J=5.1 Hz, 1H), 3.17 (dd, J=14.0, 4.9 Hz, 1H), 2.95 (d, J=4.9 Hz, 1H), 2.86 (dd, J=14.0, 7.7 Hz, 1H), 2.71 (t, J=7.8 Hz, 2H), 2.63 (b, 4H), 2.23 (m, 1H), 2.07 (m, 1H), 1.54 (s, 3H). MS (ESI) m/z: 662.3 (M+H)$^+$.

Example 12

Synthesis of Compound CX13-605

Scheme 13: Preparation of CX13-605

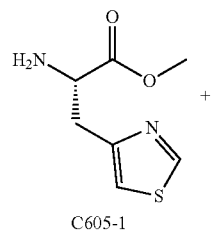

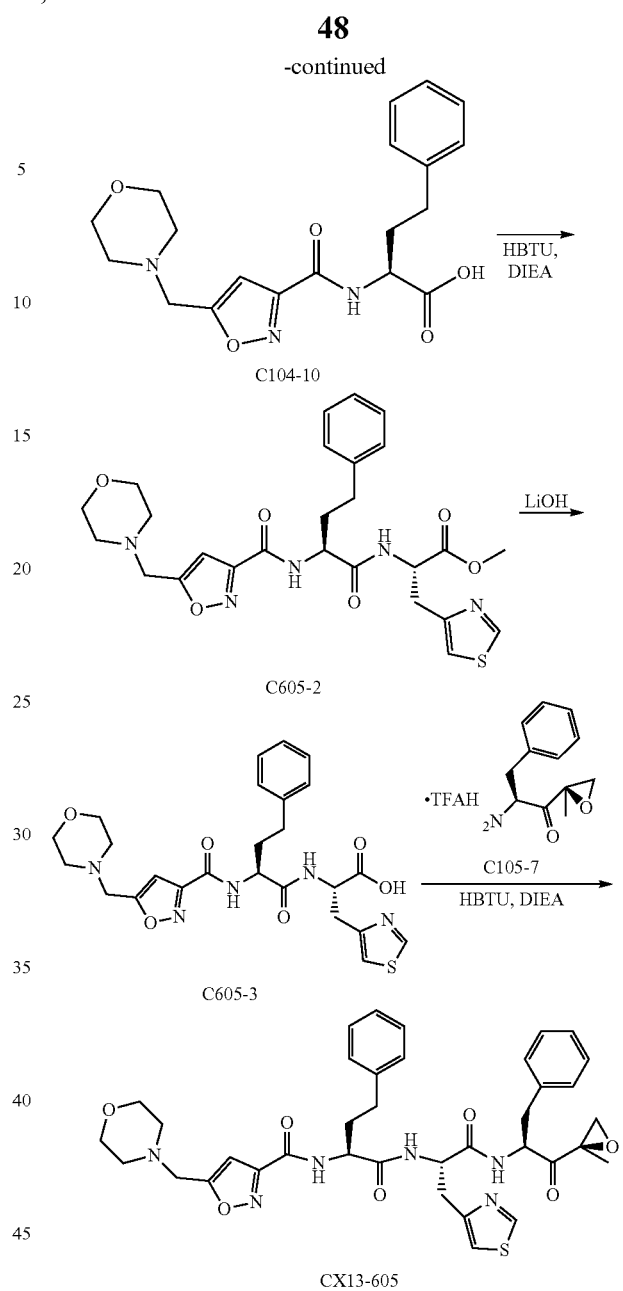

Synthesis of C605-2

To a mixture of C104-10 (240 mg, 0.64 mmol), C605-1 (143 mg, 0.77 mmol) HBTU (245 mg, 0.77 mmol) in DMF (10 mL) was added DIEA (0.5 mL) slowly via an addition funnel. The reaction was kept at room temperature for 16 hours and then diluted with EtOAc (10 mL) and brine (10 mL). The layers were separated, and the aqueous layer was extracted with EtOAc (2×10 mL). The organic layers were combined and dried over $Na_2SO_4$. The solid was removed by filtration, and the volatiles were removed under reduced pressure and purified by chromatography to give C605-2 (310 g, 89% yield) as white solid. MS (ESI) m/z: 542.0 (M+H)$^+$.

Synthesis of C605-3

To a solution of C605-2 (270 mg, 2.3 mmol) in THF was added LiOH (97.4 mg, 3.5 mmol). The solution was stirred at room temperature for 2 hours. The mixture was concentrated and acidified to pH=5, concentrated, and purified by chromatography to give C605-3 as white solid (150 mg, 61%). LC-MS: m/z 528.1 (M+H)⁺.

Preparation of CX13-605

To a cold (−5° C.) mixture of C605-3 (150 mg, 0.28 mmol), C105-7 (87 mg, 0.28 mmol), HOBt (58 g, 0.42 mmol), and HBTU (160 g, 0.42 mmol) in DMF (5 mL) was added DIEA (0.3 mL). The reaction was kept at −5° C. for 1 hour and diluted with EtOAc (10 mL) and brine (10 mL). The layers were separated, and the aqueous layer was extracted with EtOAc (2×10 mL). The organic layers were combined and dried over $Na_2SO_4$. The solid was removed by filtration, and the volatiles were removed under reduced pressure. The crude was purified by chromatography to get the compound CX13-605 (50 mg, 25.1%).

$^1$H-NMR (400 MHz, $CDCl_3$) δ 8.82 (s, 1H), 7.15-7.41 (m, 10H), 7.11 (d, J=4.30 Hz, 1H), 6.75 (s, 1H), 4.67-4.78 (m, 2H), 4.49 (d, J=3.49 Hz, 1H), 3.91 (s, 2H), 3.67-3.79 (m, 4H), 3.21-3.29 (d, J=5.10 Hz, 2H), 3.03-3.16 (m, 2H), 2.94 (d, J=5.10 Hz, 1H), 2.51-2.80 (m, 7H). 1.91-2.09 (m, 2H), 1.44 (s, 3H). MS (ESI) m/z: 715.3 (M+H)⁺.

Example 13

Synthesis of Compound CX13-606

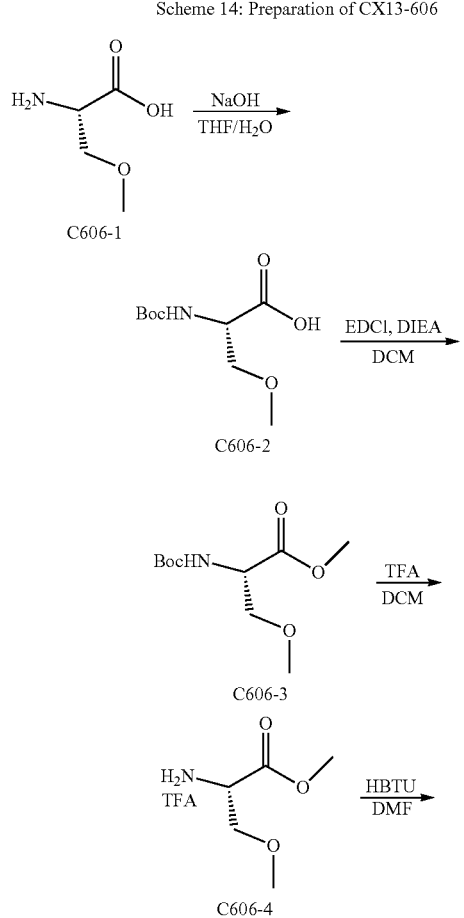

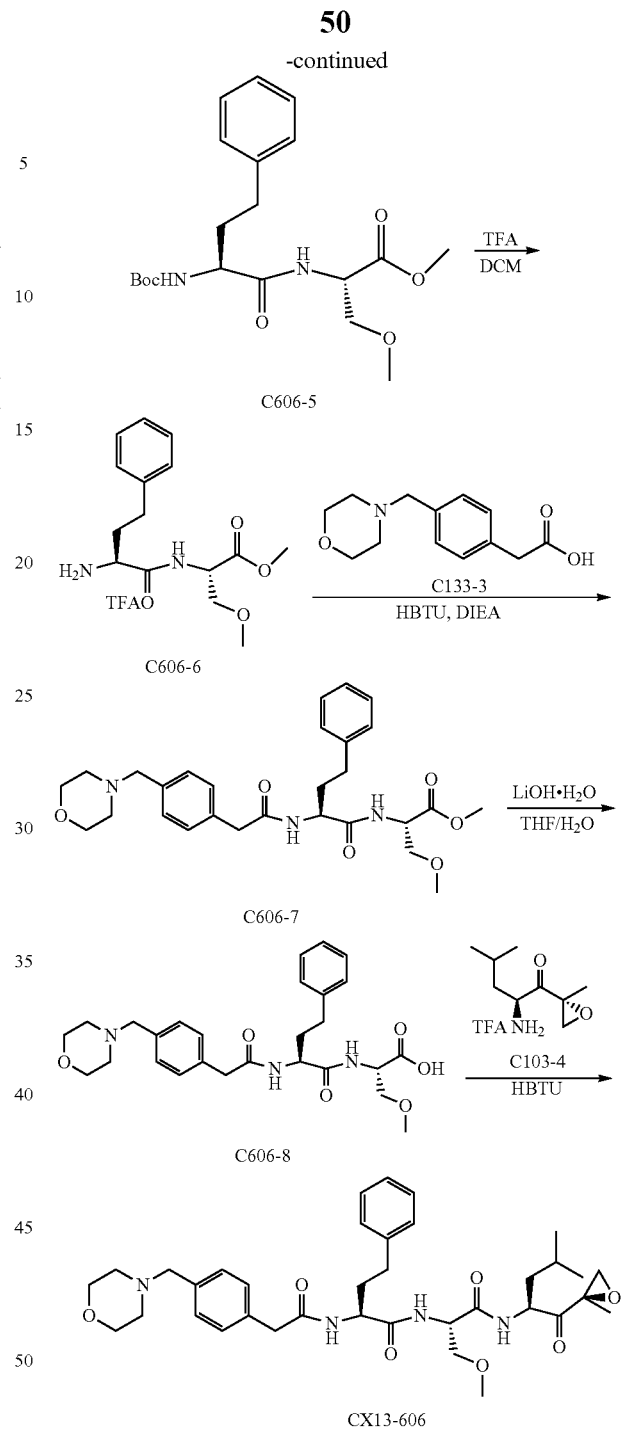

Synthesis of C606-2

To 2.0 g (17 mmol) of C606-1 were added 35 ml of a 1N aqueous sodium hydroxide solution and 35 ml of THF. A solution of di-tert-butyl dicarbonate (4.03 g, 18.5 mmol) in THF (15 mL) was then added with stirring at 0° C. The reaction mixture was stirred overnight at room temperature and concentrated by evaporation under reduced pressure. The aqueous phase was acidified to pH 4-5 with 10% aqueous citric acid and extracted with ethyl acetate. The extract was washed with brine, dried ($MgSO_4$), and evaporated to give 3.6 g of compound 606-2 (98% yield). MS (ESI) m/z: 220.1 (M+H)⁺.

Synthesis of C606-3

To a solution of C606-2 (3.6 g, 16 mmol) in DCM (40 mL) was added MeOH (2 mL), DIEA (8 mL) and EDCI (4.8 g, 25 mmol) at room temperature. The mixture was stirred at room temperature overnight, then diluted with DCM (200 mL) and brine (50 mL). The organic layer was dried over $Na_2SO_4$. The solid was removed by filtration and purified by chromatography to give C606-3 (0.8 g, 20%) as a white solid. MS (ESI) m/z: 234.1 $(M+H)^+$.

Synthesis of C606-4

To mixture of C606-3 (800 mg, 3.4 mmol) in DCM (8 mL) was added TFA (2 mL) at 0° C. The reaction was kept at 0° C. temperature for 2 hours and the volatiles were removed under reduced pressure to give the compound C606-4 (790 mg, 100% yield) as a white solid. MS (ESI) m/z: 134.1 $(M+H)^+$.

Synthesis of C606-5

To mixture of compound C606-4 (790 mg, 3.4 mmol) in DMF (10 mL) was added (S)-2-(tert-butoxycarbonylamino)-4-phenylbutanoic acid (950 mg, 3.4 mmol), HBTU (1950 mg, 5.15 mmol), HOBt (695 mg, 5.15 mmol) and DIEA (2 mL) at room temperature. The reaction was kept at room temperature for 16 hours and then diluted with EtOAc (40 mL) and brine (10 mL). The layers were separated, and the aqueous layer was extracted with EtOAc. The organic layers were combined and dried over $Na_2SO_4$. The solid was removed by filtration, and the volatiles were removed under reduced pressure and purified by chromatography to give C606-5 (1.2 g, 89%) as a white solid. MS (ESI) m/z: 395.2 $(M+H)^+$.

Synthesis C606-6

To mixture of compound C606-5 (600 mg, 1.5 mmol) in DCM (6 mL) was added TFA (2 mL) at 0° C. The reaction was kept at 0° C. for 2 hours and the volatiles were removed under reduced pressure to give 606-6 (595 mg, 100% yield) as a white solid. MS (ESI) m/z: 295.2 $(M+H)^+$.

Synthesis of C606-7

To mixture of compound C606-6 (595 mg, 1.5 mmol) in DMF (5 mL) was added C133-3 (360 mg, 1.5 mmol), HBTU (870 mg, 2.3 mmol), HOBt (311 mg, 2.3 mmol) and DIEA (1 mL) at room temperature. The reaction was kept at room temperature for 16 hours and then diluted with EtOAc (30 mL) and brine (10 mL). The layers were separated, and the aqueous layer was extracted with EtOAc (2×20 mL). The organic layers were combined and dried over $Na_2SO_4$. The solid was removed by filtration, and the volatiles were removed under reduced pressure and purified by chromatography to give 608-7 (490 mg, 63%) as a white solid. MS (ESI) m/z: 512.3 $(M+H)^+$.

Synthesis of C606-8

To a solution of compound C606-7 (490 mg, 0.96 mmol) in THF (6 mL) and water (2 mL) was added $LiOH.H_2O$ (101 mg, 2.4 mmol) at room temperature. The mixture was stirred at room temperature for 16 hours. Then acidified to PH=5, extracted with EtOAc (100 mL), dried over $Na_2SO_4$. The solid was removed by filtration, and the volatiles were removed to give 606-8 (440 mg, 92% yield) as a white solid. MS (ESI) m/z: 498.3 $(M+H)^+$.

Synthesis of CX13-606

To mixture of compound C606-8 (200 mg, 0.4 mmol) in DMF (3 mL) was added C103-4 (107 mg, 0.4 mmol), HBTU (227 mg, 0.6 mmol), HOBt (82 mg, 0.6 mmol) and DIEA (0.2 mL) at room temperature. The reaction was kept at room temperature for 16 hours and then diluted with EtOAc (30 mL) and brine (10 mL). The layers were separated, and the aqueous layer was extracted with EtOAc (2×20 mL). The organic layers were combined and dried over $Na_2SO_4$. The solid was removed by filtration, and the volatiles were removed under reduced pressure and purified by chromatography to get CX13-606 (100 mg, 38%) as a white solid.
$^1$H-NMR (400 MHz, MeOD) δ 7.33 (s, 4H), 7.24 (t, J=7.3 Hz, 2H), 7.15 (dd, J=20.9, 7.1 Hz, 3H), 4.63-4.48 (m, 2H), 4.37 (dd, J=8.3, 4.9 Hz, 1H), 3.65 (dd, J=8.8, 4.1 Hz, 4H), 3.60 (dd, J=6.1, 3.7 Hz, 3H), 3.54 (d, J=6.0 Hz, 2H), 3.24 (d, J=5.1 Hz, 1H), 2.93 (d, J=5.1 Hz, 1H), 2.69-2.52 (m, 2H), 2.46 (s, 4H), 2.18-2.04 (m, 1H), 2.01-1.85 (m, 1H), 1.76-1.63 (m, 1H), 1.54-1.42 (m, 4H), 1.35 (ddd, J=13.9, 9.0, 3.7 Hz, 1H), 0.91 (dd, J=9.7, 6.6 Hz, 6H). MS (ESI) m/z: 652.0 (M+H)+.

Example 14

Synthesis of Compound CX13-608

Scheme 15: Preparation of CX13-608

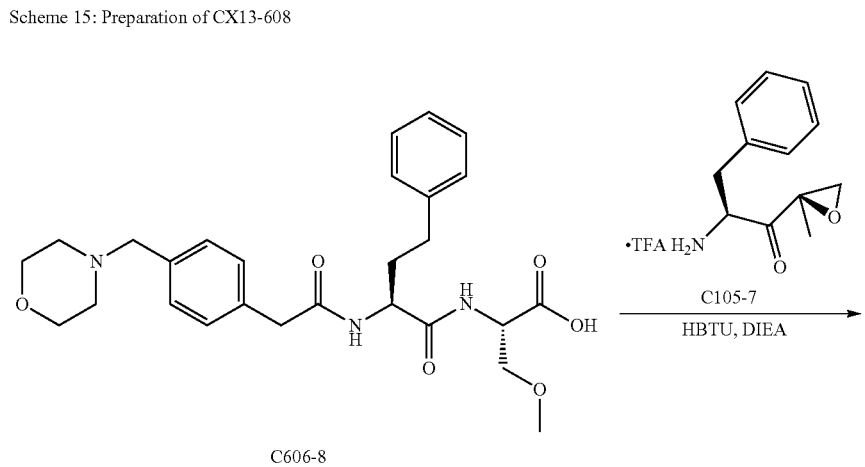

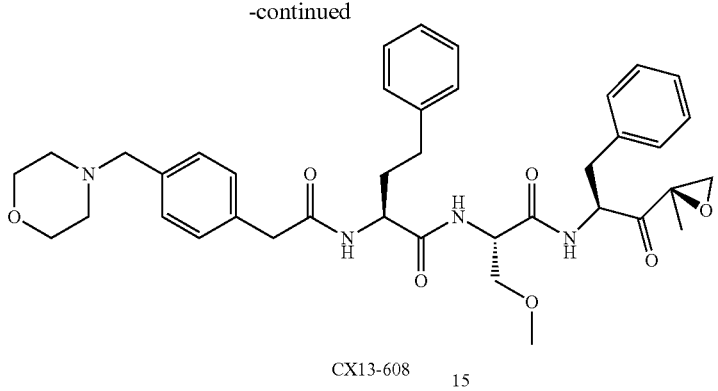

CX13-608

To C606-8 (200 mg, 0.4 mmol) in DMF (3 mL) was added C105-7 (107 mg, 0.4 mmol), HBTU (227 mg, 0.6 mmol), HOBt (82 mg, 0.6 mmol) and DIEA (0.2 mL) at room temperature. The reaction was kept at room temperature for 16 hours. Then diluted with EtOAc (30 mL) and brine (10 mL). The layers were separated, and the aqueous layer was extracted with EtOAc (2×20 mL). The organic layers were combined and dried over $Na_2SO_4$. The solid was removed by filtration, and the volatiles were removed under reduced pressure and purified by chromatography to get CX13-608 (100 mg, 36%) as a white solid.

$^1$H-NMR (400 MHz, MeOD) δ 7.32 (s, 4H), 7.27-7.12 (m, 8H), 7.11-7.08 (m, 2H), 4.79 (dd, J=8.6, 4.6 Hz, 1H), 4.47 (t, J=5.3 Hz, 1H), 4.33 (dd, J=9.2, 5.0 Hz, 1H), 3.64 (t, J=4.8 Hz, 4H), 3.51-3.59 (m, 4H), 3.50 (s, 2H), 3.30 (s, 3H), 3.25 (d, J=5.0 Hz, 1H), 3.07 (dd, J=13.9, 4.6 Hz, 1H), 2.93 (d, J=5.0 Hz, 1H), 2.76 (dd, J=13.9, 8.7 Hz, 1H), 2.64-2.49 (m, 2H), 2.43 (t, J=4.8 Hz, 4H), 2.05 (m, 1H), 1.91 (m, 1H), 1.43 (s, 3H). MS (ESI) m z: 685.3 (M+H)$^+$.

Example 15

Synthesis of Compound CX13-705

Scheme 16: Preparation of CX13-705

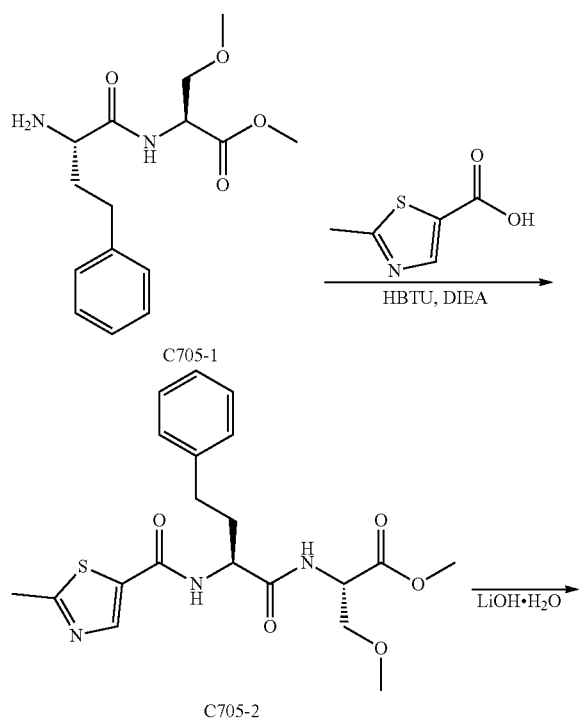

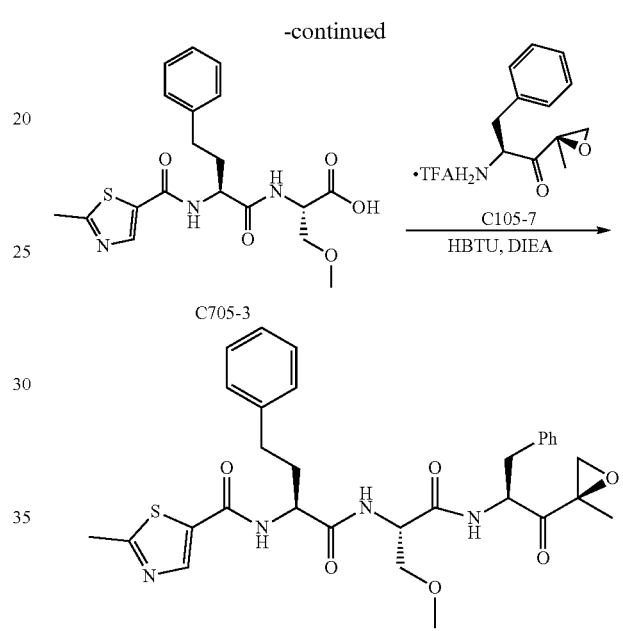

Synthesis of C705-2

To mixture of C705-1 (239 mg, 0.81 mmol) in DMF (5 mL) was added 5-methylthiazole-2-carboxylic acid (116 mg, 0.81 mmol), HBTU (370 mg, 0.97 mmol), HOBt (131 mg, 0.97 mmol) and DIEA (0.73 mL) at room temperature. The reaction was kept at room temperature for 12 hours. Then diluted with EtOAc (20 mL) and brine (10 mL). The layers were separated, and the aqueous layer was extracted with EtOAc (2×150 mL). The organic layers were combined and dried over $Na_2SO_4$. The solid was removed by filtration, and the volatiles were removed under reduced pressure and purified by chromatography to give 705-2 (300 mg, 88%) as a white solid. LC-MS: m/z 420.1 (M+H)$^+$.

Synthesis of C705-3

To a solution of C705-2 (340 mg, 0.81 mmol) in THF (6 mL) and water (2 mL) was added LiOH·H$_2$O (68 mg, 1.62 mmol) at RT. The mixture was stirred at room temperature for 2 hours. Then the mixture was acidified to PH=5, extracted with EA (20 mL), dried over $Na_2SO_4$. The solid was removed by filtration, and the volatiles were removed under reduced pressure to give 705-3 (265 mg, 78% yield) as a white solid. MS (ESI) m/z: 406.1 (M+H)$^+$.

Preparation of CX13-705

To mixture of C705-3 (265 mg, 0.65 mmol) in DMF (3 mL) was added C105-7 (130 mg, 0.72 mmol), HBTU (300 mg, 0.79 mmol), HOBt (106 mg, 0.79 mmol) and DIEA (0.6 mL) at room temperature. The reaction was kept at room temperature for 4 hours. Then diluted with EtOAc (20 mL) and brine (10 mL). The layers were separated, and the aqueous layer was extracted with EtOAc (2×20 mL). The organic layers were combined and dried over Na$_2$SO$_4$. The solid was removed by filtration, and the volatiles were removed under reduced pressure and purified by chromatography to get CX13-705 (90 mg, 23%) as a white solid.

$^1$H-NMR (400 MHz, MeOD) δ 8.22 (s, 1H), 7.31-7.13 (m, 10H), 4.80 (dd, J=8.8, 4.8 Hz, 1H), 4.57-4.48 (m, 2H), 3.66-3.52 (m, 2H), 3.25 (d, J=4.84 Hz, 1H), 3.10 (dd, J=13.97, 4.57 Hz, 1H), 2.94 (d, J=5.10 Hz, 1H), 2.66-2.82 (m, 6H), 2.02-2.16 (m, 2H); MS (ESI) m/z: 593.0 (M+H)$^+$.

Example 16

Proteasome-Activity Inhibitory Property of the Compounds

Inhibition of the chymotrypsin-like (CT-L), peptidylglutamyl peptide hydrolyzing activity (PGPH), and trypsin-like (T-L) activities of the 20S proteasome in enzymatic assays were determined using succinyl-Leu-Leu-Val-Tyr-AMC (10 μmol/L), Z-Leu-Leu-Glu-AMC (10 μmol/L) and Boc-Leu-Arg-Arg-AMC (50 μmol/L), respectively, as the substrates with purified human 20S proteasome at 2, 4 and 8 nmol/L, respectively, in the assay buffer containing 25 mM HEPES (pH7.5), 0.5 mM EDTA, 0.002% sodium dodecyl sulfate (SDS) and 0.05% NP-40. Stock solutions of the 20S proteasome inhibitors disclosed herein were prepared in dimethyl sulfoxide (DMSO) and the final DMSO concentration in the assay mixture was 1%. Reaction was conducted at room temperature for one hour. Proteasome activity was measured based on detection of the fluorophore 7-Amino-4-methylcoumarin (AMC) after cleavage from the substrates with a plate-based spectrofluorometer. IC$_{50}$ is a quantitative measure indicating the concentration of an inhibitor at which the catalytic activity of the 20S proteasome is inhibited by 50%. In certain embodiments, the proteasome inhibitory potency of the compounds is described herein in Table 1.

Example 17

Aqueous Solubility of the Compounds

To determine the solubility of the compounds, 1-5 mg of a compound was weighed into a vial. 1 mL of aqueous buffer (50 mM citrate at pH4.0) was added. The vial was shaken at 25° C. for 24 hours and then centrifuged for 10 min at 10000 rpm. The supernatant was filtered through a 0.45 μm membrane filter and analyzed for the concentration of the compound. In certain embodiments, the aqueous solubility of the compounds is described herein in Table 1.

TABLE 1

Proteasome activity inhibitory potency (IC$_{50}$) and aqueous solubility

| Compound | | Proteasome inhibition IC$_{50}$ (nM) | | | | | | Aqueous solubility (mg/mL) |
|---|---|---|---|---|---|---|---|---|
| Structure | Identification number | 20S Immunoproteasome | | | Constitutive 20S proteasome | | | at pH4.0 (50 mM citrate) |
| | | CT-L | PGPH | T-L | CT-L | PGPH | T-L | |
| [structure] | CX13-103 | 0.92 | >20000 | 14405 | 1.09 | >20000 | 15334 | 2.88 |
| [structure] | CX13-104 | 33.6 | >20000 | >20000 | 33.3 | >20000 | >20000 | 1.44 |

TABLE 1-continued

Proteasome activity inhibitory potency (IC$_{50}$) and aqueous solubility

| Compound | | Proteasome inhibition IC$_{50}$ (nM) | | | | | | Aqueous solubility (mg/mL) |
| --- | --- | --- | --- | --- | --- | --- | --- | --- |
| | Identification | 20S Immunoproteasome | | | Constitutive 20S proteasome | | | at pH4.0 (50 mM |
| Structure | number | CT-L | PGPH | T-L | CT-L | PGPH | T-L | citrate) |
| | CX13-105 | 1.34 | >20000 | >20000 | 0.97 | >20000 | >20000 | 0.021 |
| | CX13-107 | 5.1 | >20000 | 6225 | 4.74 | >20000 | 9947 | 0.083 |
| | CX13-109 | >500 | >20000 | >20000 | >500 | >20000 | >20000 | 3.49 |
| | CX13-130 | 248 | >20000 | 1648 | 62.4 | >20000 | 3601 | 1.36 |

TABLE 1-continued

Proteasome activity inhibitory potency (IC$_{50}$) and aqueous solubility

| Compound Structure | Identification number | Proteasome inhibition IC$_{50}$ (nM) | | | | | | Aqueous solubility (mg/mL) at pH4.0 (50 mM citrate) |
|---|---|---|---|---|---|---|---|---|
| | | 20S Immunoproteasome | | | Constitutive 20S proteasome | | | |
| | | CT-L | PGPH | T-L | CT-L | PGPH | T-L | |
| (structure) | CX13-133 | 4.65 | >20000 | 455 | 3.58 | >20000 | 443 | 6.36 |
| (structure) | CX13-135 | 28.1 | >20000 | 6450 | 6.56 | >20000 | 13384 | 1.16 |
| (structure) | CX13-137 | 60.4 | >20000 | 5859 | 13.5 | >20000 | 11857 | 0.91 |
| (structure) | CX13-500 | 170 | >20000 | >20000 | 121 | >20000 | >20000 | >2.35 |

TABLE 1-continued
Proteasome activity inhibitory potency (IC$_{50}$) and aqueous solubility
| Compound | | Proteasome inhibition IC$_{50}$ (nM) | | | | | | Aqueous solubility (mg/mL) |
| --- | --- | --- | --- | --- | --- | --- | --- | --- |
| Structure | Identification number | 20S Immunoproteasome | | | Constitutive 20S proteasome | | | at pH4.0 (50 mM citrate) |
| | | CT-L | PGPH | T-L | CT-L | PGPH | T-L | |
| 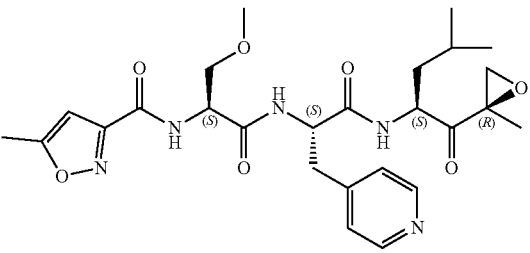 | CX13-501 | 392 | >20000 | >20000 | 113 | >20000 | >20000 | 4.48 |
| 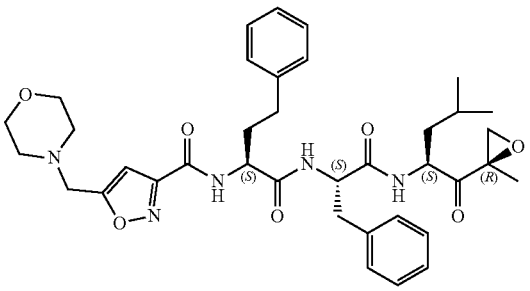 | CX13-600 | 7.41 | >20000 | 19921 | 4.28 | >20000 | >20000 | 0.02 |
| 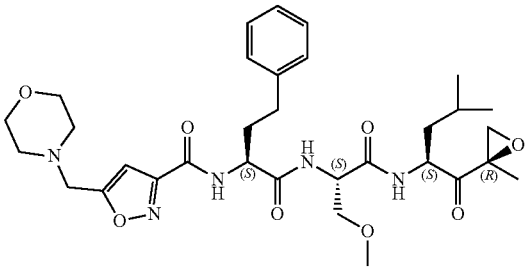 | CX13-601 | 31.7 | >20000 | >20000 | 16 | >20000 | >20000 | 0.48 |
| 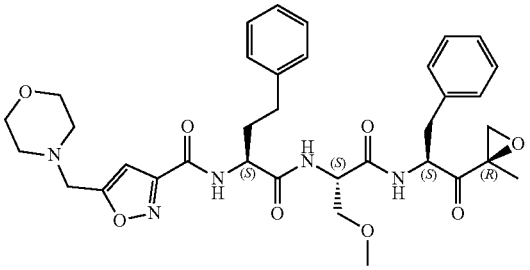 | CX13-603 | 11.1 | >20000 | >20000 | 14.2 | >20000 | >20000 | 0.52 |
| 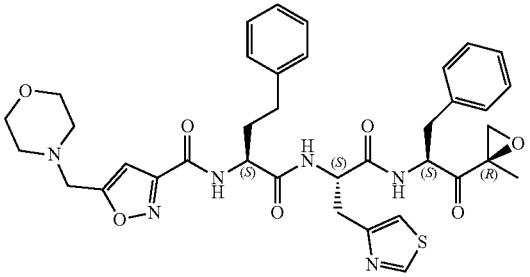 | CX13-605 | 6.81 | >20000 | >20000 | 12.2 | >20000 | >20000 | 0.12 |

TABLE 1-continued

Proteasome activity inhibitory potency (IC$_{50}$) and aqueous solubility

| Compound Structure | Identification number | Proteasome inhibition IC$_{50}$ (nM) | | | | | | Aqueous solubility (mg/mL) at pH4.0 (50 mM citrate) |
| --- | --- | --- | --- | --- | --- | --- | --- | --- |
| | | 20S Immunoproteasome | | | Constitutive 20S proteasome | | | |
| | | CT-L | PGPH | T-L | CT-L | PGPH | T-L | |
| 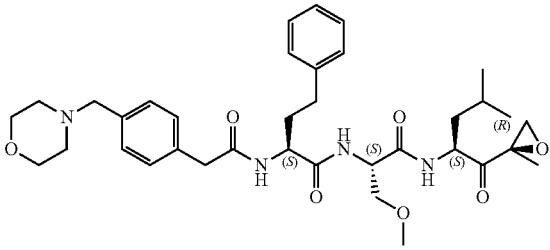 | CX13-606 | 59.3 | >20000 | 186 | 6.1 | >20000 | 297 | 3.73 |
| 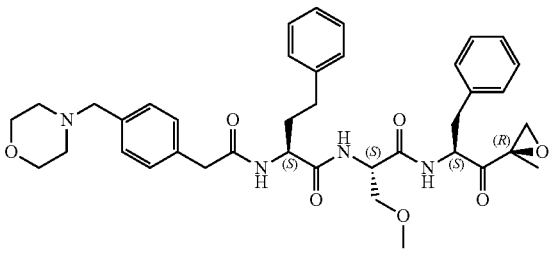 | CX13-608 | 4.26 | >20000 | 542 | 3.73 | >20000 | 490 | 1.43 |
| 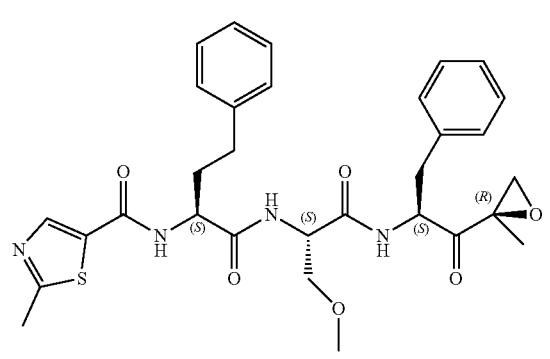 | CX13-705 | 15.3 | >20000 | >20000 | 9.75 | >20000 | 15778 | 0.02 |
| 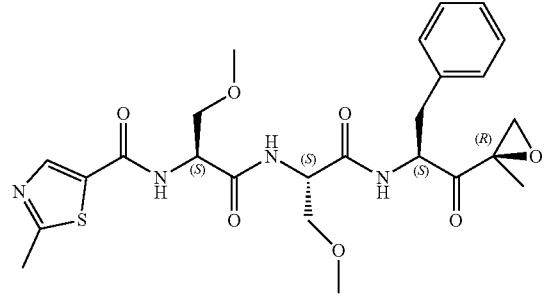 | CX13-709 | 256 | >20000 | >20000 | 124 | >20000 | >20000 | 0.57 |

Example 18

Inhibition of proteasome activity in blood samples collected from mice administrated of a compound described herein at a tolerated dose.

Balb/c mice were administered of either a vehicle (20% (w/v) hydroxypropyl-β-cyclodextrin in 10 mM sodium citrate at pH3.5), or a compound described herein at a tolerated dose via intravenous injection at 10 mg/kg or oral gavage at 30 mg/kg. One hour after dosing, whole blood samples were collected into tubes containing sodium heparin by cardiac puncture and centrifuged at 150×g for 5 minutes at 4° C. The resulting pellet was washed using ice-cold phosphate buffered saline (PBS) three times. Every time, the pellet was re-suspended in 1 mL cold PBS and centrifuged at 6000×g for 10 minutes at 4° C. After the last wash, the pelleted cells were lysed by the addition of 100 μL of the lysis buffer (PBS containing 5 mM EDTA, pH7.4) for 1 hour and then centrifuged at 6000×g for 10 minutes at 4° C. The supernatant was transferred to a new tube and the cell pellet was discarded. The concentration of the blood lysate was measured by BCA method. 10 μg of protein was used for measurement of CT-L, and 30 μg of protein was used for measurement of PGPH and T-L activities. Succinyl-Leu-Leu-Val-Tyr-AMC (25 μmol/L), Z-Leu-Leu-Glu-AMC (10 μmol/L) or Boc-Leu-Arg-Arg-AMC (10 μmol/L) was then added as the substrate, respectively, for CT-L, PGPH or T-L. The mixture was incubated for 60 minutes at 37° C. The free AMC fluorescence was quantified using a 360/460 nm filter set in a fluorometer to measure the CT-L, PGPH or T-L activities of the 20S proteasome. Percent inhibition of the proteasome activity was calculated by comparing the samples collected from the mice administrated of a compound described herein to the samples collected from the mice administrated of the vehicle. The percentage inhibition of the proteasome activities is described herein in FIG. 1. As shown in FIG. 1, the compounds tested inhibited the CT-L activity in the blood samples. Notably, CX 13-603 administered via oral gavage inhibited the CT-L activity in blood samples. CX13-608 simultaneously inhibited both CT-L and T-L activity of the proteasome in the blood samples.

Example 19

Anti-tumor efficacy of the compounds described herein in mice bearing human tumor xenografts.

Figure 2A:
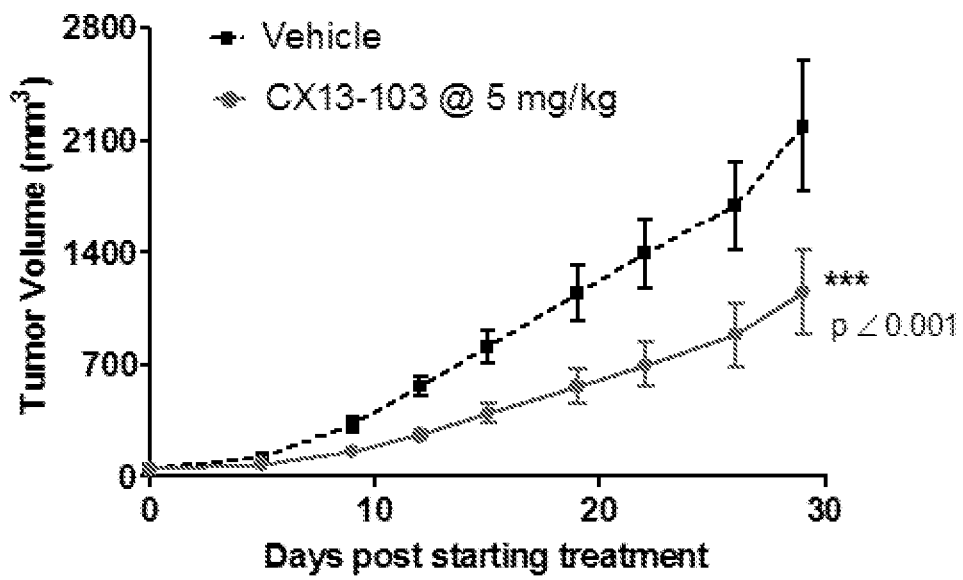
FIG. 2A shows the antitumor efficacy of CX13-103 in mice bearing HT-29 human colorectal adenocarcinoma xenografts. Statistical analysis was conducted using 2-way ANOVA.
Figure 2B:
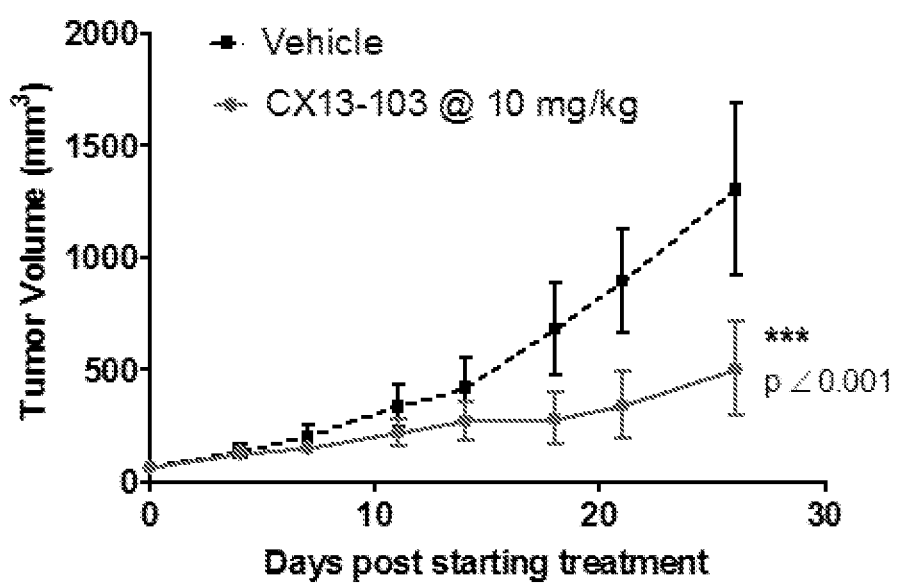
FIG. 2B shows the antitumor efficacy of CX13-103 in mice bearing RL human lymphoma xenografts. Statistical analysis was conducted using 2-way ANOVA.

Female mice (NIH III HO nude mice purchased from Charles River Laboratories (about 20 g, 5-6 weeks old) were maintained in cages during the experimental period. $3 \times 10^6$ human colon cancer cells (HT-29) from ATCC® (HTB-38™) or $1 \times 10^7$ human B cell lymphoma cells (RL) from ATCC® (CRL38™) in 100 μL phosphate buffer saline were injected subcutaneously in the right flank of the mice. When average tumor size reached about 20-30 mm³ for HT29 or about 60-90 mm³ for RL, the animals with tumors were randomized to different groups (7-10 mice each group) such that all groups had an equal distribution of tumor sizes. The animals were administrated via intravenous injection of a vehicle (10% (w/v) hydroxypropyl-3-cyclodextrin, 10 mM citrate, pH4.0) or a solution containing CX13-103 prepared in the vehicle. The animals were administrated three times per week on Days 1, 2 and 5 for 4-5 weeks. Tumor sizes were measured by caliper 2 or 3 times per week. Tumor volume was calculated by the formula: length×width²/2. Statistical analysis was conducted using 2-way ANOVA. As shown in FIG. 2A and FIG. 2B, administration of CX13-103 significantly suppressed tumor growth.

The invention claimed is:
1. A method of treating a proteasome-related disease or condition selected from adenocarcinoma, colorectal cancer, lymphoma, myeloma, colon cancer, breast cancer, leukemia, prostate cancer, lung cancer, melanoma, uterine sarcoma, comprising administering a therapeutically effective amount of a compound having a structure shown in Formula (I), or an enantiomer, diastereomer, tautomer, pharmaceutically acceptable salt or solvate thereof:

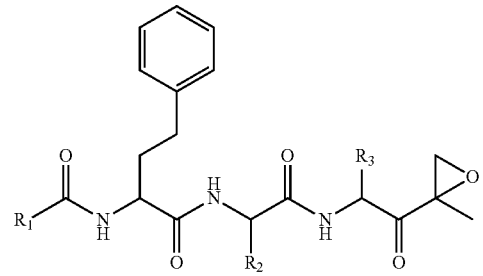

Formula (I)

wherein $R_1$ is —$(CH_2)m$—$R_4$, wherein m=0 or 1, $R_4$ is selected from the group consisting of $C_{1-10}$alkyl,

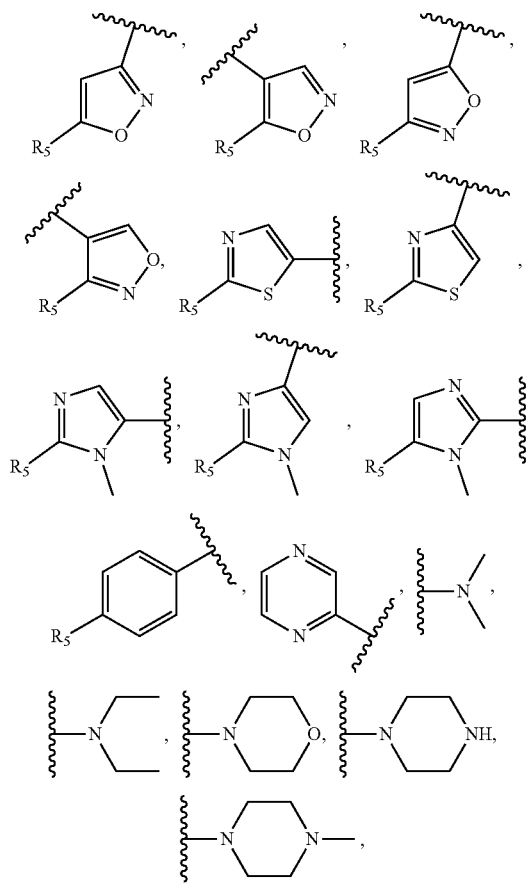

wherein
each of $R_5$ is independently H, hydroxyl, $C_{1-10}$alkyl, $C_{1-10}$alkoxyl, $C_{1-10}$hydroxyalkyl, $C_{1-10}$alkyloxyalkyl, $NH_2$, $NHR_6$, —$R_7$—O(C=O)—$R_8$, —$R_7$—(C=O) X—$R_8$, —$R_7$—$OPO_3M_1M_2$,

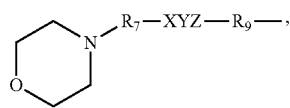

-continued

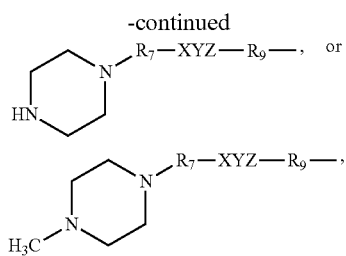

wherein
R$_6$ is C$_{1-10}$alkyl, phenyl, —(C=O)—C$_{1-6}$alkyl or —(C=O)-phenyl,
each of R$_7$, and R$_9$ is independently absent or C$_{1-10}$alkylene,
each of R$_8$ is independently H, hydroxyl, metal or C$_{1-10}$alkyl, C$_{1-10}$alkylene, —NR$_{10}$R$_{11}$, or —OPO$_3$M$_1$M$_2$,
each of R$_{10}$ and R$_{11}$ is independently H, C$_{1-10}$alkyl or substituted C$_{1-10}$alkyl,
each of M$_1$, and M$_2$ is independently H or metal,
X is absent or O,
Y is absent or —(C=O)—,
Z is absent or O; and
each of R$_2$ and R$_3$ is independently selected from C$_{1-10}$alkyl, C$_{1-10}$alkenyl, C$_{1-10}$hydroxyalkyl, C$_{1-10}$alkoxyalkyl, aryl, C$_{1-10}$aralkyl, heteroaryl, C$_{1-10}$heteroaralkyl, heterocyclyl, C$_{1-10}$heterocycloalkyl, carbocyclyl, and C$_{1-10}$carbocycloalkyl, wherein R$_3$ is not 4-pyridylmethyl when R$_1$ is

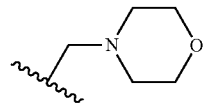 [SMILES: *CN1CCOCC1]

and R$_2$ is isobutyl.

2. The method of claim 1, wherein the compound has the configuration shown in Formula (II):

Formula (II)

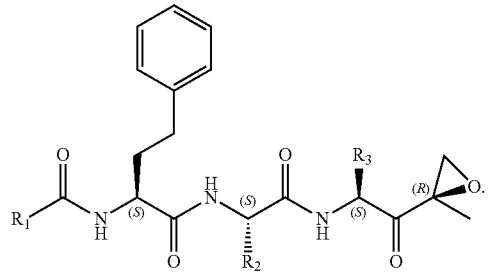

3. The method of claim 1, wherein R$_4$ in the compound of Formula (I) is selected from the group consisting of methyl,

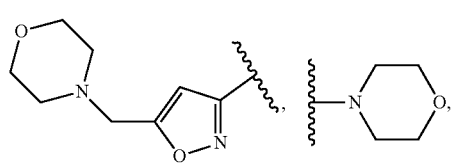

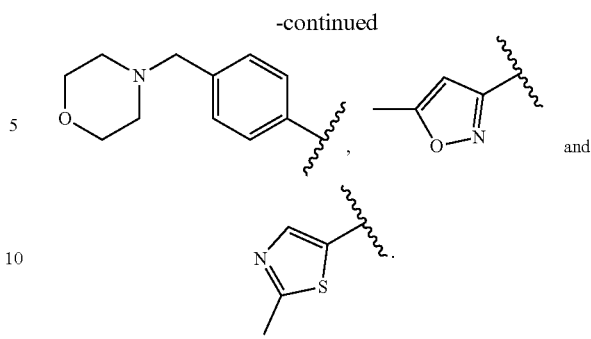

4. The method of claim 1, wherein R$_2$ in the compound of Formula (I) is C$_{1-10}$alkyl, C$_{1-10}$alkoxyalkyl, aryl, heteroaryl, C$_{1-10}$aralkyl or C$_{1-10}$heteroaralkyl.

5. The method of claim 4, wherein R$_2$ in the compound of Formula (II) is methyl-oxy-methyl, 4-pyridylmethyl, isobutyl, benzyl or 4-thiazolyl-methyl.

6. The method of claim 1, wherein R$_3$ in the compound of Formula (I) is C$_{1-10}$alkyl, aryl, heteroaryl, C$_{1-10}$aralkyl or C$_{1-10}$heteroaralkyl.

7. The method of claim 6, wherein R$_3$ is isobutyl, 4-pyridylmethyl or benzyl.

8. The method of claim 1, wherein the compound has a structure shown below or a pharmaceutically acceptable salt or solvate thereof

CX13-103

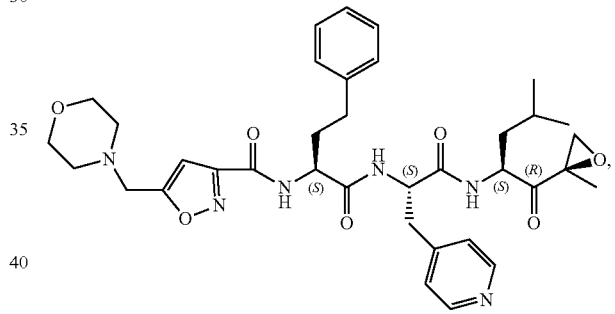

CX13-104

CX13-105

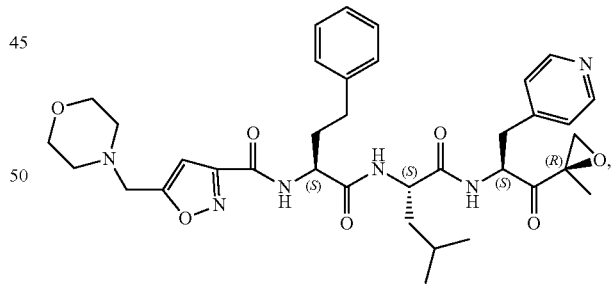

CX13-107
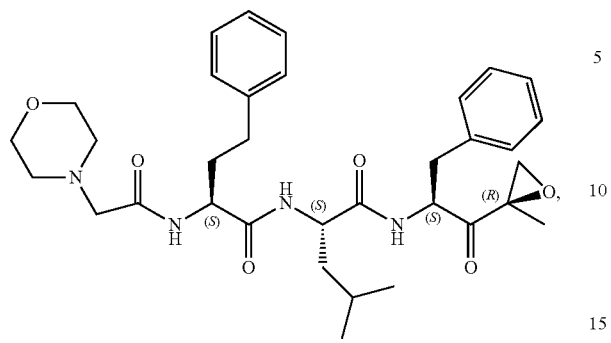
CX13-130
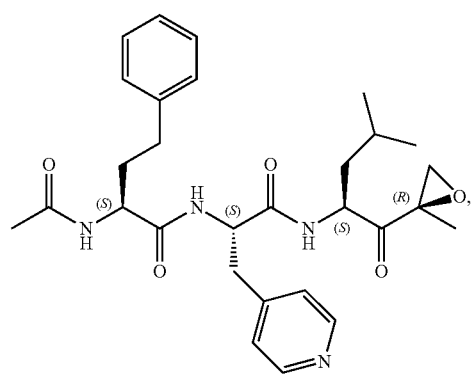
CX13-133
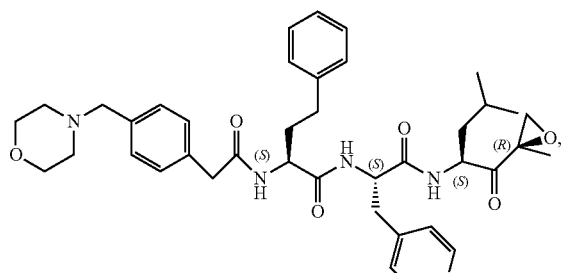
CX13-135
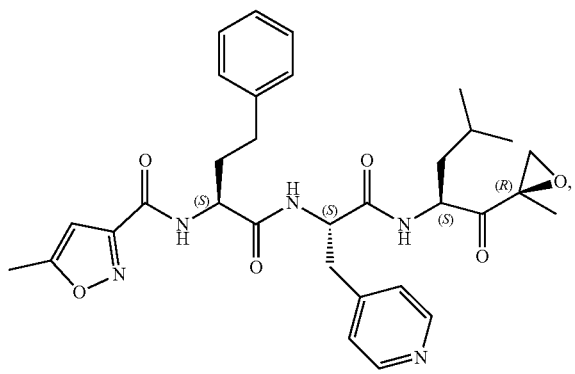
CX13-137
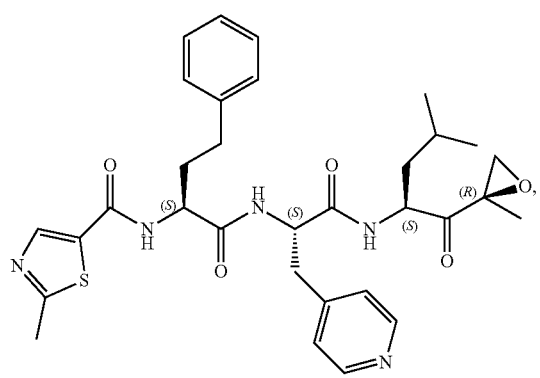
CX13-600
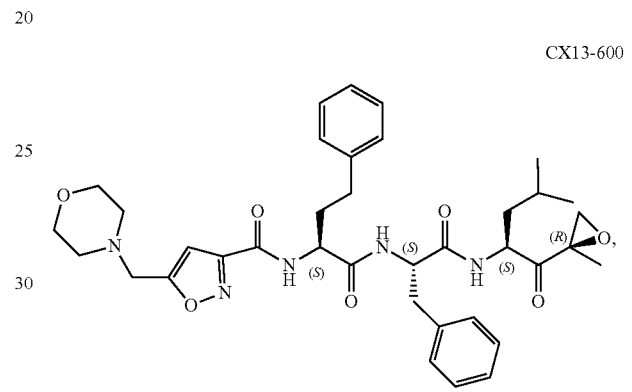
CX13-601
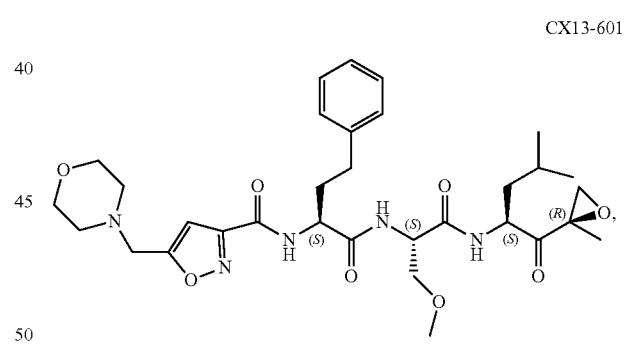
CX13-603
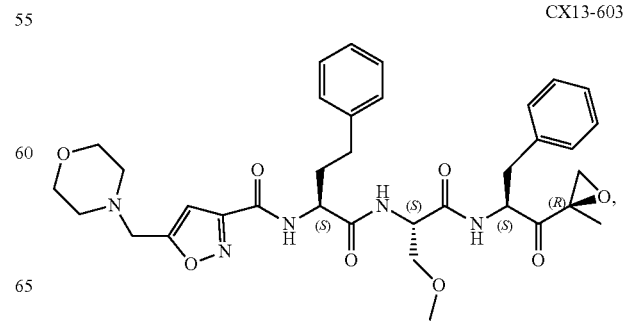

-continued

CX13-605

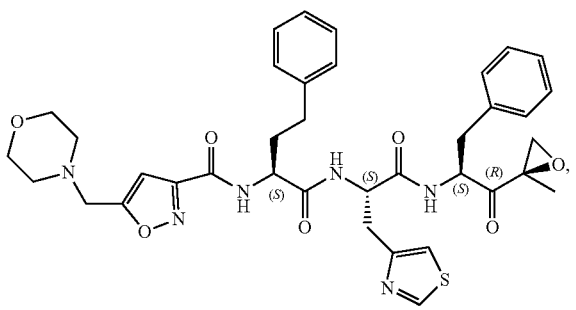

CX13-606

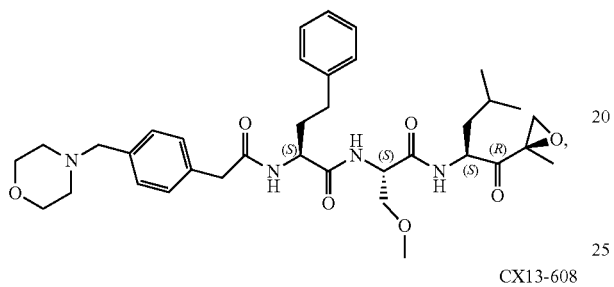

CX13-608

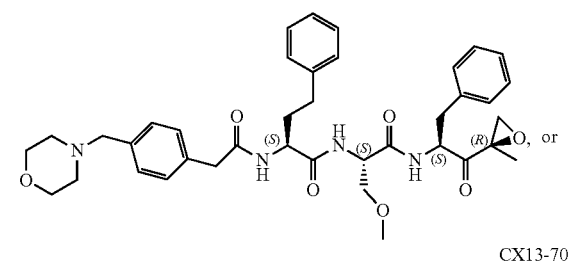

CX13-705

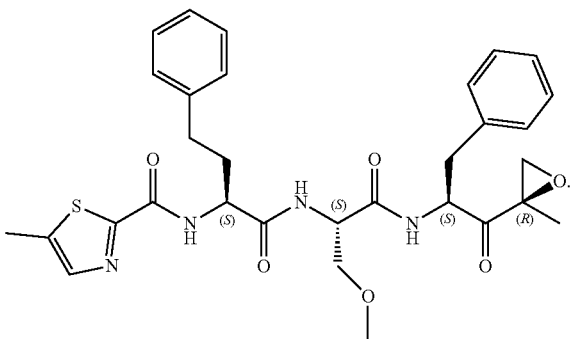

9. The method of claim 1, wherein the compound of Formula (I) is administered as a pharmaceutical composition comprising a compound of Formula (I), and a pharmaceutically acceptable carrier.

10. The method of claim 1, wherein the compound of Formula (I) is administered through a parenteral route.

11. The method of claim 10, wherein the compound is administered, intravenously, intraarterially, intrathecally, intraperitoneally, intraspinally, intrasternally, or through infusion.

12. The method of claim 1, wherein the compound is administered orally.

13. The method of claim 1, wherein the 20S proteasome-related disease or condition is lymphoma.

14. The method of claim 1, wherein the 20S proteasome-related disease or condition is adenocarcinoma, colorectal cancer, lymphoma, myeloma, colon cancer, breast cancer, leukemia, prostate cancer, lung cancer, or melanoma.

15. The method of claim 1, wherein the compound of Formula (I) inhibits the chymotrypsin-like (CT-L) and trypsin-like (T-L) activities of the 20S proteasome.

16. The method of claim 15, wherein the compound inhibits the chymotrypsin-like (CT-L) activity, peptidylglutamyl peptide hydrolyzing activity (PGPH), and trypsin-like (T-L) activity of the 20S proteasome.

17. A method to specifically inhibit catalytic activity of the 20S proteasome in a subject, comprising administering to the subject a therapeutically effective amount of a compound of Formula (I):

Formula (I)

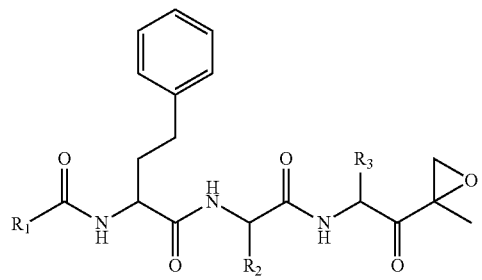

wherein $R_1$ is —$(CH_2)$m-$R_4$, wherein m=0 or 1, $R_4$ is selected from the group consisting of $C_{1-10}$alkyl,

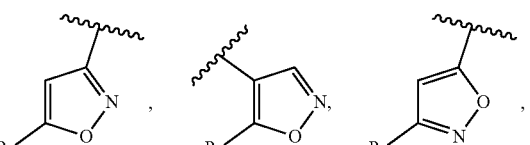

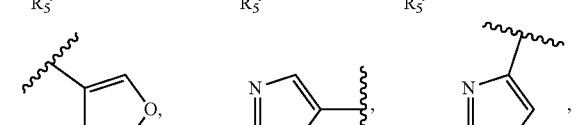

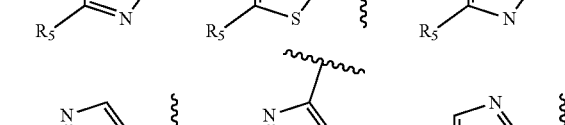

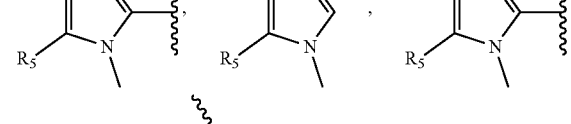

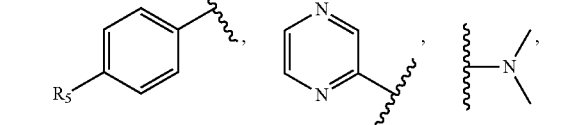

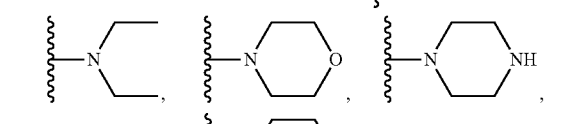

wherein
each of $R_5$ is independently H, hydroxyl, $C_{1-10}$alkyl, $C_{1-10}$alkoxyl, $C_{1-10}$hydroxyalkyl, $C_{1-10}$alkyloxyalkyl, $NH_2$, $NHR_6$, —$R_7$—O(C=O)-$R_8$, —$R_7$—(C=O)X—$R_8$, —$R_7$—$OPO_3M_1M_2$, wherein
- R$_6$ is C$_{1-10}$alkyl, phenyl, —(C=O)—C$_{1-6}$alkyl or —(C=O)-phenyl,
- each of R$_7$, and R$_9$ is independently absent or C$_{1-10}$alkylene,
- each of R$_8$ is independently H, hydroxyl, metal or C$_{1-10}$alkyl,
- —C$_{1-10}$alkylene, —NR$_{10}$R$_{11}$, or —OPO$_3$M$_1$M$_2$,
- each of R$_{10}$ and R$_{11}$ is independently H, C$_{1-10}$alkyl or substituted C$_{1-10}$alkyl,
- each of M$_1$, and M$_2$ is independently H or metal,
- X is absent or O,
- Y is absent or —(C=O)—,
- Z is absent or O; and each of R$_2$ and R$_3$ is independently selected from C$_{1-10}$alkyl, C$_{1-10}$alkenyl, C$_{1-10}$hydroxyalkyl, C$_{1-10}$alkoxyalkyl, aryl, C$_{1-10}$aralkyl, heteroaryl, C$_{1-10}$heteroaralkyl, heterocyclyl, C$_{1-10}$heterocycloalkyl, carbocyclyl, and C$_{1-10}$carbocycloalkyl, wherein R$_3$ is not 4-pyridylmethyl when R$_1$ is and R$_2$ is isobutyl; or a pharmaceutically acceptable salt thereof.

18. The method of claim 17, wherein the compound of Formula (I) is selected from the following structures, or a pharmaceutically acceptable salt thereof:

CX13-103

CX13-104

CX13-105

CX13-107

CX13-130

CX13-133
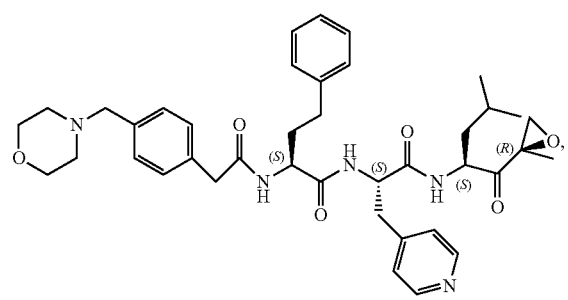
CX13-135
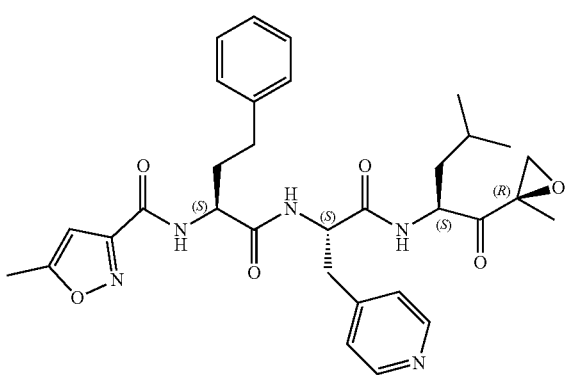
CX13-137
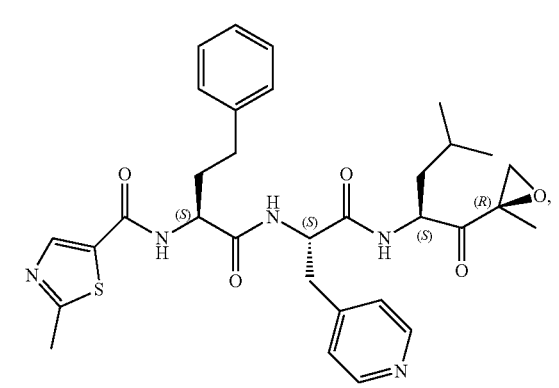
CX13-600
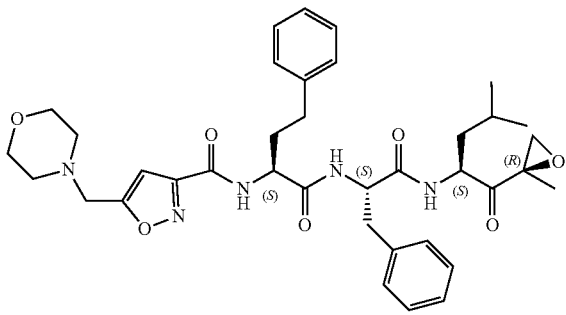
CX13-601
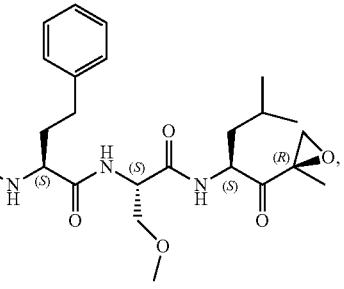
CX13-603
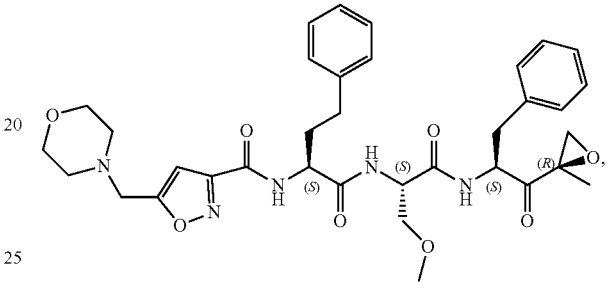
CX13-605
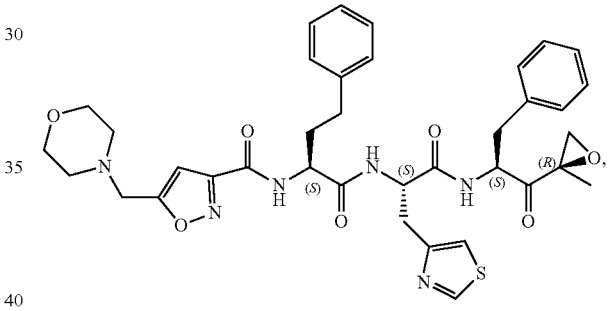
CX13-606
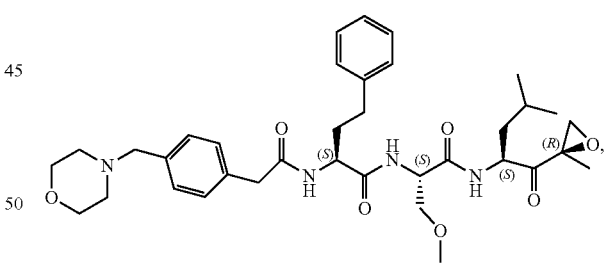
CX13-608
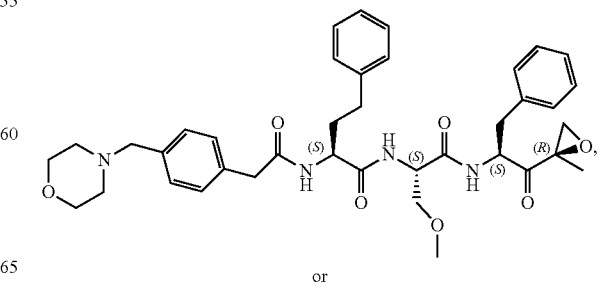
or CX13-705
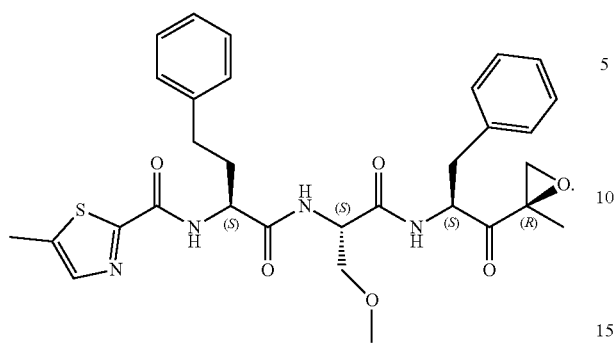
19. The method of claim 17, wherein the compound of Formula (I) inhibits the chymotrypsin-like (CT-L) and trypsin-like (T-L) activities of the 20S proteasome.
20. The method of claim 17, wherein the compound inhibits the chymotrypsin-like (CT-L) activity, peptidylglutamyl peptide hydrolyzing activity (PGPH), and trypsin-like (T-L)-activity of the 20S proteasome.
* * * * *